United States Patent
Chang et al.

(10) Patent No.: US 7,744,712 B2
(45) Date of Patent: *Jun. 29, 2010

(54) ELASTIC COMPOSITE, AND A SYSTEM AND METHOD FOR MAKING THE ELASTIC COMPOSITE

(75) Inventors: Kuo-Shu Edward Chang, Charlotte, NC (US); Anne Smid, Wolvega (NL); Patrick King Yu Tsang, Tuen Mun (HK); Andrew C. Wright, Derbyshire (GB); William S. Sayers, Delaware, OH (US)

(73) Assignee: DSG Technology Holdings, Ltd, Tortola (VG)

( * ) Notice: Subject to any disclaimer, the term of this patent is extended or adjusted under 35 U.S.C. 154(b) by 274 days.

This patent is subject to a terminal disclaimer.

(21) Appl. No.: 11/801,293

(22) Filed: May 9, 2007

(65) Prior Publication Data

US 2008/0093015 A1    Apr. 24, 2008

Related U.S. Application Data

(60) Division of application No. 11/475,288, filed on Jun. 26, 2006, which is a continuation-in-part of application No. 11/021,424, filed on Dec. 23, 2004, now Pat. No. 7,361,246.

(60) Provisional application No. 60/532,480, filed on Dec. 24, 2003.

(51) Int. Cl.
*B32B 37/00* (2006.01)
*A61F 13/15* (2006.01)

(52) U.S. Cl. .................. 156/179; 156/177; 156/178

(58) Field of Classification Search ......... 156/177–179, 156/439, 438, 174
See application file for complete search history.

(56) References Cited

U.S. PATENT DOCUMENTS 1,195,949 A * 8/1916 Carney ................. 156/168
2,718,254 A * 9/1955 Carlson ................ 156/172

(Continued)

FOREIGN PATENT DOCUMENTS

EP    1520569 A1    4/2000

(Continued)

OTHER PUBLICATIONS

Examiner's Report from Australian Patent Application No. 2004311805, dated Jan. 25, 2010.

*Primary Examiner*—Jeff H Aftergut
(74) *Attorney, Agent, or Firm*—Alberto Q. Amatong, Jr.; The Amatong Law Firm, PLLC

(57) ABSTRACT

A method of making an elastic composite is provided. The method entails conveying a first web of material along a web plane path. The method also entails applying a first section of a first elastic strand onto the first web and generally transversely to the web plane path and applying a second section of a second elastic strand onto the first web and generally transversely to the web plane path. These applying steps are repeated while performing the conveying step, thereby arranging a plurality of first and second elastic elements on the first web, in generally parallel relation to one another. The resultant composite is suitable for incorporation into a disposable absorbent garment, textile or fabric structure, and the like.

27 Claims, 26 Drawing Sheets

U.S. PATENT DOCUMENTS

| | | | |
|---|---|---|---|
| 2,902,395 A | 9/1959 | Hirschy et al. | |
| 3,041,230 A * | 6/1962 | Diehl | 156/172 |
| 3,627,621 A | 12/1971 | Mowers | |
| 3,649,411 A | 3/1972 | Bolles | |
| 3,663,331 A | 5/1972 | Solbeck | |
| 3,800,796 A | 4/1974 | Jacob | |
| 3,801,401 A | 4/1974 | Cope et al. | |
| 4,527,990 A | 7/1985 | Sigl | |
| 4,602,973 A | 7/1986 | Holroyd et al. | |
| 5,221,390 A | 6/1993 | Persson et al. | |
| 5,338,382 A | 8/1994 | Johnson et al. | |
| 5,531,729 A | 7/1996 | Coles et al. | |
| 5,591,152 A | 1/1997 | Buell et al. | |
| 5,628,741 A | 5/1997 | Buell et al. | |
| 5,685,873 A | 11/1997 | Bruemmer | |
| 5,779,691 A | 7/1998 | Schmitt | |
| 5,807,371 A | 9/1998 | Toyoda et al. | |
| 5,938,652 A | 8/1999 | Sauer | |
| 6,086,571 A | 7/2000 | Guevara et al. | |
| 6,096,151 A * | 8/2000 | Edwards et al. | 156/174 |
| 6,123,694 A | 9/2000 | Pieniak et al. | |
| 6,146,369 A | 11/2000 | Hartman et al. | |
| 6,336,922 B1 | 1/2002 | Vangompel et al. | |
| 6,340,782 B1 | 1/2002 | Kling et al. | |
| 6,419,667 B1 | 7/2002 | Avalon et al. | |
| 6,425,430 B1 * | 7/2002 | Ward et al. | 156/440 |
| 6,454,750 B1 | 9/2002 | Vogt et al. | |
| 6,454,752 B1 | 9/2002 | Huang et al. | |
| 6,649,001 B2 | 11/2003 | Heden et al. | |
| 6,855,223 B2 * | 2/2005 | Johnson | 156/177 |
| 7,361,246 B2 * | 4/2008 | Chang et al. | 156/177 |
| 2002/0038110 A1 | 3/2002 | Kusibojoska et al. | |
| 2002/0151863 A1 | 10/2002 | Toyoshima | |
| 2002/0177829 A1 | 11/2002 | Fell et al. | |
| 2003/0064652 A1 | 4/2003 | Heden et al. | |
| 2003/0069557 A1 | 4/2003 | Driskell et al. | |
| 2003/0083634 A1 | 5/2003 | Fernfors | |
| 2003/0089454 A1 | 5/2003 | Johnson | |
| 2003/0109844 A1 | 6/2003 | Gibbs | |
| 2003/0139725 A1 | 7/2003 | Gibbs | |
| 2003/0144643 A1 | 7/2003 | Jarpenberg et al. | |
| 2004/0026011 A1 | 2/2004 | Edwards et al. | |
| 2005/0095942 A1 | 5/2005 | Mueller et al. | |
| 2005/0131373 A1 | 6/2005 | Wright et al. | |
| 2005/0139311 A1 | 6/2005 | Chang et al. | |

FOREIGN PATENT DOCUMENTS

| | | |
|---|---|---|
| EP | 1188427 | 3/2002 |
| EP | 1520569 | 4/2005 |
| JP | 2002-192641 | 7/2002 |
| WO | 95/19258 A1 | 7/1995 |
| WO | 01/00915 | 1/2001 |
| WO | 02/32364 A1 | 4/2002 |
| WO | 03/041627 | 5/2003 |
| WO | 03/017903 A1 | 6/2003 |
| WO | 2004/087416 A1 | 10/2004 |
| WO | 2005/060910 | 7/2005 |

* cited by examiner

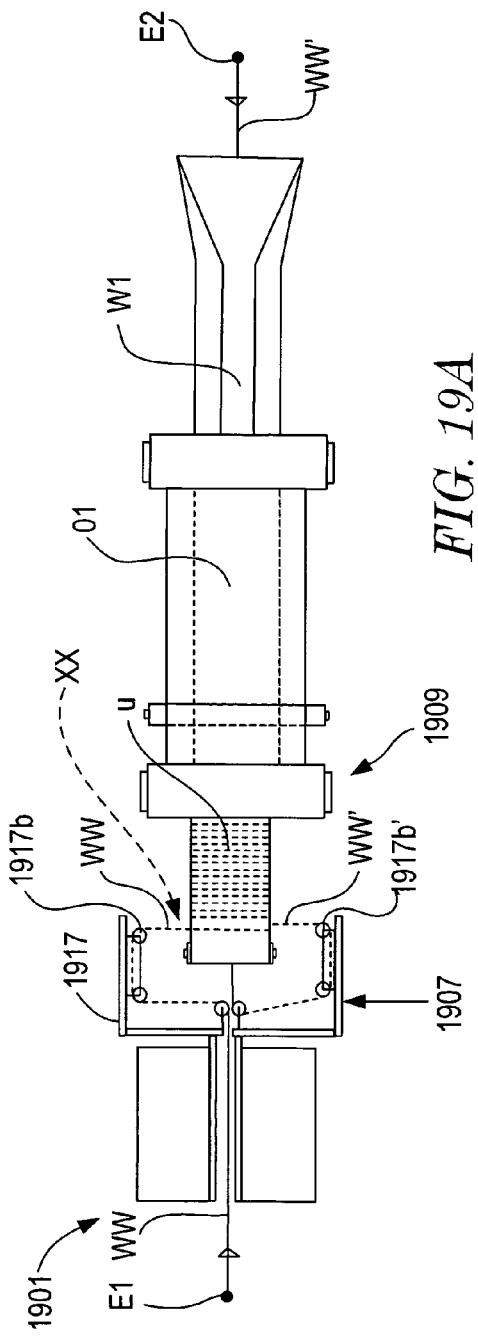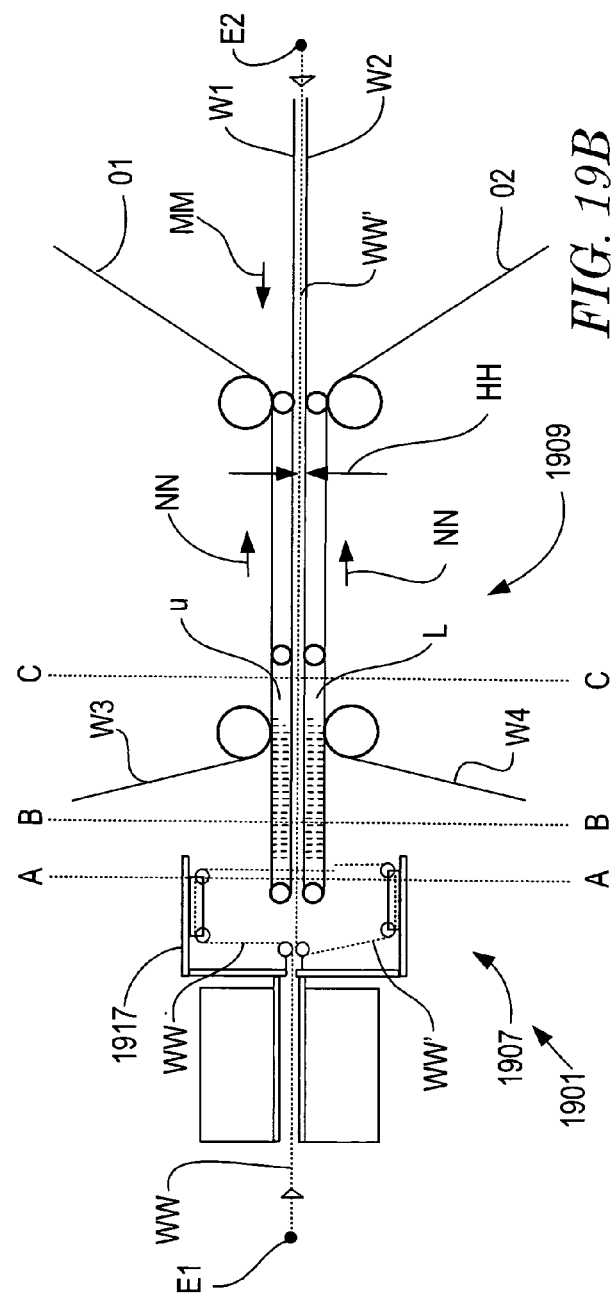
FIG. 19A
FIG. 19B

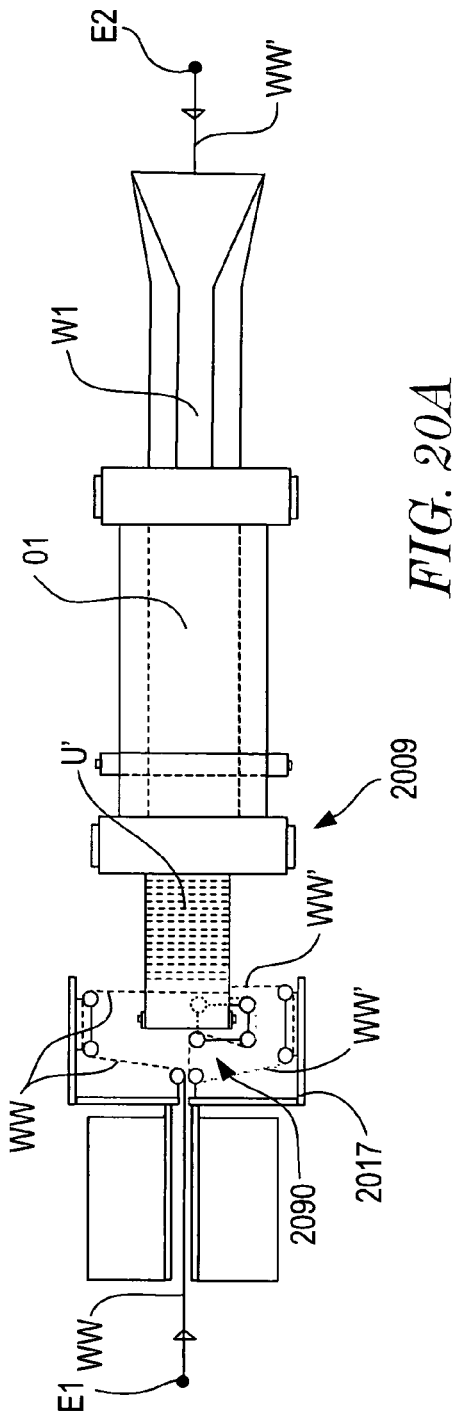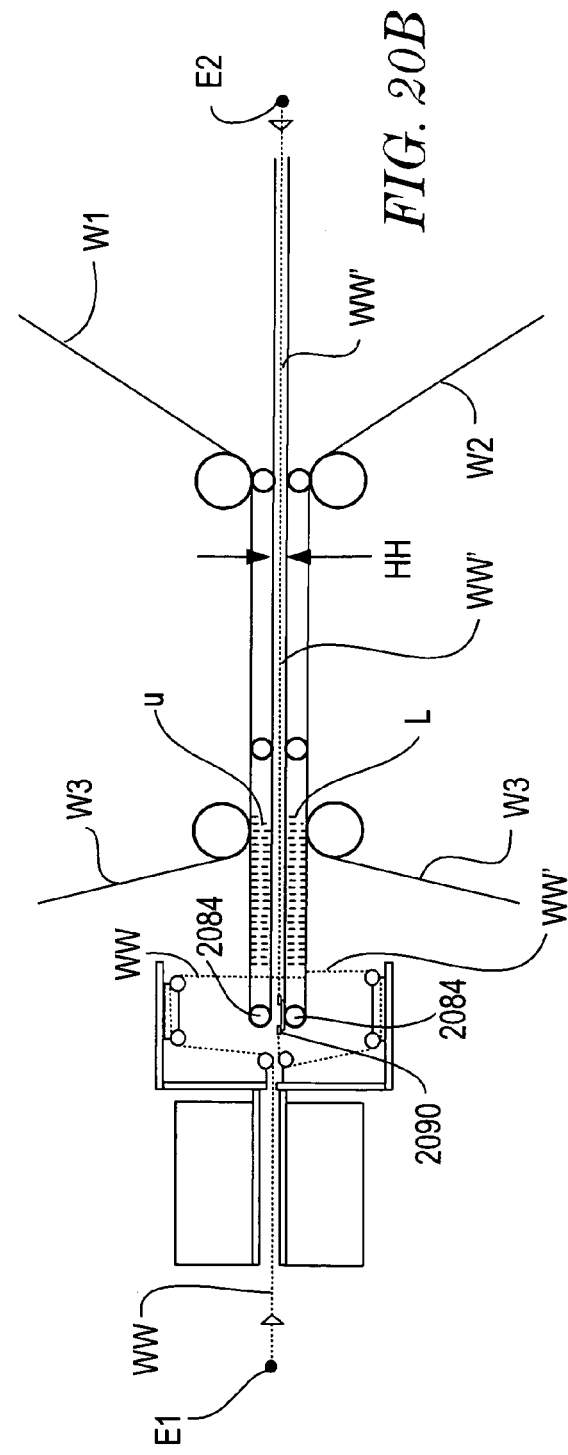

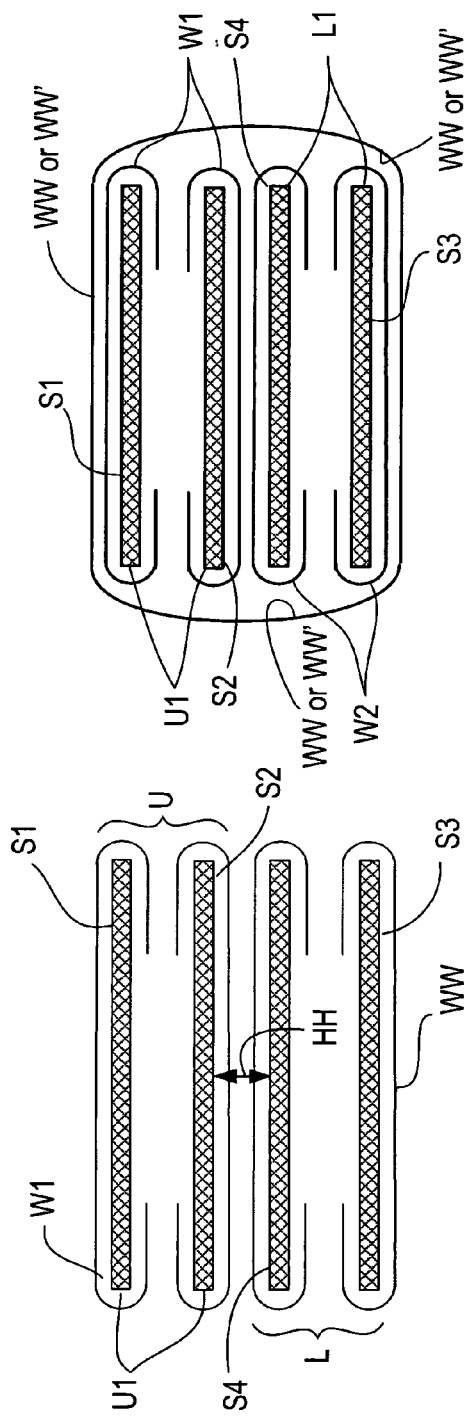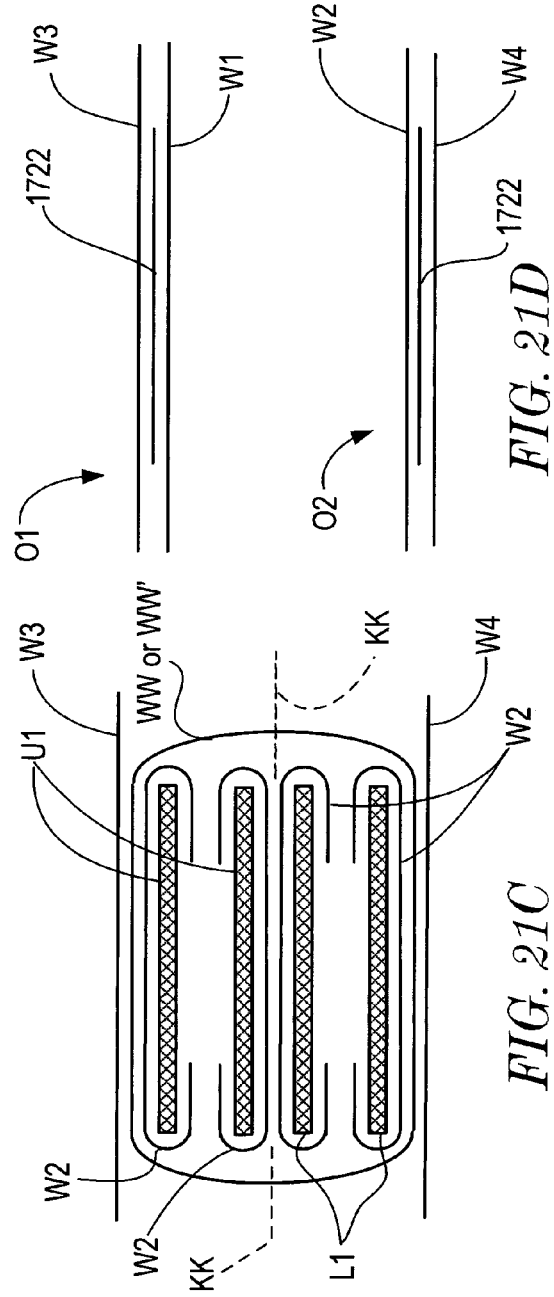
FIG. 21A  FIG. 21B  FIG. 21C  FIG. 21D

ELASTIC COMPOSITE, AND A SYSTEM AND METHOD FOR MAKING THE ELASTIC COMPOSITE

The present application is a Divisional Application of U.S. Utility application Ser. No. 11/475,288, filed on Jun. 26, 2006 (now pending), which is a Continuation-in-Part of U.S. Utility application Ser. No. 11/021,424, filed on Dec. 23, 2004, now U.S. Pat. No. 7,361,246, which application claims the benefit of Provisional Application Ser. No. 60/532,480, filed on Dec. 24, 2003. The above applications are hereby incorporated by reference for all purposes and made a part of the present disclosure.

BACKGROUND OF THE INVENTION

The present invention relates generally to elastic composites. More particularly, the present invention relates to an elastic composite that can be employed in one or more areas of a garment, other textile or fabric structures, similar material structures, and the like. The present invention also relates to a system and method of making the elastic composite and a garment, other textile or fabric structures, and the like, employing the elastic component. The elastic composite and the system and method for making the elastic composite are particularly suited for use with or on disposable absorbent garments or articles such as baby diapers and training pants. To illustrate the invention, exemplary and preferred embodiments described in the context of disposable absorbent garments.

Disposable absorbent garments contemplated by the invention include disposable diapers, disposable pull-on garments, and the like. These garments are worn about the lower torso or waist of the user so as to receive and contain urine and other bodily wastes. The benefits provided by the use of a disposable diaper on an infant are well known and its use has become widespread in the past several decades. Disposable pull-on garments include training pants, pull-on diapers, disposable underwear, and adult incontinence garments. It is generally expected that the user of any one of these garments will be able to put on and take off the garment on his/her own. As for training pants, these garments are used by young children to facilitate the child's transition from using diapers to wearing regular underpants (i.e., during toilet training). Training pants (and other disposable pull-on pants) have closed sides such that the user or caregiver raises the garment about the user's legs to put it on and slips the garment downward about the user's legs to take it off.

The principal elements of a typical disposable absorbent garment include a liquid permeable inner layer (or topsheet), a liquid impermeable outer layer (or backsheet), and an absorbent core sandwiched between the inner and outer layers. Elastic members may be incorporated into different parts of the garment. For example, elastic members may be positioned longitudinally along a diaper, generally outboard of the absorbent core to effect a seal around the buttocks, legs, or both of the users. In addition, several elastic members (e.g., in the form of elongated elastic threads or strands) may be positioned laterally throughout the waist regions (including the side waist regions) of a disposable absorbent garment. The resulting elastication allows the garment to stretch when it is put on and then during wear. In this way, the garment can stretch to accommodate variations in waist size and leg size of the user, while fitting snugly about the waist and legs.

When elastic members are incorporated into a part or area of the garment, that part or area typically becomes a distinct, functional component of the garment. These elastic components include the side panels or ear portions, the waistband, and fastening tabs. The elastic components to which the present invention is directed is generally elongated, and may be a distinct portion of a larger, unitary piece, or a separate, attachable component. Furthermore, the elastic component typically contains one or more sections or layers in addition to the elastic members. In this regard, such an elastic component may be referred to as an elastic composite.

These elastic composites are typically functional components that have an important impact on the fit and sealability of the garment. Due in part to its multi-component construction, these elastic composites typically require a dedicated sub-process for manufacture which must be accommodated by the larger garment manufacturing process. Alternatively, the elastic composite may be manufactured independently and fed into the larger process as a complete product. The design and construction of the elastic composite represents, therefore, a significant portion of the cost of manufacturing a disposable absorbent garment, as well as the quality and utility of the finished product.

It is, therefore, desirable to provide a functionally and/or an aesthetically improved elastic composite and an improved method of making the elastic composite and also system therefor.

SUMMARY OF THE INVENTION

For purposes of the present description, the term "elastic band" or "elastic composite" refers to a multi-layer construction. In this construction, a plurality of elastic members, such as threads or strands, are disposed adjacent one or more layers, e.g., backsheet and topsheet. In this way, the elastic members impart elasticity to the adjacent layers and thus, to that part of the garment or other textile structure. Such an elastic structure may be a distinct attachable component of the garment or textile structure or may be a distinct portion or section of the garment body or textile structure or a larger, unitary component of the garment body or textile structure.

In one aspect of the present invention, a method of making an elastic composite is provided. The method entails conveying a first web of material along a web plane path. The method also entails applying a first section of a first elastic strand onto the first web and generally transversely to the web plane path and applying a second section of a second elastic strand onto the first web and generally transversely to the web plane path. These applying steps are repeated while performing the conveying step, thereby arranging a plurality of first and second elastic elements on the first web, in generally parallel relation to one another. The resultant elastic composite is suitable for incorporation into a disposable absorbent garment and the like.

In another aspect of the invention, a system is provided for making an elastic composite for incorporation into a disposable absorbent garment and the like. The system includes a source of a first web of material, a web conveyor assembly including a first web moving platform for moving the first web thereon along a first web plane path, and a spinning head assembly. The spinning head assembly is provided for applying a section of a first continuous elastic strand and a section of a second continuous elastic strand about the web conveyor assembly and a first web being moved thereon. The spinning head assembly is positioned such that a first web being conveyed on the platform is movable into the path of each of the two sections of elastic strand being spun by the spinning head assembly to apply the two sections thereon.

In another aspect of the present invention, a method of making an elastic composite is provided. The elastic composite is provided for incorporation into a disposable absorbent garment, textile, or fabric structure and the like. The method entails conveying a first web of material in a web plane moving direction and conveying a second web of material in the web plane moving direction. The method further entails applying a section of a continuous strand of elastic element generally linearly onto both the first web and the second web along a direction generally transverse to the web plane moving direction. The applying step may be repeated a plurality of times, thereby arranging a plurality of sections of first and second elastic elements on each of the first web and the second web, in generally parallel relation to one another.

In another aspect of the invention, a system is provided for making an elastic composite for incorporation into a disposable absorbent garment, textile, or fabric structure, and the like. The system includes a web conveyor assembly including a first web moving platform for moving a first web thereon and a second web moving platform for moving a second web thereon. A spinning head assembly is also provided for applying a section of a first continuous elastic strand about the web platforms and a first web and a second web being moved therealong. The spinning head assembly is positioned about the first and second web moving platforms to spin the section of elastic about a plane intersecting the first and second webs moving therealong. The first and second web moving platforms are spaced laterally apart such that the first and second webs are generally coplanar about sections whereupon the intersections between the plane and the first and second webs are located.

In one aspect of the invention, an elastic composite is provided in a disposable absorbent garment such as a diaper or training pants. The elastic composite has a base layer, a top layer, and an elastic construction disposed therebetween. The elastic construction includes a plurality of spaced apart (e.g. preferably generally equally spaced apart) elastic elements (e.g. strands or threads) that are aligned in generally parallel relation. Further, the top and base layers define a first side edge, a second side edge, and a longitudinal centerline therebetween. The elastic construction is disposed between the two layers and extends in a direction that is between the side edges and is generally parallel with or corresponds to (i.e., overlays) the longitudinal centerline. Further, the elastic elements are oriented along a lateral direction that intersects the side edges and longitudinal centerline (e.g., such that each elastic element is oriented or aligned along a direction that is generally perpendicular to the side edges).

Preferably, the elastic composite includes at least one elasticized region, wherein the elastic construction is disposed, that is spaced inwardly from the side edges and, in some embodiments, positioned generally centrally between the side edges. Such an elastic composite also includes a first non-elasticized region disposed between the first side edge and the elasticized region, and a second non-elasticized region disposed between the second side edge and the elasticized region.

In certain embodiments, the first and second non-elasticized regions provide fastening regions that are generally flat relative to the elastic regions, and may be equipped with a fastening element such as adhesives or a hook or loop element. More preferably, the elastic elements are attached to at least one of the top and base layers such that the elasticized region is shirred when the elastic composite is disposed in a relaxed, un-stretched state. In further embodiments, a second elasticized region is provided between the side edges and a third non-elasticized region is provided between the first and second elasticized regions.

In preferred embodiments, the elastic construction has a centerline extending therethrough that is spaced generally equidistantly from each side edge and the elastic strands are distributed along this centerline and in generally perpendicular relation therewith. Preferably, the direction of this centerline corresponds with a machine direction of the elastic composite band or more specifically, the web material from which the elastic composite band is cut.

In yet another aspect of the invention, a disposable absorbent garment is provided with a topsheet, a backsheet, and an absorbent core disposed between the topsheet and the backsheet and such that a longitudinal centerline of the garment extends through the topsheet, backsheet, and absorbent core. Together, the topsheet, backsheet, and absorbent core provide a central body of the disposable absorbent garment. The inventive garment further includes an elastic composite band that is attached to the central body. The elastic composite band has a first side edge, a second side edge, and a composite centerline extending in between the side edges. The elastic composite band includes a base layer, a top layer, and an elastic construction disposed between the top and base layers and spaced inwardly from each side edge. The elastic construction includes a plurality of spaced apart elastic elements that are distributed in a direction extending between the side edges and each aligned in generally perpendicular relation with the composite centerline.

Preferably, the elastic composite band includes an elasticized region that is positioned generally centrally between the first and second side edges, and wherein the elasticized region is disposed. The elastic composite also has a first non-elasticized region positioned between the first side edge and the elasticized region, and a second non-elasticized region positioned between the second side edge and the elasticized region. In some embodiments, the elastic composite band is attached adjacent an end of the garment leg (e.g., along a waistline) and provides therealong an elastic waistband on the garment. In further embodiments, the garment has two elastic composite bands each attached along a side margin of the garment. In these embodiments, the elastic composite band provides an elastic waist fastening portion of the diaper, such as an elastic side panel or ear portion of the garment or elastic fastening tab. In one particular embodiment, the elastic composite is provided as the central chassis or central body of the garment.

The present invention also relates to a system and a method for making the elastic composite and/or the garment incorporating the elastic composite.

In one aspect of the present invention, a method is provided for making an elastic composite. The elastic composite is made for incorporation into a disposable absorbent garment. The method includes the step of providing an elastic element applicator configured to move a section of a continuous strand of elastic element generally about a plane. A first web of material (e.g., non-woven material) is conveyed in a web moving direction such that the first web intersects the plane. Then, the elastic element applicator is operated to move the elastic element about the plane, thereby applying the section of elastic element onto the first web along a direction generally transverse to the web moving direction. Preferably, the elastic element is applied such that the section of elastic element is retained by the first web and the first web draws the continuous elastic strand from the elastic element applicator as the first web is conveyed away from the plane. More preferably, the elastic element applicator is a spin cylinder or bracket, that is operated to spin the elastic element about the moving first web, thereby applying the elastic element on the first web.

In another aspect of the present invention, another method is provided for making an elastic composite for incorporation into a disposable absorbent garment. The method includes the step of conveying a first web of material and folding each of the side edges of the first web along a side fold line and inwardly toward an inward surface of the first web. This creates a pair of folded flaps adjacent the inward surface and an exposed outward surface having a width defined between the fold lines (i.e., at the folded side edges). A plurality of spaced apart elastic strands is subsequently applied across the width of the exposed outward surface. Then, the applied elastic strands are cut proximate each of the fold lines of the first web (i.e., along the folded side edges), such that the lengths of the elastic strands are generally equal to the width of the outward surface. Thereafter, the folded flaps of the first web are unfolded such that the resulting first web has, applied thereon, a plurality of centrally located elastic strands and non-elasticized side regions defined generally outward of the fold lines. Preferably, the elastic strands are applied in spaced apart, generally parallel relation. Furthermore, the elastic strands are preferably applied by spinning a continuous elastic strand about the first web.

BRIEF DESCRIPTION OF THE DRAWINGS

FIG. 19A is a top view of a system for making an elastic composite, according to an embodiment of the present invention;

FIG. 19B is a side view of the system in FIG. 19A;

FIG. 20A is a top view of a system for making an elastic composite, according to an alternative embodiment of the invention;

FIG. 20B is a side view of the system in FIG. 20A;

FIG. 21A is a cross-sectional view through line AA in FIG. 19B;

FIG. 21B is a cross-sectional view through line BB in FIG. 19B;

FIG. 21C is a cross-sectional view through line CC in FIG. 19B;

FIG. 21D is a cross-sectional view through a web output of elastic composite, according to the present invention;

DETAILED DESCRIPTION OF THE INVENTION

Figure 1:
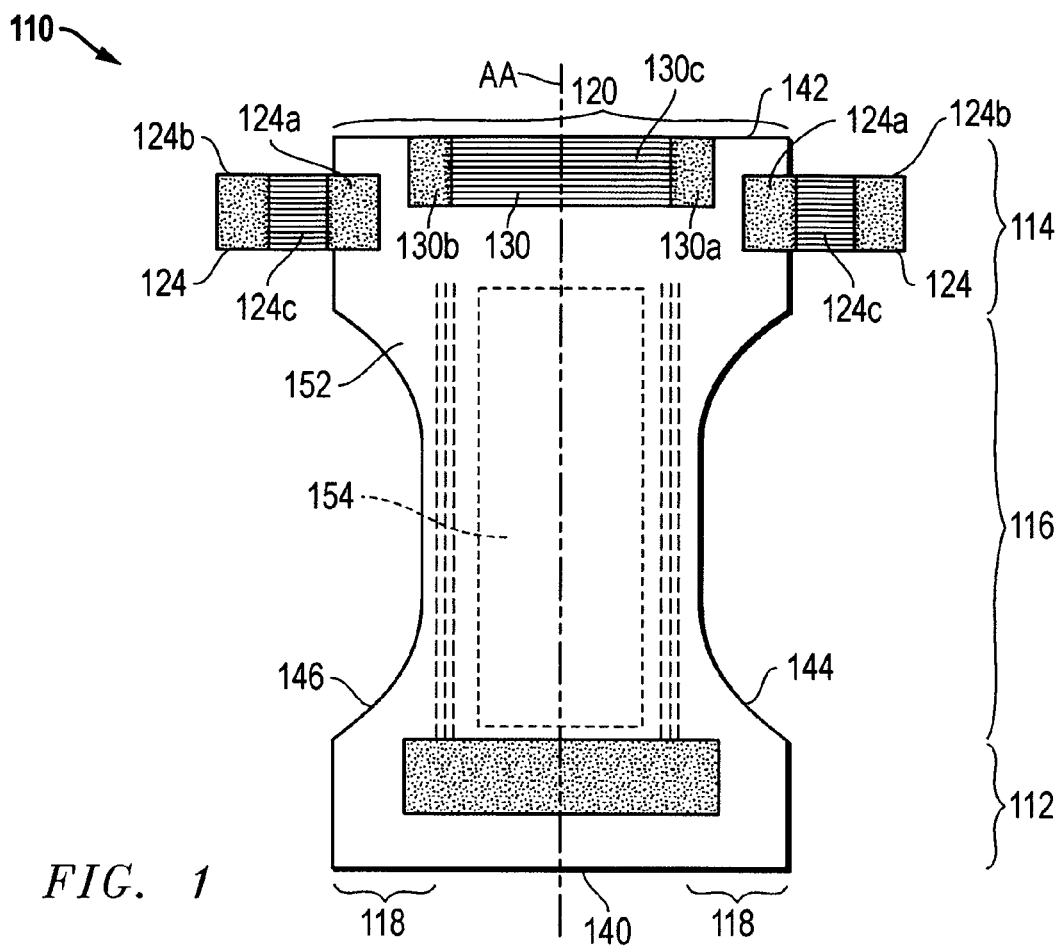
FIG. 1 is a plan view of a disposable absorbent garment in the unfolded configuration; according to the present invention.

Each of FIGS. 1 and 4-9 depict a disposable absorbent garment embodying various aspects of a first described invention. More particularly, each of these Figures depict such a garment that incorporates an elastic composite structure or elastic composite in accordance with that invention. In FIG. 1, a disposable absorbent garment 110 is shown that is suitable for the invention and in the form of a diaper having one or more elastic composites incorporated therein. The elastic composite in FIGS. 1-8 have side and end edges and, thus, may be referred to herein as elastic composite bands. FIGS. 9-16 illustrate a system and process of making the elastic composite (and a garment having the elastic composite) in accordance with another described invention.

FIGS. 17-20 and 29-30 are now provided to illustrate another method or process of making an elastic composite (and a garment having the elastic composite), and a system for making or manufacturing the elastic composite, in accordance with the present invention. These figures also embody various aspects of the present invention in the form a novel elastic composite, a web output of the elastic composite, and/or a material structure, such as a disposable absorbent garment, textile or fabric structure, similar material structures, and the like, and into which the elastic composite is incorporated. The described system and process are particularly focused on the application or integration of the elastic elements upon or with one of the layers of the composite.

FIGS. 21-28 are also provided to illustrate yet another method or process of making an elastic composite (and a garment having the elastic composite), and a system for making or manufacturing the elastic composite, in accordance with an alternative embodiment of the present invention. These figures also embody various aspects of the present invention in the form a novel elastic composite, a web output of the elastic composite, and/or a material structure, such as a disposable absorbent garment, textile or fabric structure, and he like, into which the elastic composite is incorporated. The described system and process are particularly focused on the application or integration of the elastic elements upon or with one of the layers of the composite.

As described previously, various aspects of the present invention are particularly suited to or for a disposable absorbent garment, such as baby diapers and training pants. To illustrate the invention and preferred embodiments of the invention, much of the following Detail Description will be provided in the context of such disposable absorbent garments. It is contemplated that various aspects of the inventive composite, garment, system, and process may be applicable to other material structures and processes. This Detailed Description and exemplary embodiment should not, therefore, be construed as limiting the invention to the structures, configurations, methods, and processes described herein.

The disposable absorbent garment 110 in FIG. 1 is of a type that can be placed against or in proximity to the body of a wearer so as to absorb and to contain various bodily exudates. It should be noted, however, that the present invention is applicable to a variety of disposable absorbent articles and garments, including training pants and a variety of adult incontinence products. As will be described below, the inventive elastic composite or elastic composite band may provide a side panel or ear portion, a waistband, a fastening tab or band, or other distinct elastic component of the garment or article. The inventive elastic composite may also be incorporated into an ear portion to elasticate the ear portion or to supplement the ear portion with an elasticated fastening tab. Accordingly, the present invention is not intended to be limited to the structures and the processes specifically described and illustrated herein. For purposes of description, however, the following discussion will be directed to an exemplary disposable diaper only. Moreover, the invention will be described in the context of its various configurations and aspects. It should be appreciated that alternative arrangements of the inventive disposable absorbent garment and such an elastic composite band may comprise various combinations, which include one or more of the various configurations and aspects of the invention.

FIG. 1 is introduced to illustrate some basic features of a disposable diaper 110, most of which are also applicable to other disposable absorbent garments contemplated by the invention. The diaper 110 includes three main regions aligned along an imaginary longitudinal axis or plane AA. These regions include a first waist region 112 (typically at the front of the user when the garment 110 is worn), a back waist region 114, and a crotch region 116. The diaper 110 is also characterized by a front edge 140, a back longitudinal edge 142, a first lateral or side edge or side margin 144, and a second lateral or side edge or side margin 146.

Along a lateral direction, the diaper 110 includes ear regions or ear portions 118 extending laterally from the waist regions 112, 114. Together, the waist regions 112, 114 and crotch region 116 may be referred to as forming a central body portion 120 of the garment 110 that is positioned within side edges 144, 146. The body portion 120 may also be referred to as being formed by a liquid permeable inner layer or topsheet 152, a liquid impermeable outer layer or backsheet (not shown), and an absorbent core 154 sandwiched between the two layers. The ear portions 118 further include fastening tabs 124 for attaching the waist regions 112, 114 together. The diaper 110 also has an elastic waistband 130 positioned generally along the back edge 142 to facilitate fastening and to enhance the fit and seal of the diaper 110. When the hourglass shaped diaper 110 is worn, the crotch region 116 fits about the crotch of the wearer, and the front and back waist regions, 112 and 114, fit about the corresponding waist areas. The ear portions 118, on the other hand, wrap about the wearer and the fastening tabs 124 engage to form a complete, all-around waistline of the diaper 110.

Figure 2A:
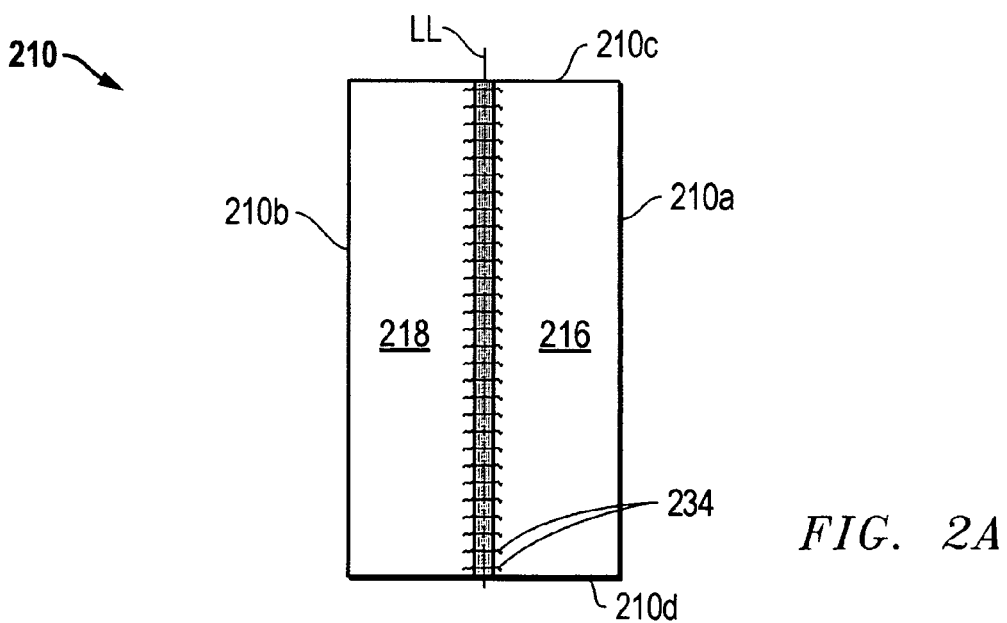
FIG. 2A is a plan view of an elastic composite according to the present invention.
Figure 3:
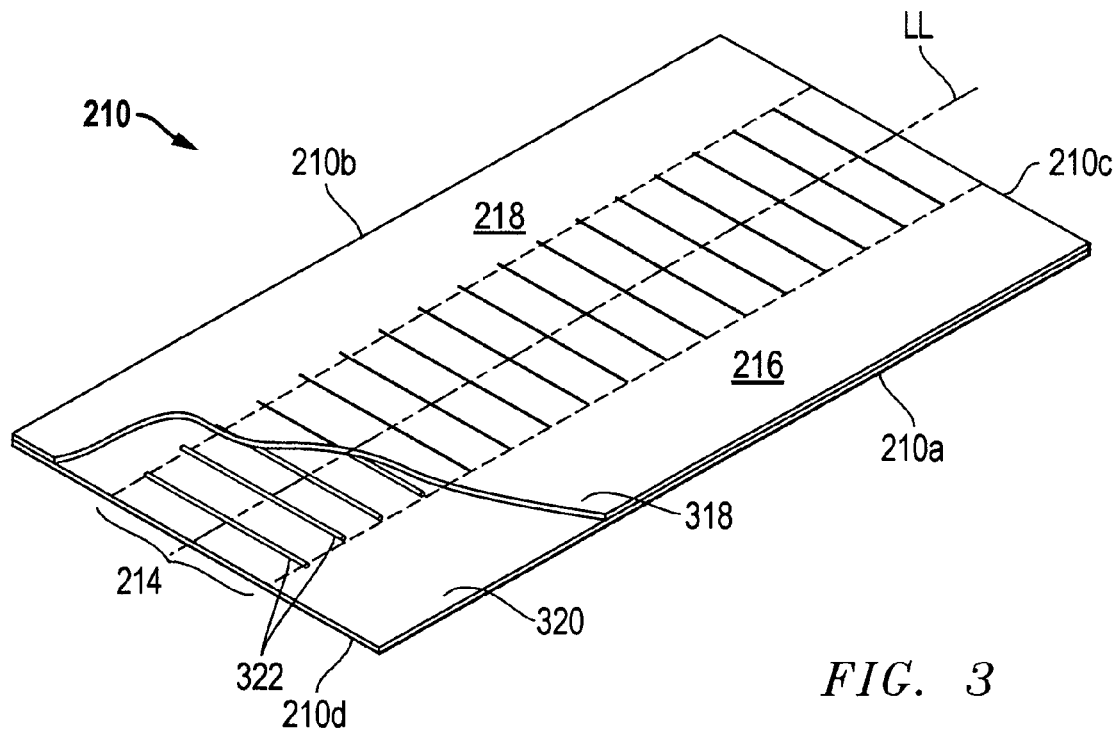
FIG. 3 is a perspective view of the elastic composite of FIG. 2A with a cut-out detail to show an elastic construction.

FIG. 2A depicts a typical elastic composite band 210 according to the invention. More particularly, the elastic composite band 210 is one particularly suited for use as a side panel or fastening tab of a disposable absorbent garment (see, e.g., FIG. 1). FIG. 3 provides a perspective view and partial cut-out of the elastic composite band 210. The elastic composite band 210 may be characterized by an imaginary centerline LL. In one aspect of the invention, the centerline LL preferably corresponds with the machine direction of the elastic composite band 210 during manufacture. The elastic band 210 also has side or longitudinally extending side edges 210a and 210b and laterally extending end edges 210c and 210d. In FIG. 1, the elastic composite band 210 is shown in the stretched state as, for example, when a garment incorporating the elastic composite band 210 is worn. In this state, the elastic composite band 210 stretches, in the lateral or cross-machine direction (denoted by arrows XX).

As used herein, the term "machine" direction refers to the direction at which the component, or more particularly, the material web from which the elastic composite is derived (e.g., cut from) is driven in an assembly line during manufacturing. The term "cross-directional machine direction" or "cross-directional," on the other hand, refers to the direction that is perpendicular to the machine direction. With reference to the elastic composite 20 of FIG. 2, the cross machine direction is the direction XX extending laterally or perpendicularly relative to the longitudinal line LL.

The elastic composite band 210, according to the invention, has a central region 214 in which an elastic construction is situated. Extending laterally from this central elastic or elasticized region 214 are regions 216 and 218, which are substantially non-elasticized. As shown in FIG. 2A, the regions 216, 218 occupy the expanse between the central elastic region 214 and the side edges 210a, 210b. Now with reference to FIG. 3, the elastic composite band 210 has a top layer 318 and a bottom or base layer 320. The two layers 318, 320 preferably extend the total width and length of the elastic composite band 210, thereby providing the side edges 210a, 210b, and the end edges 210c, 210d. Both the base layer 320 and the top layer 318 are preferably a non-woven, breathable, disposable material such as propylene, non-woven fabric, breathable polyethylene/polypropylene films, or non-porous films (or combinations of these materials). The base layer 320 and top layer 318 adhere to one another, thereby sandwiching and securing a plurality of elastic strands 322 therebetween.

The elastic strands 322 may be substituted, in alternative embodiments, by suitable elastic elements such as elastic strands, threads, ribbons, and elastic glue beads. In one aspect of the invention, the elastic elements or strands 322 are distributed along a direction that extend between the side edges 210a, 210b and parallel with (or corresponding to) center line LL. Further, each elastic element 322 is generally aligned or oriented in a direction corresponding with the lateral or cross-machine direction, i.e., in a direction generally perpendicular to the longitudinal center line LL and intersecting the side edges 210a, 210b. Preferably, the strands 322 are disposed in generally parallel relation and spaced apart generally equally along the longitudinal direction. More preferably, the elastic strands 322 are of generally equal length. Accordingly, when the elastic composite band 210 is worn, the strands 322 impart elasticity into the structure which allows the band 210 to stretch in the lateral or cross-machine direction XX.

Figure 2B:
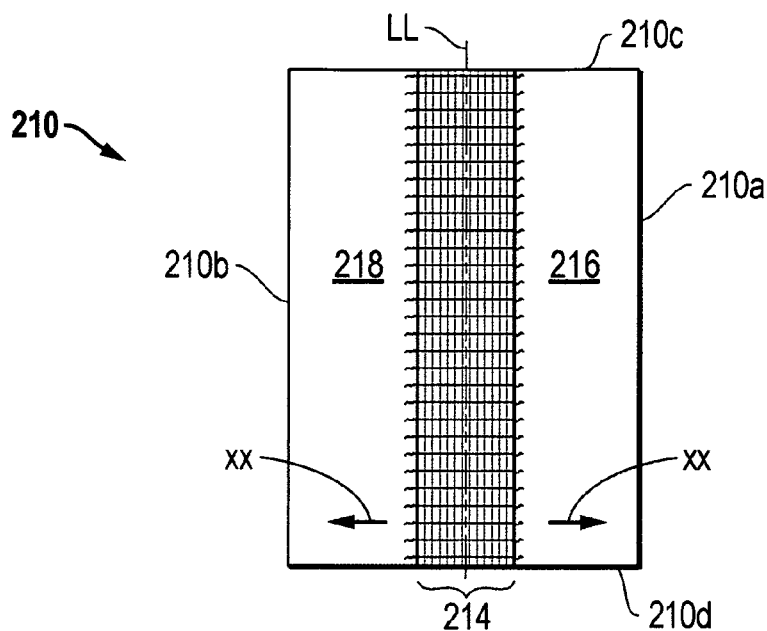
FIG. 2B is a plan view of the elastic composite of FIG. 2A shown in an extended, stretchable condition.

The elastic strands 322 are preferably tensioned during securement between the top and base layers 318, 320. FIG. 2B illustrates the elastic composite band 210 in a laterally stretched condition. In this condition, the central elastic region 214 has a width that is almost equal to the non-elasticized zones 216 and 218. When returned to the non-laterally stretched or relaxed condition, as shown in FIG. 2A, the central elastic region 214 contracts and crimps to a substantially reduced width. In this condition or state, the contracted elastic strands 322 shirrs the elastic composite 210 and provide pleats 234 in the contracted elastic region 214.

The elastic composite band 210 may originate from a web of material that is wound onto spools or festooned. Typically, the user of such material will cut the material to a length required of a particular application. In some applications, one such web of material may provide the source of multiple components of the inventive disposable absorbent garment.

Returning to FIG. 1, the inventive disposable absorbent garment 110 employs one or more elastic composite bands according to the invention, as described above. The disposable absorbent garment 110 employs in each of the ear portions 118, a fastening tab 124 having the inventive elastic composite construction. As the fastening tab 124, the elastic composite band is configured such that one non-elasticized region 124a is attached to and overlaps the central body 120 of the garment 110 while a second non-elasticized region 124b is situated outboard of the side margins 144, 146. An elasticized region 124c, as shown in FIG. 1, provides elasticity, and thus, stretch in the lateral or cross-machine direction (of the elastic composite). In respect to the rest of the garment 110, the elasticity or stretch provided by the central elastic region 124c directed along a direction that is generally perpendicular to the longitudinal center line AA of the garment 110, and corresponds with a direction that wraps about the waistline of the user.

The disposable absorbent garment 110 in FIG. 1 also provides an elastic composite, according to the invention, as the waistband 130. The waistband 130 is situated centrally in the waist region 114. Further, the elastic composite waistband 130 is disposed such that non-elasticized regions 130a, 130b are positioned outwardly of the longitudinal line AA of the garment 110, while an elasticized region 130c is positioned centrally across the longitudinal center line AA. Moreover, the elasticized region 130c is configured such that the elastic strands are aligned or oriented in a direction that is generally perpendicular to the longitudinal center line AA. In this way, the elastic composite waistband 130 imparts elasticity about the waist region 114 of the garment 110, and in a direction corresponding with the direction of waistline about the user.

Figure 4:
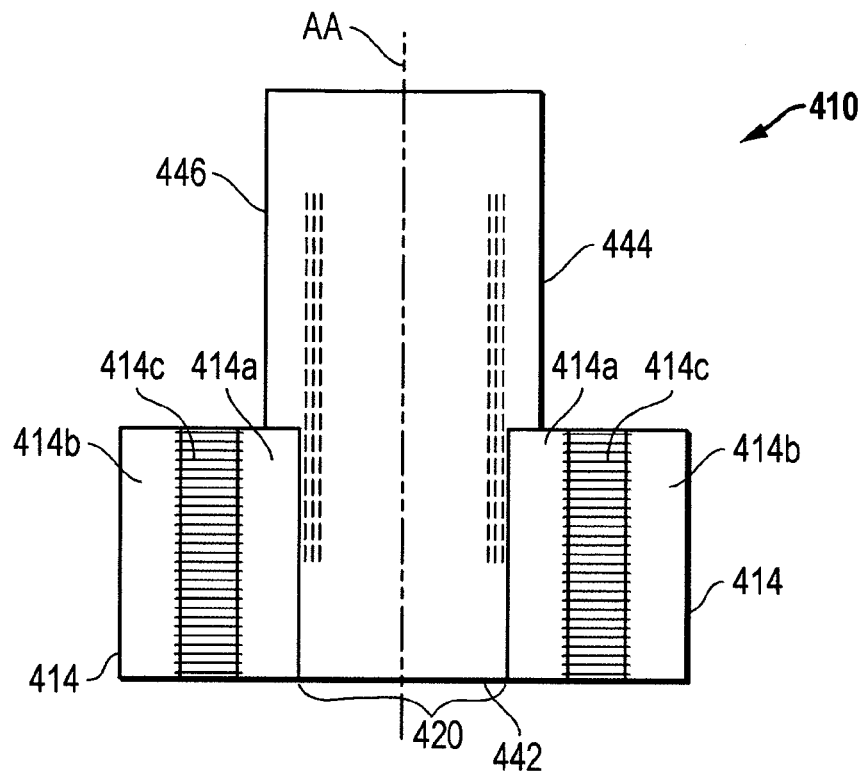
FIG. 4 is a plan view of an alternative disposable absorbent garment according to the invention.

FIG. 4 depicts an alternative disposable absorbent garment 410 according to the invention. Specifically, FIG. 4 depicts a disposable absorbent garment 410 employing elastic composites according to the invention as attachable ear portions or side panels 414. The elastic composite side panels 414 are separate components that are attached to a central body 420 of the garment 410. The elastic composite side panels (or ear portions) 414 are attached near one waist edge 442 of the garment 410 and such that the centerline AA of the side panel 414 is generally parallel with the longitudinal centerline AA of the garment 410. Moreover, each of the elastic composite side panels 414 has a non-elasticized region 414a that is positioned outboard of the side margins 446 of the garment 410 and a second non-elasticized region 414b that is attached inboard of the side margin 446 (or side margin 444). Thus, a central elastic region 414c is situated outboard of the side margin 446 and not directly attached thereto. When the garment 410 is in use, the central elasticized region 414a allows the side panel to stretch in a lateral or cross-machine direction that corresponds with the lateral direction relative to the longitudinal centerline AA of the garment 410. Accordingly, when the garment 410 is worn, the elastic side panel 414 allows for stretching about the waistline of the user.

Figure 5:
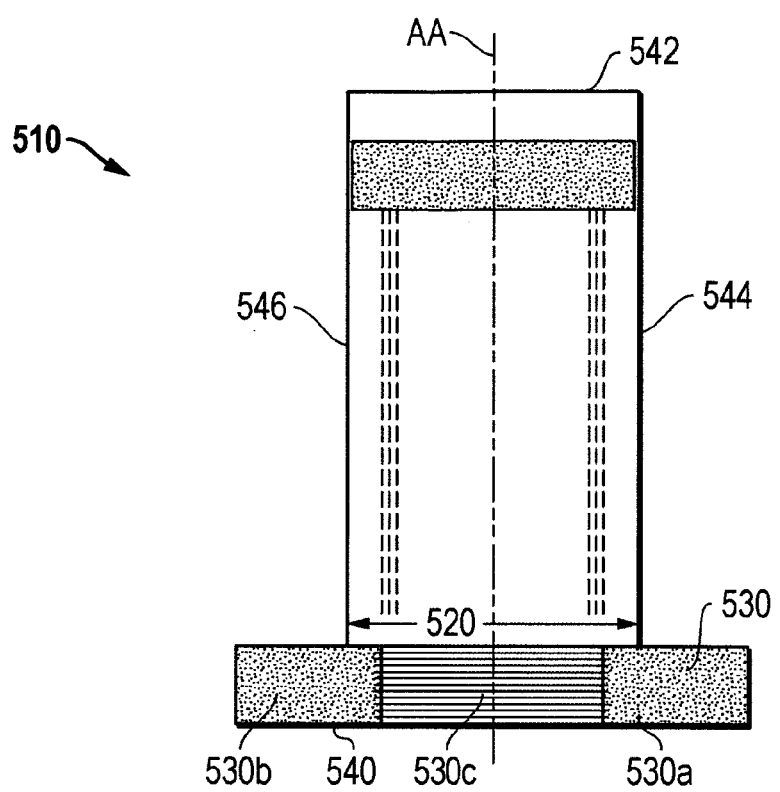
FIG. 5 is a plan view of another alternative disposable absorbent garment, according to the invention, incorporating an elastic composite as a waistband.

FIG. 5 depicts yet another alternative embodiment of a disposable absorbent garment 510 according to the invention. The disposable absorbent garment 510 is a diaper partially defined by end or waist edges 540, 542 (not shown) and side margins 544, 546. Further, the inventive disposable garment 510 has a central body 520 and a separate, attachable elastic waistband 530. Similar to the garments 110, 410 in FIGS. 1 and 4, respectively, the garment 510 employs an elastic composite, as the elastic waistband 530. The inventive elastic waistband 530 is attached adjacent a waist edge 542 of the garment 510 and is positioned centrally about the longitudinal centerline AA. The elastic composite waistband 530 is situated such that non-elasticized regions 530a, 530c extend laterally past the side margins 544, 546, respectively. The central elasticized region 530c is positioned centrally within the central body 520 and side margins 544, 546. The elastic strands of the central elastic region 530c is further situated such that the elastic region 530c provides elasticity or stretch in a lateral direction relative to longitudinal centerline AA. Again, in this way, the elastic composite waistband 530 according to the invention allows for the garment to fit snugly and effectively about the waistline of the user.

Figure 6:
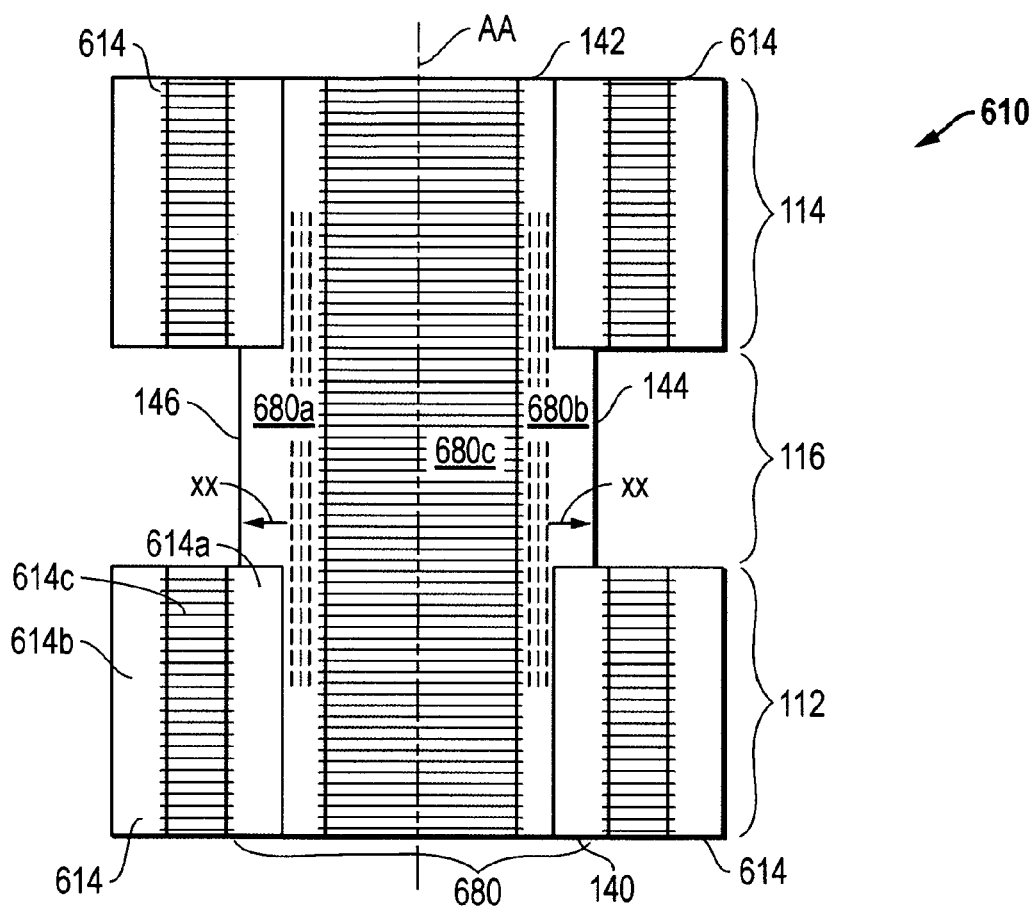
FIG. 6 is a plan view of yet another alternative disposable absorbent garment, according to the invention, further incorporating an elastic composite as a central body chassis.

FIG. 6 illustrates an alternative disposable absorbent garment 610, according to the invention (wherein like reference numerals are used to indicated like elements), in which the inventive elastic composite band is incorporated into various areas or as various garment components. The garment 610 has a front waist region 112, a back waist region 114, and a crotch region 116 positioned therebetween. As with the garment 410 of FIG. 4, an elasticized composite band 614 is attached to each side margin 144, 146, near end edge 140, as an elasticized side panel 614. A second pair of elastic composite bands is attached as an elasticized side panel 660 along the opposite end edge 42 of the garment 610.

FIG. 6 also illustrates the use of the inventive elastic composite band to provide an elasticized central body or chassis 680 at or beneath the crotch region 116 of the garment 610 and in support of an absorbent core (not shown so as to clearly display the chassis 680). The absorbent core is preferably adhered to and movable with the elasticized chassis 680. Thus, the core is preferably a conformable (changes shape in accordance with an outside force), elastic, or extensible (e.g., pulled and permanently stretched) body, as is generally known in the art. In this way, the main or central body of the garment 610 is elasticized in a lateral direction XX that is generally perpendicular to a longitudinal centerline AA of the garment 610. In the garment 610 of FIG. 6, the inventive composite band provides the entire length of the central body or chassis 680. The elastic composite chassis 680 has an elasticized region 680c situated between two non-elasticized regions 680a, 680b. Preferably, the elasticized region 680c provides an elastic construction of a plurality of elastic strands as disclosed previously in respect to the embodiments of FIGS. 1-5. In the illustrated embodiment, the elasticized region 680c extends between end edges 140, 142, thereby imparting lateral elasticity (stretchability) across the entire garment length.

Figure 4A:
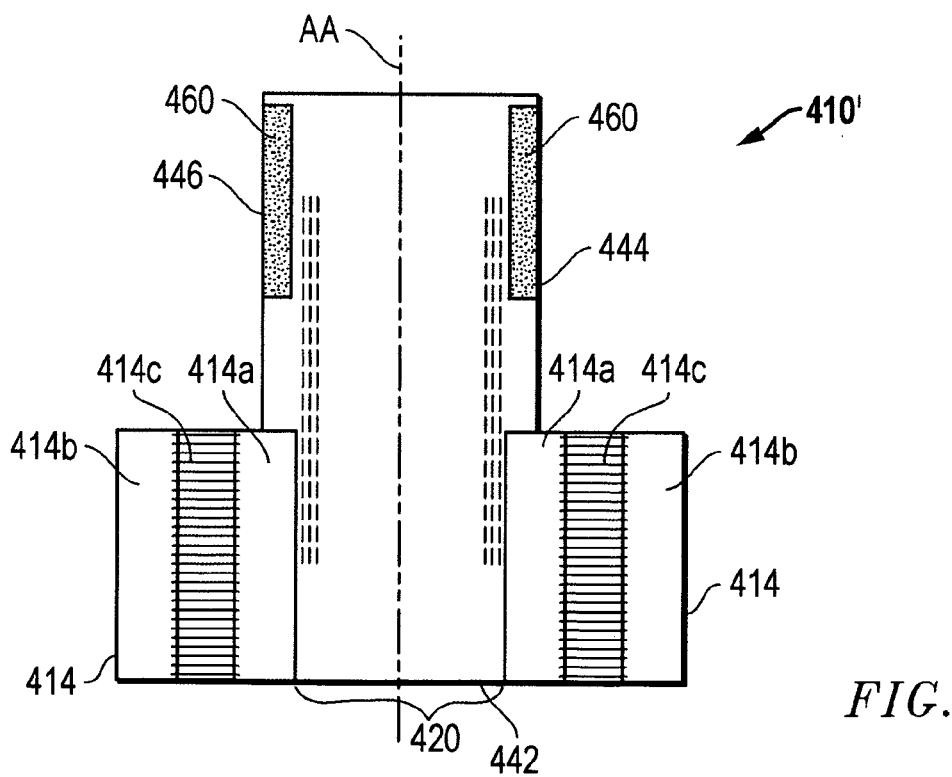
FIG. 4A is a plan view of a convertible or converted disposable absorbent garment according to the invention.

Now turning to FIG. 4A, the disposable absorbent garment 410' is provided with fastening means 460 along the margins 444, 446, and near one end opposite of the elastic composite side panels 414. Provision of the fastening means 460 allows for fastening of the ends of the garment. Accordingly, this particular garment 410 is referred to as a convertible or converted garment, in that it allows the garment to be used as a diaper and alternatively, as a training pants type garment.

The fastening means 460 may be provided with fastening elements such as hooks or loops which can correspondingly adhere or attach to the non-elasticized zones 414a, 414b of the side panels 414. The garment 410' may come with the fastening means 460 attached with the side panels 414, in the way of a training pant. Furthermore, the fasteners 460 may be detached from the side panel 414, in the way of a diaper.

Figure 6A:
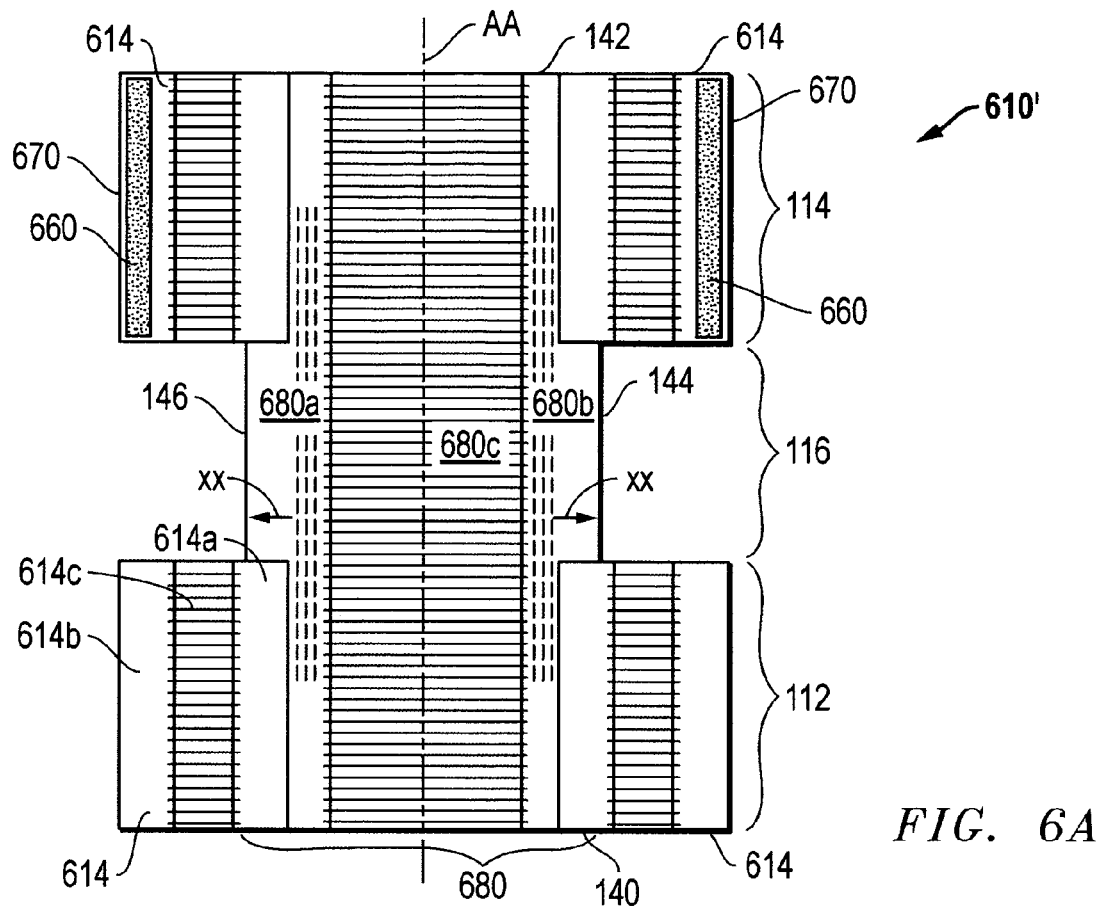
FIG. 6A is a plan view of a convertible or converted disposable absorbent garment according to the invention.

Now turning to FIG. 6A, the disposable absorbent garment 610' is also provided with fastening means 660 on the elastic composite side panel 614. The fastening means 660 may include fastening elements such as hooks or loops, which can adhere and attach to the non-elasticized zone 614a, 614b of corresponding side panel 614.

Figure 7:
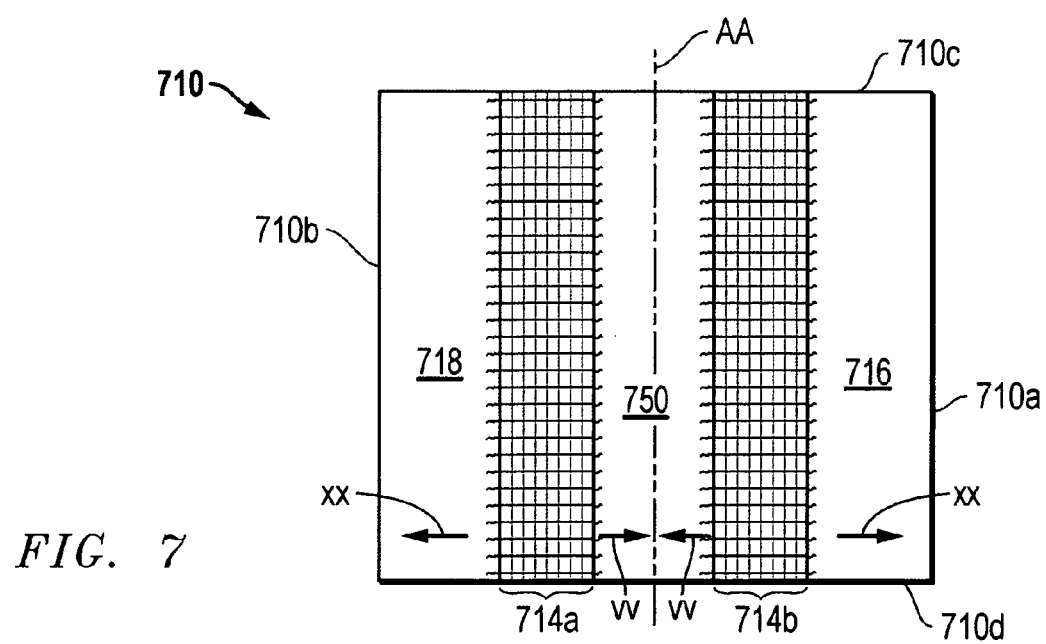
FIG. 7 is a plan view of an alternative elastic composite according to the present invention.

FIG. 7 depicts an alternative embodiment of an elastic composite band according to the present invention. The elastic composite band 710 illustrated therein differs from the previously described elastic composite band (see e.g. FIGS. 2 and 2a) in that the elastic composite band 710 includes two elasticized regions 714a and 714b. The elasticized region 714a, 714b are preferably equidistantly spaced apart on either side of the longitudinal centerline AA. The spacing of the elasticized regions 714a, 714b creates right and left non-elasticized or dead regions 716, 718, as well as central non-elasticized region 750. The elasticized regions 714a, 714b imparts elasticity to elastic composite band 710a in the lateral directions XX, and in the central non-elasticized region 750, also in the opposite lateral direction VV.

Figure 8:
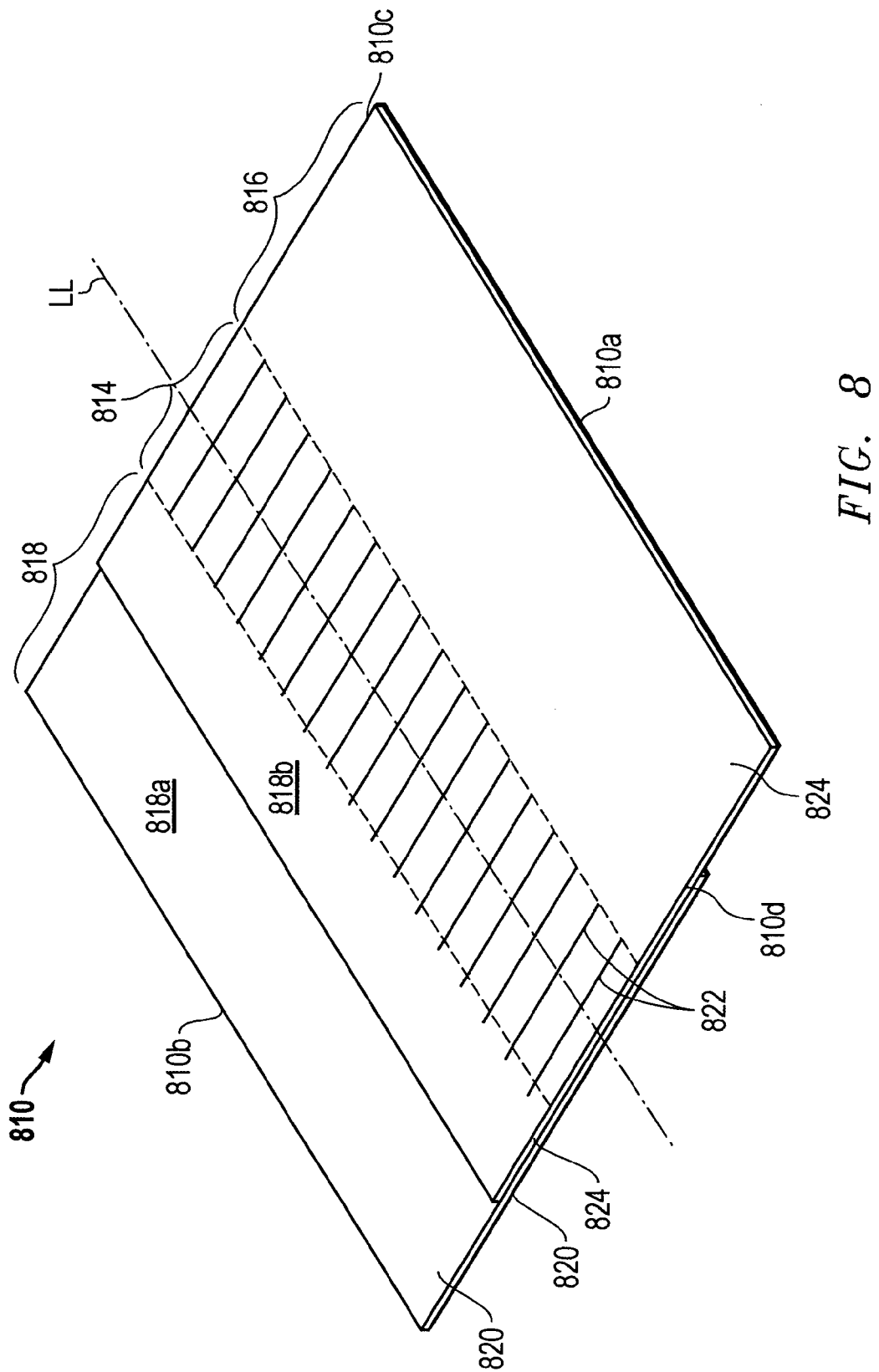
FIG. 8 is a perspective view of yet another alternative elastic composite according to the invention.

FIG. 8 depicts yet another embodiment of an elastic composite band 810 according to the invention. The inventive elastic composite band 810 has, as in previously described embodiments, a central elastic or elasticized region 814 and regions 816 and 818 that are substantially nonelasticized and extend laterally from the central elasticized region 814. The elasticized region 814 is again comprised of a plurality of elastic strands 322 that are disposed in generally parallel relation, and generally perpendicular with a longitudinal centerline LL of the elastic composite band 810 (and the elasticized region 814). The elastic composite band 810 also has end side edges 810a, 810b, and end edges 810c, 810d.

In yet another aspect of the invention, the elastic composite band 810 is further comprised of base layer 820 and top layer 824. As shown in FIG. 8, base and top layers 820, 824 sandwich the elastic strands 822 therebetween. In contrast to previously described embodiments, layers 820 and 824 are offset in respect to one another. Specifically, the two layers 820, 824 are not positioned squarely or evenly one atop another, but overlap. In this way, the elastic composite band 810 is made wider. In particular, by offsetting the two layers 820, 824, the nonelasticized regions 816, 818 are extended and may be referred to as having an outside section (e.g., 818a) formed by one of the layers 820, 824 and an inside section (e.g., 818b) having both a top and a bottom layer 820, 824. Preferably, the two layers 820, 824 are two plies of nonwoven material. The wider nonelasticized, nonwoven regions 816, 818 provide a working area on which fastening materials and other accessories or structural attributes of the disposable absorbent garment may be situated. In various embodiments, the offset or overlap of the two layers 820, 824 may be varied so as to create nonelasticized regions 816, 818 of various widths. Moreover, a wider elastic composite band (and specifically, nonelasticized regions of the elastic composite band) is attained, without increasing the size of the nonwoven layers.

Figure 8A:
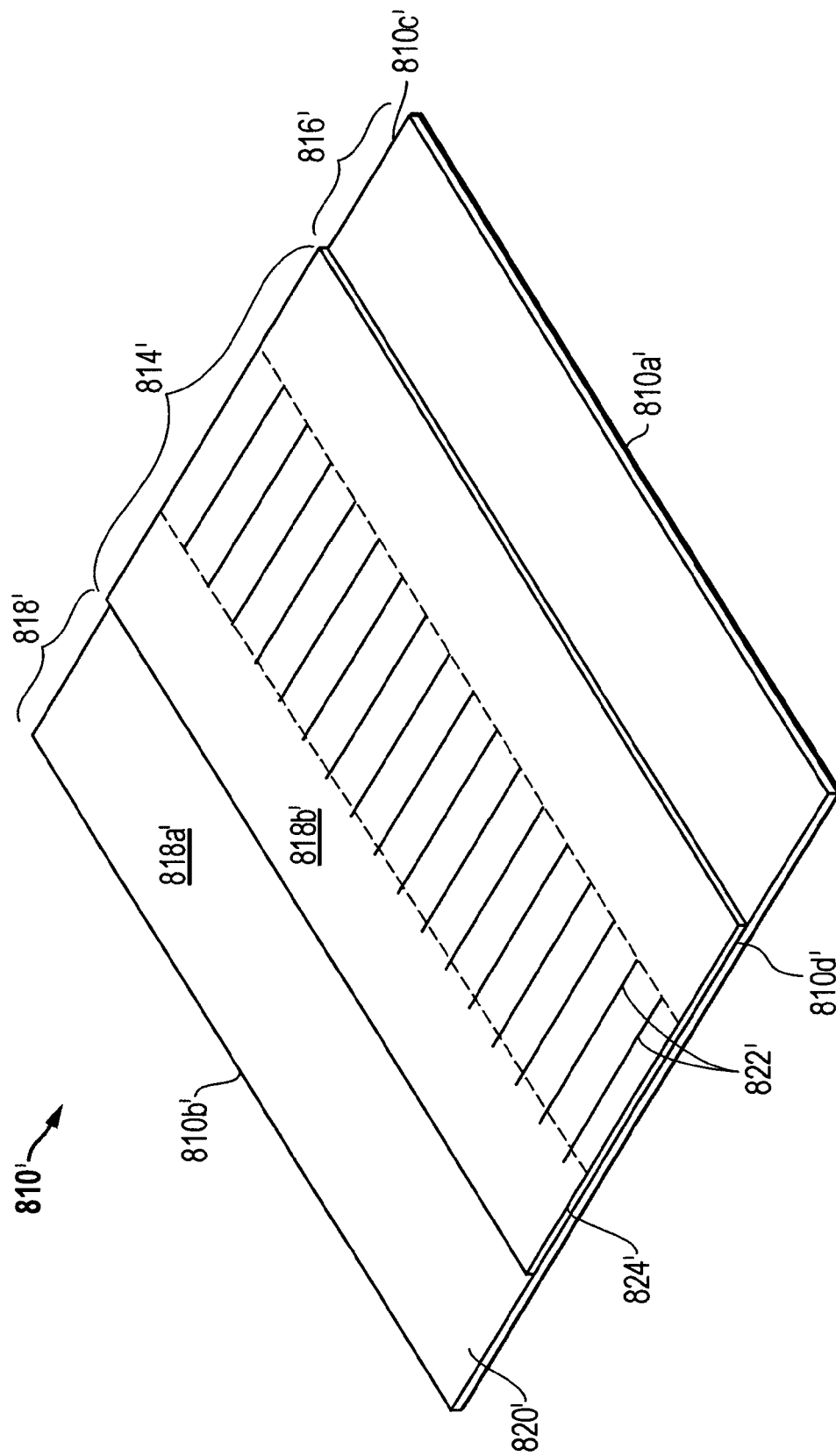
FIG. 8A is a perspective view of yet another alternative elastic composite according to the invention.

FIG. 8A illustrates a further variation of the elastic composite band 810 in FIG. 8, in accordance with the present invention. Specifically, FIG. 8 depicts an inventive elastic composite band 810' having a central elastic or elasticized region 814' and regions 816' and 818' that are substantially nonelasticized ("dead zones") and extend laterally from the central elasticized region 814'. The elasticized region 814' is again comprises of a plurality of elastic strands 822' that are disposed in generally parallel relation and generally perpendicular with a longitudinal centerline LL of the elastic composite band 810' (and the elasticized region 814').

In this particular embodiment of the invention, the elastic composite band 810' includes a base layer 820' and a top layer 824' that is significantly narrower than the base layer 820'. The base and top layers 820' and 824' sandwich the elastic strands 822' therebetween. Preferably, the width of the top layer 824' is no less than 5 mm wider than the width of the central elasticized region 814'. This design further illustrates yet another aspect of the invention, and a manufacturing process, which results in a reduction of the raw material costs of the disposable absorbent garment, and more specifically, the elastic composite band 810'.

Figure 9A:
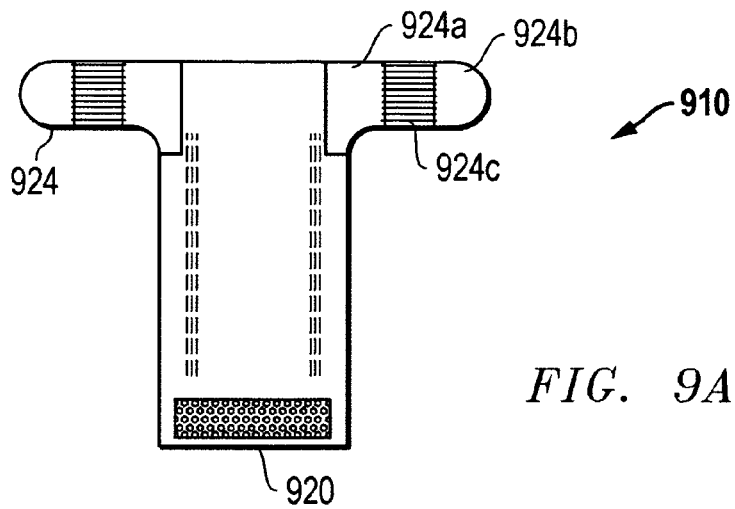
FIGS. 9A-9C are plan view of a further alternative disposable absorbent garments, according to the invention.
Figure 9B:
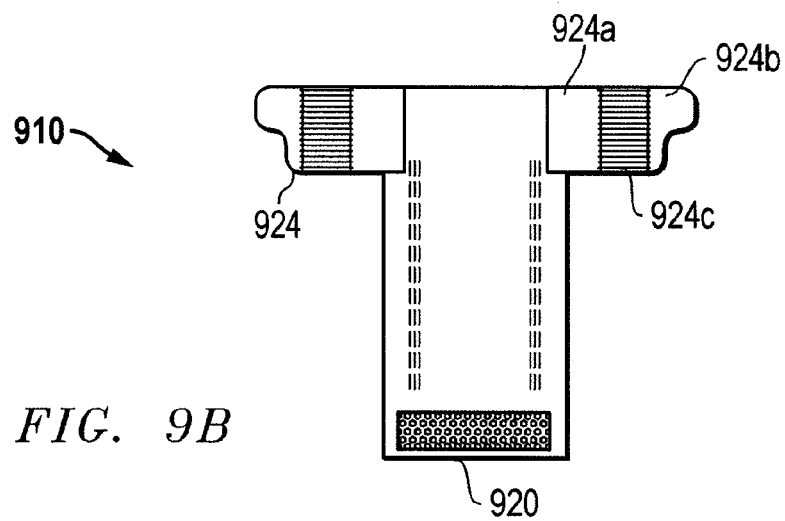
Figure 9C:
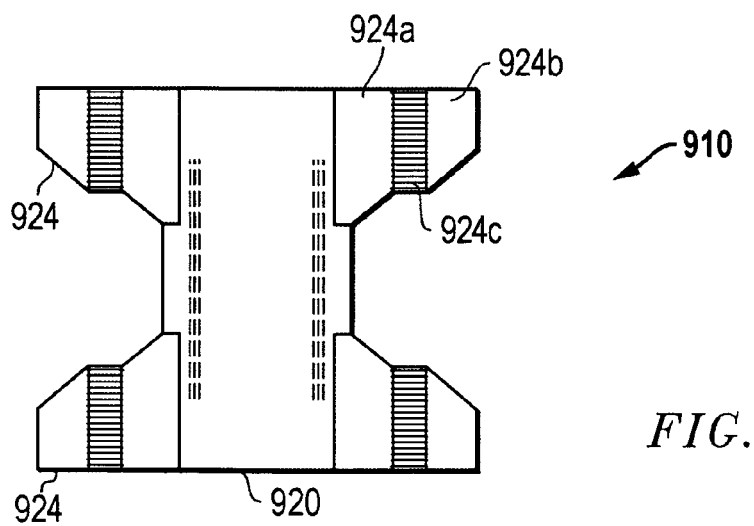

FIGS. 9A-9C are provided to illustrate further embodiments of the present invention. More specifically, FIGS. 9A-9C provide alternate designs, specifically alternate shapes, of the inventive elastic composite band. In these figures, like elements are referenced using like numerals.

Referring to FIGS. 9A and 9B, a disposable absorbent garment 910 is shown having a central body 920 and elastic composite bands in the form of ears or side panels 924. The ears 924 have inner and outer nonelasticized regions 924a, 924b, and a central elasticized region 924c situated therebetween. These two figures illustrate an elastic composite band according to the invention having nonelasticized regions 924a and 924b that are different from one another and do not provide side edges of the elastic composite band 924 which are in generally parallel relation. In both designs, the side edge of the outer nonelasticized regions 924b are rounded or curved. The shape of the elastic composite bands 924 in these two figures provide, among other advantages, a more attractive product as perceived by the consumer.

Now turning to FIG. 9c, yet another variation of the elastic composite band 924 is shown applied to a training pants 910. Specifically, the inventive elastic composite band 924 has nonelasticized regions 924a and 924b of different geometries. This design of the elastic composite bands 924 provide an aesthetic as well as a functional advantage. The functional advantage comes in the form of an improved fit around the wearer's leg, particularly due to the shape of the elastic composite band 924.

FIGS. 10-16 depict a system and system components, and illustrate a method or process of making or manufacturing the elastic composite according to one embodiment of the invention. In one aspect of the inventive process, two elastic composite web outputs 1031 are produced from four separate non-woven web inputs 1003a, 1003b, 1003c, and 1003d. To facilitate the description of the present invention, reference may be made to U.S. Pat. Nos. 3,627,621 and 2,902,395, each of which discloses certain features of the prior art system and process for manufacturing a lamination and/or composite having non-woven materials. Each of these patents is hereby incorporated by reference and made a part of the present disclosure. In particular, reference may be made to certain basic components of a system or apparatus for manipulating non-woven materials and fibers.

Figure 10:
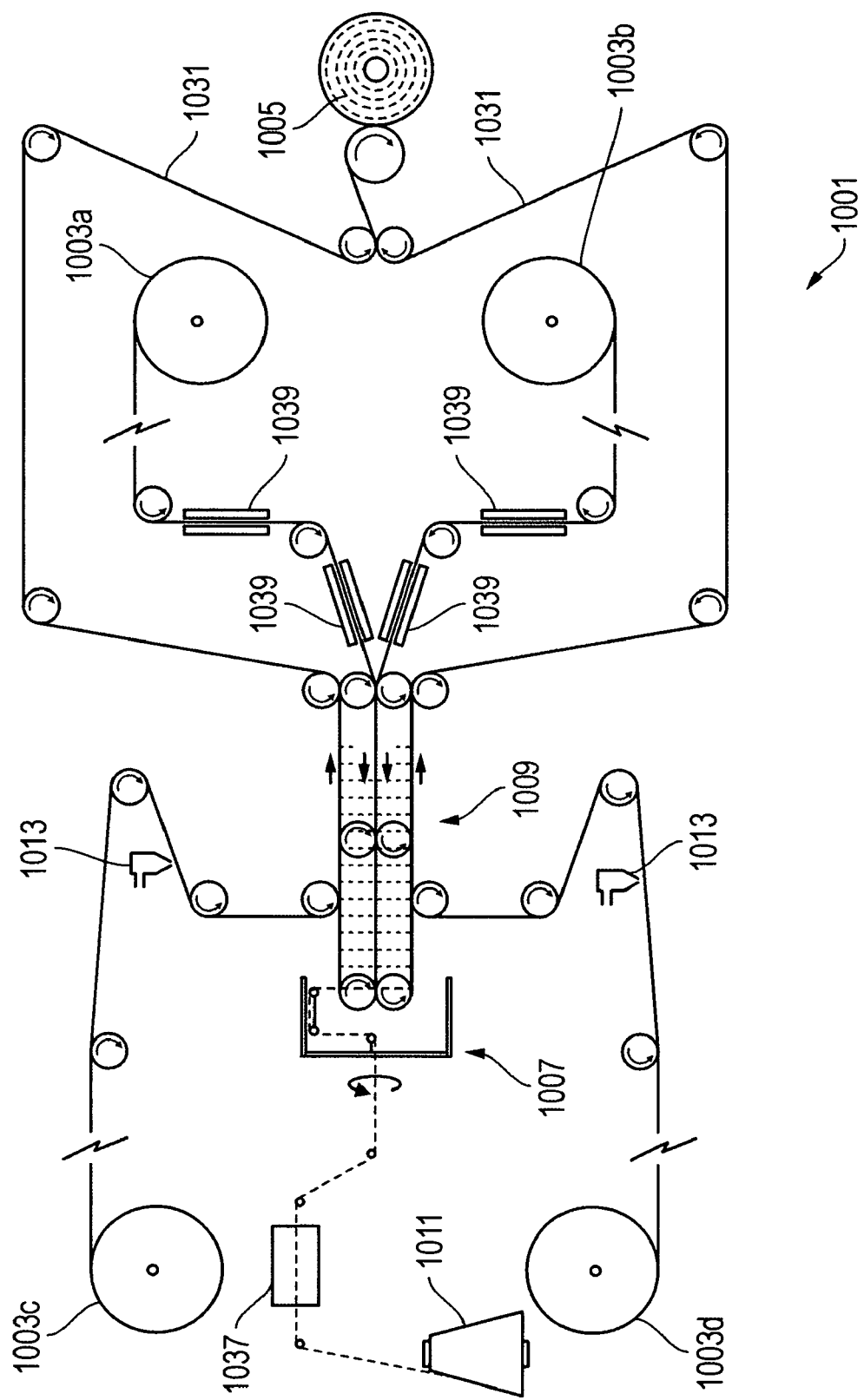
FIG. 10 is a simplified schematic of a system for manufacturing the elastic composite according to the present invention.

Referring first to FIG. 10, a system 1001, according to the invention, includes four separate non-woven web inputs 1003a-1003d, which provide a web or roll of non-woven material for the elastic composite. The system further includes an output assembly or reel 1005 that receives two elastic composite webs 1031 from the rest of the process. These two separate elastic webs may be fixed together to produce the kind of composite described in respect to FIG. 7 (or maintained separately).

Central to the inventive system 1001 are a conveyor assembly 1009 for receiving, manipulating, and conveying each of the non-woven web inputs. The conveyor assembly 1009 is positioned and operatively associated with an elastic element applicator such as a spinning head assembly 1007, that applies elastic fibers or strands upon, onto, and or integrally with the non-woven web inputs. The spinning head assembly 1007 further includes a spin head 1017, preferably in the form of a spinning bracket, or cylinder 1017 and the like. The spin cylinder 1017 is configured to hold an "end section" of the continuous strand WW of elastic and move it about a generally vertical plane XX in a reciprocal or repetitive pattern (relative to the conveyor assembly 1009). This plane XX is defined by the area within the spinning perimeter of the cylinder 1017 and which is traced by the outer most bracket or eye 1017b securing the strand of elastic WW to the spin cylinder 1017. The paths of the spinning head 1017 and the section of elastic strand retained thereby are provided on the plane XX.

As shown in the schematic of FIG. 10, nonwoven inputs 1003a and 1003b are fed, utilizing a series of rollers, into the conveyor assembly 1009. Before the two nonwoven webs are fed into the conveyor assembly 1009, the webs are directed through the folding guides or plates 1039. The folding guides 1039 serve to effectively reduce the overall width of the nonwoven web by folding the lateral or side edges along a pre-determined, longitudinally-extending side fold line YY. The first folding guide 1039a initiates the first 90° turn while the second folding guide 1039b initiates a second 90° turn. The roller 1039 disposed in between the guide 1039a, 1039b facilitates the folding process. The two folding guides 1039 and roller 1369 may be referred together as a folding guide assembly.

Figure 16:
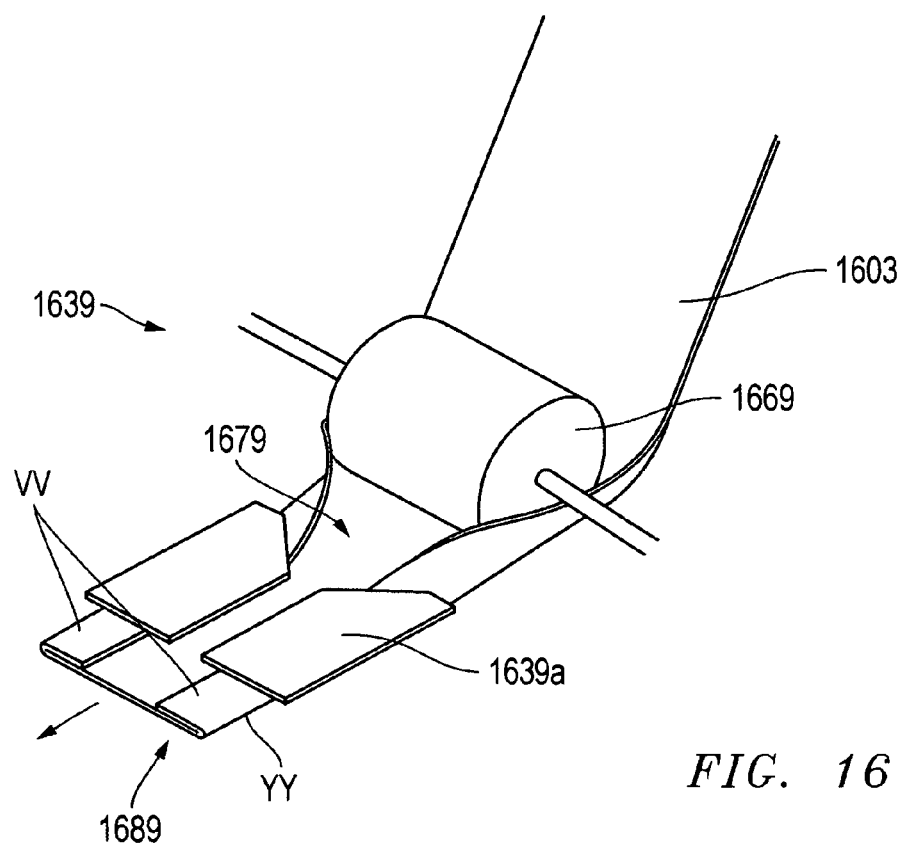
FIG. 16 is a simplified illustration of a folding guide assembly for use with the system and method according to the invention.

FIG. 16 illustrates yet another typical folding guide assembly. The folding assembly 1639 includes folding plates 1639 and a roller 1669 upstream of the folding plates 1639. A web 1603 is passed around the narrow roller 1669, whereby the width of roller 1669 helps determine the width of the web 1603 between the folded flaps VV (i.e., the width of exposed outward surface 1689 defined between the fold lines YY). The width of the roller 1669 is substantially less than the width of the nonwoven web 1603. As a result, the edges of the nonwoven web 1603 list and curl up around the sides of the roller 1669, thereby initiating the folding process. The flat plates 1639 then helps to complete the fold and hold the folded sides down. Another folding guide (not shown) may be provided in a position upstream of the folding roller 1669 to help guide or initiate the folding process.

For purposed of the present Description, the inward surface 1679 is the surface or side of the web 1603 toward which the folded flaps VV are turned. The exposed outward surface 1689 is the surface opposite of the inward surface 1679.

The conveyor assembly 1009 is set up so as to guide these two nonwoven webs 1003a and 1003b through the center of the assembly 1009 towards and eventually inside the elastic spin cylinder 1007 (into the spinning path). Once inside the spin cylinder 1017 the conveyor assembly 1009 delivers the nonwoven webs to each outside, upper and lower faces (outward faces) of the conveyor assembly 1009. At this point the direction of travel of the nonwoven webs are reversed and the webs are directed out of the spin cylinder 1007. As the nonwoven webs exit the spin cylinder 1017, an elastic strand WW is wrapped around the entire conveyor assembly 1009, and as it contacts the upper and lower face of the web platforms it comes into contact with the nonwoven web. As shown in several of the Figures, the elastic strand WW is applied crosswise or laterally on the web, and transverse to the direction of the moving web. The friction between the tensioned elastic strand and the nonwoven webs on the upper and lower faces of the conveyor assembly draws the "wrapped" elastic strand out of the spin cylinder 1017 and towards contact with two further nonwoven webs 1003c and 1003d.

The nonwoven webs 1003c and 1003d are operatively positioned upstream of an adhesive applicator 1013. Utilizing a system of rollers in conjunction therewith, the non-woven inputs 1003c, 1003d and adhesive applicators 1013 apply a web of pre-glued non-woven material onto the conveyor assembly 1009 and onto the elastic strand "wrapped" around the nonwoven webs 1003a and 1003b.

Furthermore, the system 1001 employs a standard elastic input source, e.g., a bobbin of elastic yarn, that feeds elastic strands or fibers WW onto a tensioning/speed controlling unit 1037 and then to the spin cylinder or the spinning head 1017, so as to apply the strands WW onto the conveyor assembly 1009 and the non-woven material webs conveyed therethrough. Elastic is taken off the bobbin, box or positive drive system and fed through a tension and speed controlling motor towards the spin cylinder 1017. The elastic WW is delivered through a hollow shaft in the motor controlling the spin cylinder 1017. The elastic WW then passes into the spin cylinder 1017 and is guided by rollers, eyes or any other suitable mechanism around the inside face of the spin cylinder 1017.

In alternative embodiments of the invention, the above components may be positioned differently in respect to one another, and may employ other standard components not discussed herein. Moreover, the system and process illustrated may be readily integrated into or with one of several known systems and processes for manufacturing disposable absorbent articles and garments. Such integration will be apparent to one skilled in the relevant consumer product or other relevant art, upon reading and viewing the present disclosure.

Figure 11:
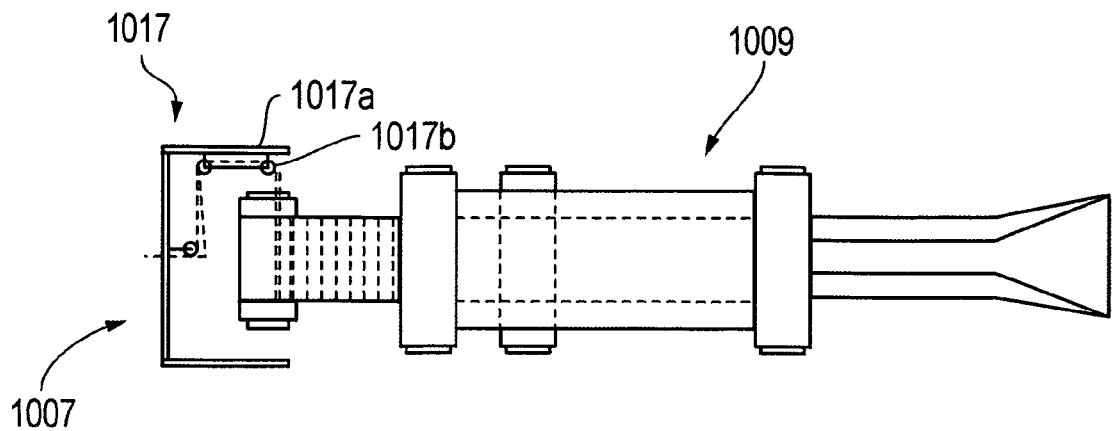
FIG. 11 is a top view of an elastic element applicator assembly for use with the system of FIG. 10.
Figure 12:
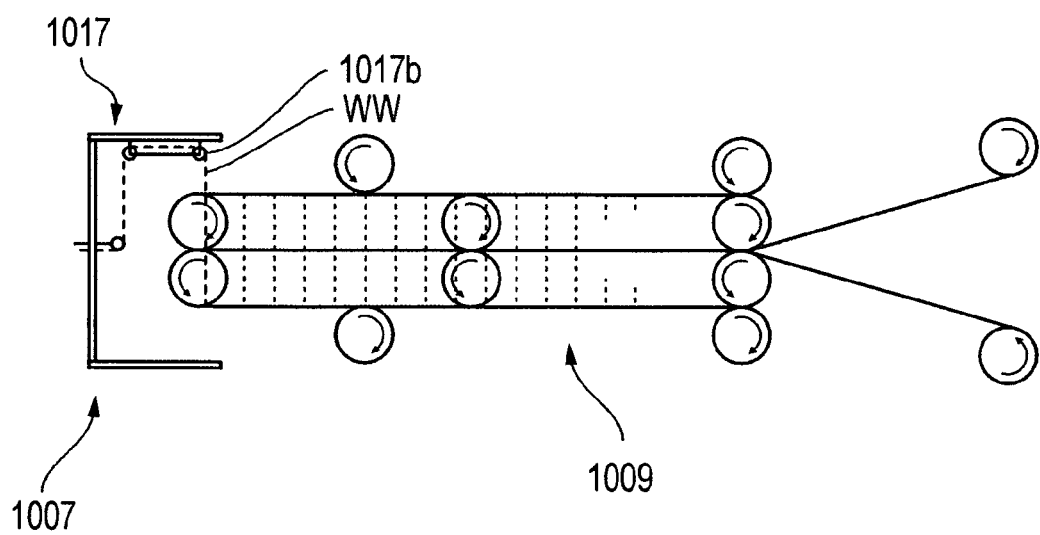
FIG. 12 is a side view of the assembly of FIG. 11.
Figure 13:
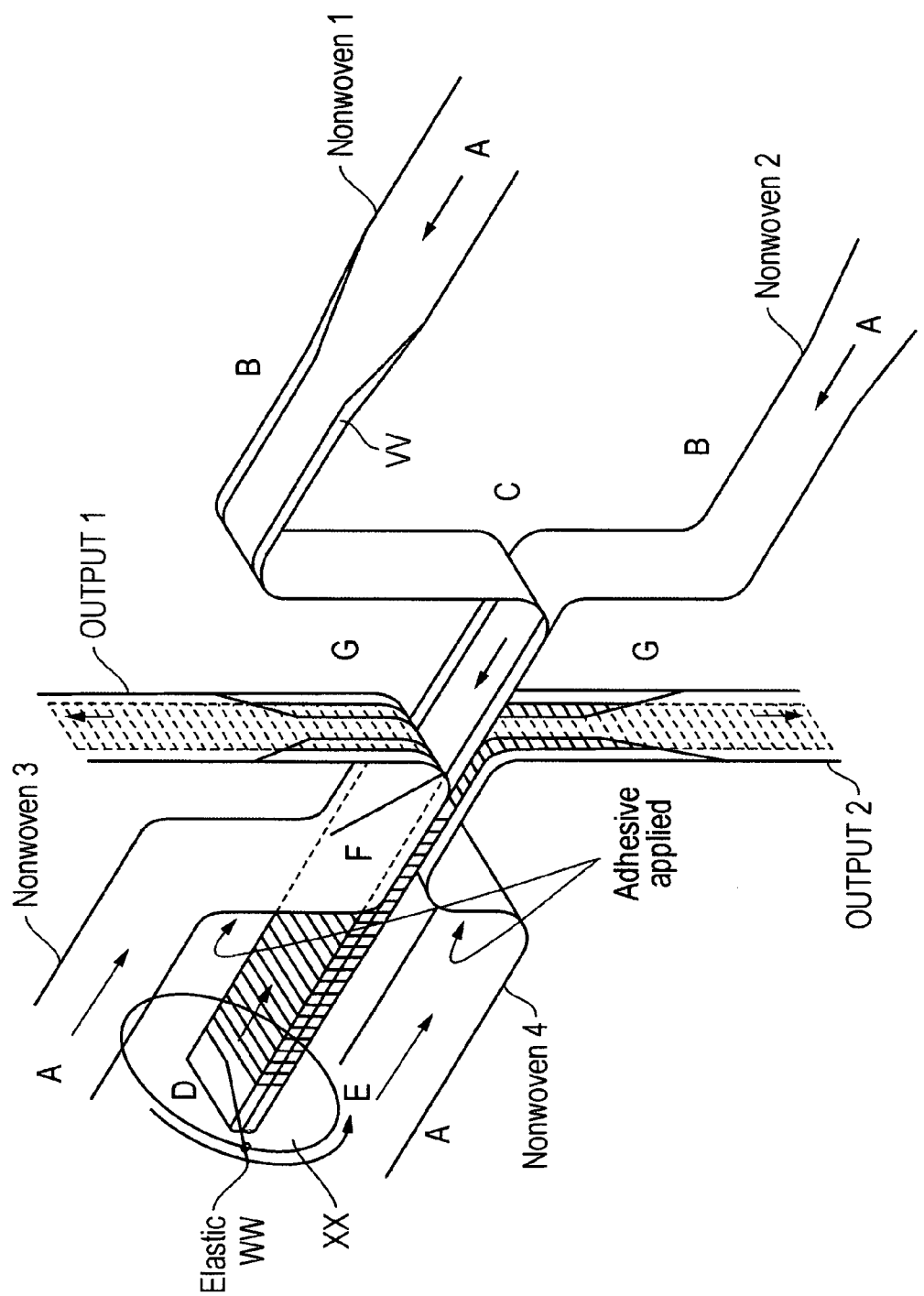
FIG. 13 is a simplified process illustration of making the elastic composite according to the invention.
Figure 14:
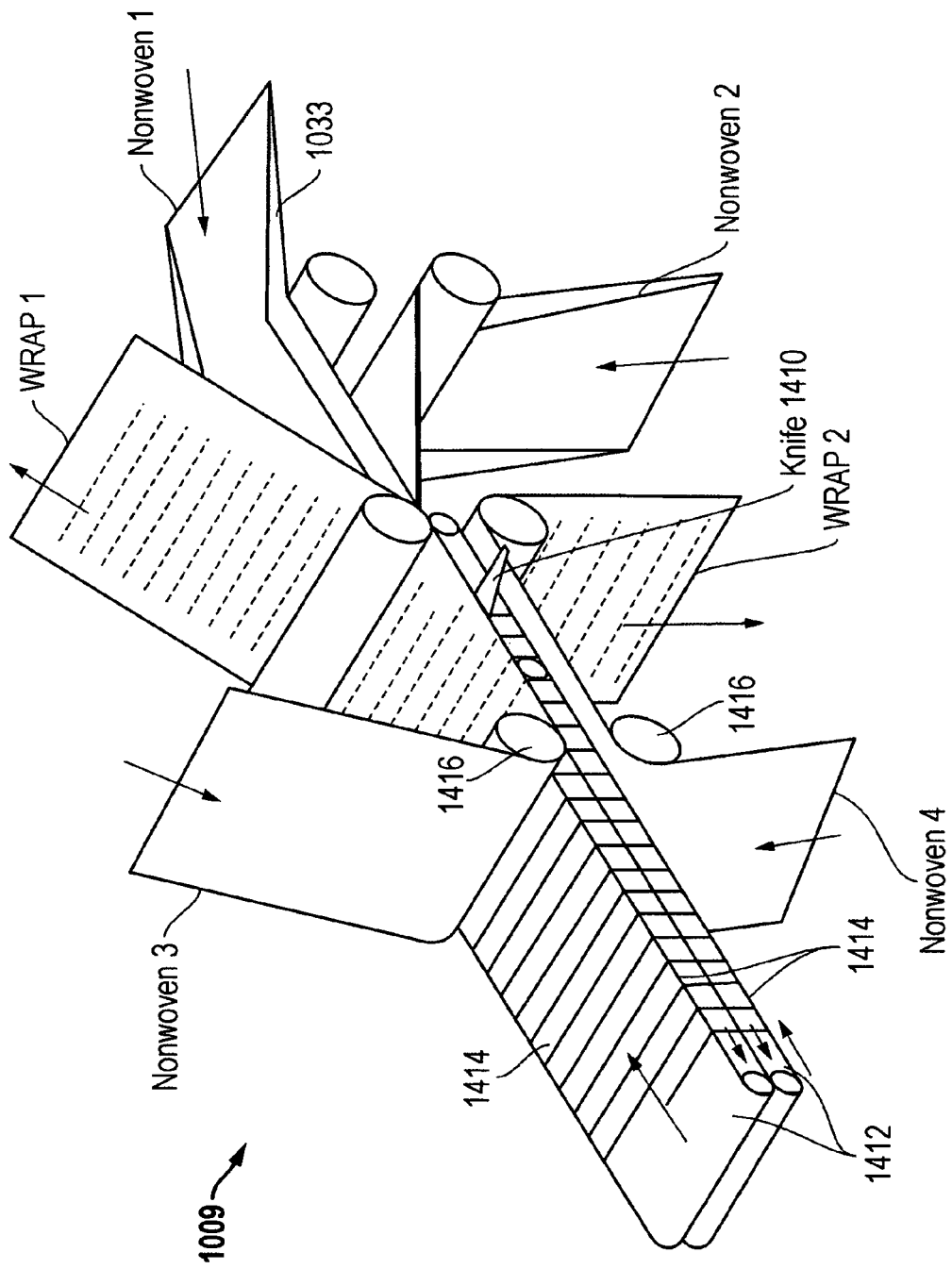
FIG. 14 is a detail view of a conveyor assembly for the system of FIG. 1 according to the invention.

FIGS. 11 and 12 provide alternate views of the spinning head assembly 1007 and conveyor assembly 1009. As discussed above, the conveyor assembly 1009 receives four separate webs of non-woven materials and outputs two webs 1031 of elastic composite. FIGS. 13 and 14 are provided to further illustrate the process of making the elastic composite according to the invention. These figures, more particularly FIG. 13, illustrates the paths taken by the non-woven web materials to and from the conveyor assembly 1009.

Referring to FIG. 13, reference letters A-G are used to refer to stages in the process and in conjunction with the description of the process. As discussed above, non-woven raw material webs are fed into the process at stage A. These webs provide four separate non-woven web inputs into the process. Non-woven webs 1 and 3 are combined to make an elastic composite output 1 (i.e., referred to in the Figures as the WRAP output). Non-wovens 2 and 4, which are both on the downside of the spinning head assembly 1007 and conveyor assembly 1009, combine to make a second elastic composite output 2 (i.e., WRAP 2).

At stage B, non-woven webs 1 and 2 are folded prior to being directed to the conveyor assembly 1009. A predetermined width of non-woven is folded over each side of the web to make two folded flaps VV. The width of the flap VV determines the width of the dead zone or non-elasticized region described previously, while the width of the non-woven, after folding, determines the width of the elasticized region. At stage C, the non-woven webs 1 and 2 are fed into the conveyor assembly 1009, in particular into the middle or inside of the conveyor assembly 1009 with the folded side of each web facing the outside of or away from the conveyor assembly 1009. It should be noted that at this stage C, non-woven webs 1 and 2 are not bonded together. The conveyor 1009 then feeds the non-woven webs 1 and 2 towards the spinning head assembly 1007. At stage D, the non-woven webs 1 and 2 have traveled almost the length of the conveyor assembly 1009 and progresses into the spinning path of spinning head assembly 1007 and intersecting the "spinning" vertical plane XX of the elastic strand WW. Further, at the end of the conveyor assembly 1009, the webs 1 and 2 are directed away from each other and onto the outside of the conveyor 1009 and away from the spinning head 1007. Non-woven web 1 turns up on the upper side of the conveyor assembly 1009, while non-woven web 2 travels along the lower side of the conveyor assembly 1009. At stage E, an elastic strand WW is wound around the folded non-woven webs 1 and 2, as these webs pass through the spinning head and the vertical plane XX. The elastic strand WW is applied to the moving webs 1 and 2 cross-directionally to the direction of the moving web. The movements of the webs 1 and 2 away from within the spin cylinder 1017 draws the "wrapped" elastic strand out of the spin cylinder 1017.

Now turning to non-woven webs 3 and 4, these webs are provided to the conveyor assembly 1009 with adhesive applied on one side (i.e., applied by the adhesive applicator 1013). At stage F, the non-woven webs 3 and 4 are brought into contact with webs 1 and 2, respectively, and the elastic strands WW. As a result, the webs 1 and 3 sandwich elastic strands WW on the upper side of the conveyor assembly 1009, and non-woven webs 2 and 4 sandwich elastic strands WW on the under side of the conveyor assembly 1009. The elastic strands WW run between the two non-woven elastic non-woven composite (cross-direction), but is then cut by a knife (see knife 1410 in FIG. 14, as described below), thereby separating the two wrapped composites. At stage G, the composites 1 and 2 are fed away from the conveyor assembly 1009 and the folded flaps on webs 1 and 2 become unfolded, with guiding, to form a flat non-woven composite. Subsequently, the composites are guided from the spinning head assembly 1007 and conveyor assembly 1009 and into further processes. As shown in FIG. 10, the elastic output webs arrives via a system of rollers onto an elastic composite output reel 1005.

FIG. 14 provides an alternate view of the conveyor assembly 1009. This Figure further illustrates the movement of non-woven webs 1-4, and the application of elastic strands in a generally mutually parallel pattern and generally spaced apart from one another. After cutting of the elastic with the knife 1410, two elastic composites are directed away from the conveyor assembly 1009. It should also be noted that the inventive system advantageously allows for improved control of the stretch of the elastic strands.

As shown in FIGS. 11 and 14, the conveyor assembly 1009 preferably includes two web moving platforms 1412 which are juxtapositioned so as to provide an interface therebetween. Each web moving platform 1412 includes a continuous belt 1414 supported about a plurality of rollers 1416 so as to be capable of reciprocal motion. The two web moving platforms 1412 are generally the same length and juxtapositioned so as to accommodate the non-woven webs 1 and 2 therealong from one end to the other end. Preferably, a roller 1416 is situated about midway between the ends of the web moving platform so as to deliver the non-woven webs 3 and 4 respectively to the web moving platform.

As shown in FIG. 10 and also FIG. 14, the spinning head assembly 1007 is positioned about and in the vicinity of one end of the conveyor assembly 1009. In operation, the spinning head 1017 spins about the vertical plane XX which intersects the ends of the web moving platforms 1412 so as to deliver the elastic strands WW around and about both web moving platforms 1412. In operation, the first and second non-woven move along the outside or exposed surfaces or sides of the web moving platforms 1412 and receives the elastic strands WW delivered by the spinning head 1017. By way of its movement away from the spinning head 1017, the moving web draws the continuous elastic strand WW from the spinning head 1017.

By pre-folding the two non-woven webs that are fed to the inside of the conveyor assembly 1009, it is possible to create an elastic composite with cross directional stretch having non-elasticized regions ("dead zones") along each edge. The width of the central elasticized region is fixed to the width of the conveyor platform 1412. The width of the non-elasticized regions or dead zones is determined by the width of the fold VV. The fold VV in the non-woven is preserved by the conveyor assembly 1009 during application of the elastic element and is applied in such a way that the folded edge of the non-woven is not in contact with the elastic element WW. The fold VV is then allowed to open after the composite exits the conveyor assembly 1009 to provide a flat elastic composite with non-elasticized regions. By altering the alignment of the materials as it enters the conveyor assembly 1009 or by changing the widths of the materials used it is possible to create various composite designs.

The above-described process provides an elastic composite with cross directional stretch properties. The process also provides non-elasticized regions on either latitudinal side of the central elasticized zone of the composite. For the purposes of the description the term "non-woven" is used to describe the principal material used in the construction of the elastic composite. However, it should be noted that this invention is not limited to non-woven materials but may be applied to any material that is available in the form of a continuous sheet. Other materials suitable for this application include PE film, PE film/non-woven laminates and tissue.

Figure 15:
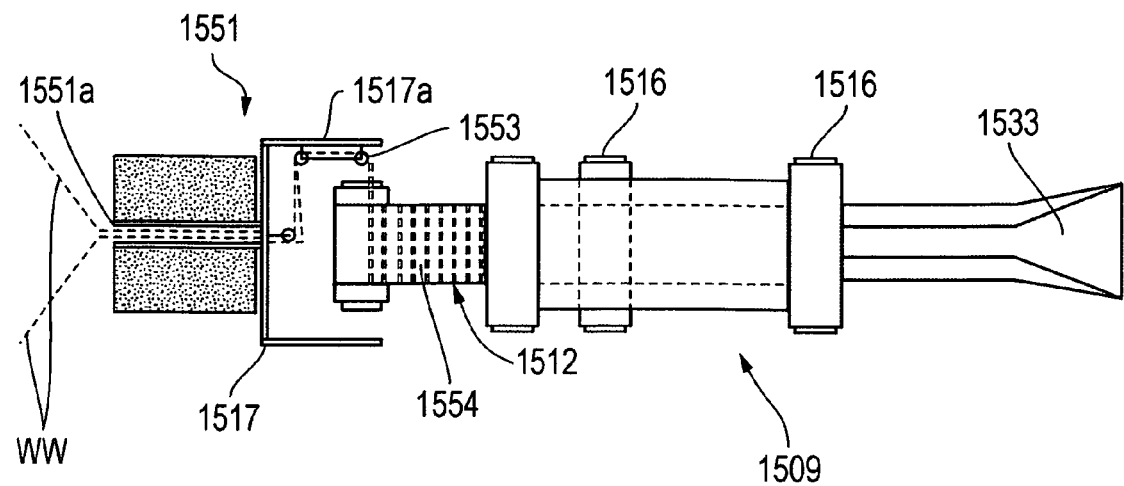
FIG. 15 is a top view of an alternative elastic element applicator assembly for use with the system of FIG. 10, according to the invention.

FIG. 15 illustrates a conveyor assembly 1509 and an elastic element applicator in the form of a spinning head assembly 1507, in accordance with an alternative embodiment of the present invention. As will be understood by one skilled in the art, the spinning head assembly 1507 is operated to convey or transmit elastic strands onto a web moving platform 1512 of the conveyor assembly 1509. As before, the conveyor assembly 1509 preferably employs two web moving platforms 1512, which are juxtapositioned so as to provide an interface therebetween. The conveyor assembly 1509 is similar to that illustrated in FIGS. 10 and 11.

On the other hand, the conveyor assembly 1509 is operated differently in that more than one elastic strand WW is applied onto and about the web moving platforms 1512 at one time. The spinning head assembly 1507 includes a spinning head in the form of a spin bracket 1517 having a plurality of arms 1517a. The spin bracket 1517 receives elastic strands 1553 from a shaft 1551a of a motor 1551. The motor 1551 feeds the two lines of elastic strands 1553 to the spin bracket 1517, and the two feeds of elastic strands 1553 are guided together through the spinning head assembly 1517 (where the two lines twist together). As shown in FIG. 15, the two strands 1533 are moved about a v vertical plane then delivered, together, onto a nonwoven web 1544 moving horizontally on the web moving platform 1512. Preferably, both lines of elastic strand 1553 are fed onto the same arm 1517a of the spinning bracket assembly 1517 (rather than on opposite sides). In this way, the separate feeds or lines of elastic strands 1553 are prevented from twisting together and possibly breaking.

By applying two lines (or more) of elastic strands onto the moving nonwoven web, the speed of the manufacturing process is increased. Specifically, the speed at which the composite is manufactured may be increased by up to 100%, without increasing the speed at which the spinning head assembly is spinning and without changing the overall number of elastic strands in the final composite. Table 1 below provides two examples of the result of a process of applying the elastic strands WW onto a nonwoven web, according to the present invention. The spinning head assembly 1517 operates at the same rotational speed in both processes. However, the pitch (i.e., the separation between elastic strands WW) is doubled for the alternative process (wherein a pair of elastic strands are applied to the nonwoven web). By employing the alternative process, the total machine output is also doubled (i.e., from 40 m/min of composite to 80 m/min). In both examples, the overall amount or length of elastic strands WW utilized or applied to the composite is generally the same. Consequently, the final composite produced by both subprocesses have the same, or at least, similar tensile characteristics.

TABLE 1

| Spin head speed | Pitch (elastic separation) | No of elastic strands fed into spin head | Total machine output (two webs of composite) |
|---|---|---|---|
| 8,000 rpm | 2.5 mm | 1 | 40 m/min |
| 8,000 rpm | 5 mm | 2 | 80 m/min |

It will be apparent to one skilled in the relevant art, upon reading the present description and/or reviewing the accompanying drawings, that the alternative subprocess described above may be modified to feed or apply a different number of elastic strands onto the nonwoven web. That is, three or more elastic strands may be fed through the spinning head assembly and applied to the nonwoven web.

Moreover, it is contemplated that the elastic strands may be separated inside the spin head and directed independently to opposite sides of the nonwoven web. In such a case, it is preferred that the assembly 1507 that includes the elastic bobbins/reel and tensioners and guides the elastic strands into the motor 1551 (or more appropriately, the motor shaft 1551a), is rotated at the same speed and in the same direction as the spin head 1517. In this way, the risk of twisting of the strands together inside the spin head 1517 is minimized.

FIGS. 17A-19B are provided to illustrate aspects and embodiments of another present invention. In particular, FIGS. 17B and 18B depict alternative elastic composites according to the invention. FIGS. 19A and 19B illustrate an exemplary system that is operable to implement a method of making the elastic composite also according to the invention. The exemplary system may be used with or integrated into the system(s) previously described in respect, for example, to FIGS. 10-16. The invention, and its various aspects and embodiments, shall be understood in view of FIGS. 17A-19B and/or the accompanying descriptions, as well as the previous illustrations in FIGS. 1-16 and accompanying descriptions.

These additional Figures are provided for illustration and to facilitate a description the present invention. The present invention shall not, therefore, be limited to the structures and processes specifically described and illustrated in respect to FIGS. 17A-19B. FIGS. 1-16, and accompanying descriptions, demonstrate application of a tensioned elastic strand across a moving web of nonwoven sheet. The elastic strand was affixed to the nonwoven sheet so as to provide a composite having, among other attributes, cross-directional elasticity. In respect to previous illustrations, the elastic strand, or a group of elastic strands, were fed via a single path and then applied to a moving web of nonwoven sheet by operation of a spin head. The elastic strand or group of elastic strands are distributed onto the web at the rate of one strand per single revolution of spinhead.

In a further aspect of the invention, a method is now described whereby multiple strands, e.g., two strands or two separate group of strands, are applied to a moving web of nonwoven sheet. Preferably, the strands or collection of strands travel by two separate paths and are distributed onto the web of nonwoven sheet at the rate of two strands per single revolution of the spinhead. The two strands may be applied simultaneously to different portions of a conveyor assembly conveying one or more webs. This variation of the invention provides advantages in efficiency as the output of the machine is increased by at least 100%. Alternatively, the machine speed may be reduced by as much as 50%, providing a reduction in running costs due to wear and tear and energy consumption. The present inventive method maintains, however, the same output and volume as the single path processes previously described.

The following terms are used to describe certain system(s) and process(es) for making an elastic composite. In particular, these terms describe different running configurations associated with this alternative method of manufacturing an elastic composite. First, the term "single strand, single path method (SSSP)" refers to a method of manufacture whereby one strand of elastic element is delivered to a web of nonwoven sheet at the rate of one strand per single revolution of the spinhead and via a single path or mode of travel through the spinhead. This method was previously described in respect, for example, to FIG. 13. Second, the term "multiple strands, single path method (MSSP)" refers to a method of manufacture whereby multiple strands of elastic element are grouped together and distributed via a single path or mode of travel through the spinhead. In this method, the elastic strands are distributed on the web of nonwoven sheet at the rate of one collection of strands per revolution of the spinhead. An example of this method was described in respect to FIG. 15.

Furthermore, the term "single strand, dual path method (SSDP)" refers to a method of manufacture whereby two strands of elastic element enters the spinhead and are distributed onto the web of nonwoven sheet via two separate paths or modes of travel, in accordance with the present invention. In this method, the elastic elements are distributed on the moving web of nonwoven sheet at the rate of two strands per revolution of the spinhead. The term "multiple strands, dual path method (MSDP)" refers to a method of manufacture whereby two sets of more than one strand are collectively grouped and are distributed on the web via two separate paths or modes of travel through the spinhead. In this method, the elastic elements are distributed at the rate of two collections of strands per revolution of the spinhead.

As used hereafter, a substantially long feed of elastic may be referred to as a "continuous strand" even though it is understood that the strand is not infinitely long. Relative to the dimensions of the elastic elements arranged on the elastic composite, the elastic strand is, for practical purposes, continuous. For present purposes, the term "continuous", as applied to "strand", shall indicate a length that will not be consumed in less than a few revolutions of the spinhead. Moreover, the term "strand" is used to refer to the feed or continuous length of elastic whereas the section or segments applied to the elastic composite may be referred to as "elastic elements." A "section" of elastic is referred to herein as the length (i.e., the end length) outside of, fed by, the arms or eyelets of the spinhead and is spun by the spinhead.

Figure 17A:
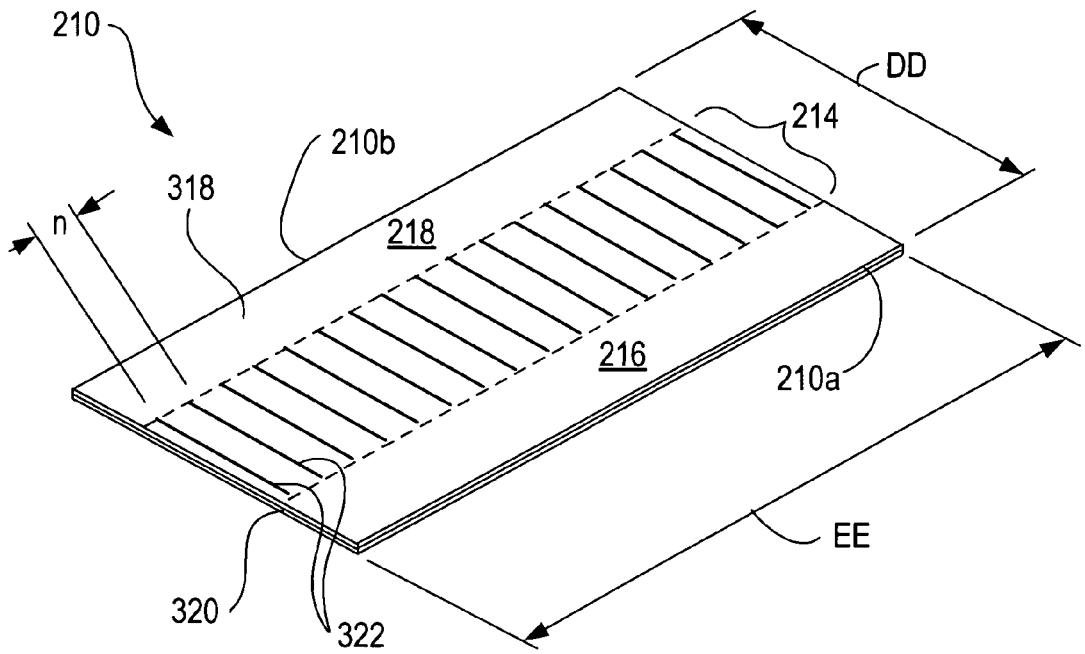
FIG. 17A is a perspective view of an elastic composite used for reference.

FIG. 17A reproduces, in an alternative view, the elastic composite 210 depicted in FIGS. 2A, 2B, and 3. Although shown in the stretch state, the elastic composite 210 has a fixed width DD in the lateral direction and a predetermined cut length EE along the longitudinal direction. During the manufacturing process, a continuous web of the elastic composite 210 is delivered as output, having continuous longitudinally directed side edges 210a, 210b and a central elasticized region 214 in which an elastic construction is situated. Extending laterally from the elasticized region 214 are non-elasticized regions 216 and 218 (also referred to herein as "dead zones"). The elastic composite 210 includes a top layer 218, a bottom layer 220, and a plurality of elastic elements 322 sandwiched therebetween. The top and bottom layers 218, 220 provided in most, if not all, of the examples in these descriptions are preferably nonwoven. It is contemplated, however, that other materials may also be used, including a variety of textile materials, fabrics, and the like.

As previously described in detail, the elastic element 322 extends generally along a direction generally perpendicular to the longitudinal or machine direction and are spaced apart from one another by a generally fixed distance n or pitch. The pitch n is directly related to the manufacturing process settings and may be calculated as follows:

$$n(mm) = \frac{(\text{speed of conveyor}(m/min))}{(\text{rotational speed of spinhead }(rpm))}$$

Figure 17B:
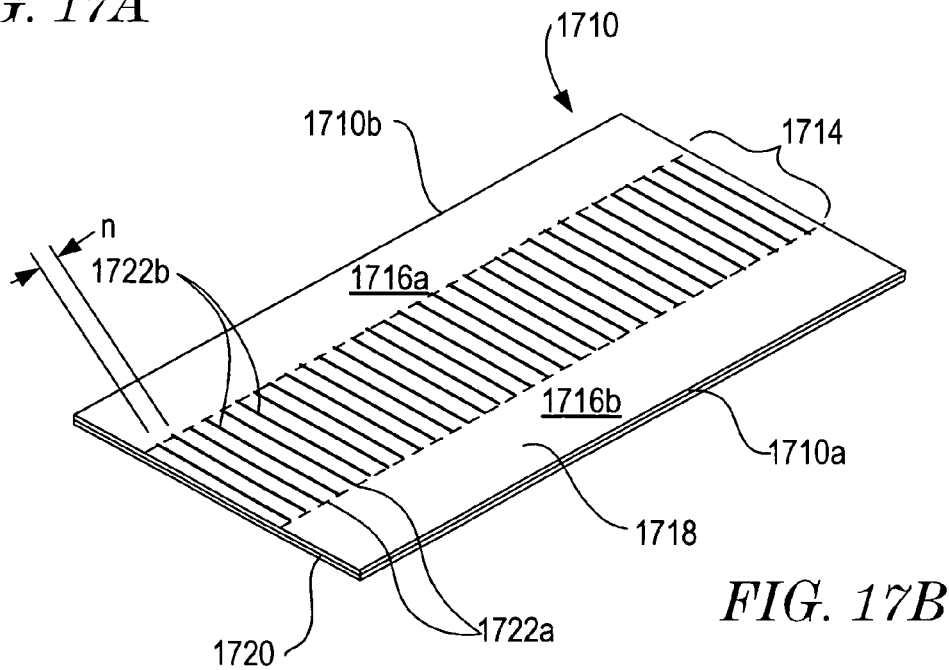
FIG. 17B is a perspective view of an elastic composite, according to one embodiment of the present invention.

FIG. 17B depicts an exemplary sheet of elastic composite 1710 according to the present the invention. The elastic composite 1710 has been manufactured in accordance with a single strand dual path method. The elastic composite 1710 includes sections and components that are identical to those of the elastic composite 210 in FIG. 17A, with the exception of a central elasticized region 1714. Sandwiched between a top layer 1718 and a bottom layer 1720 are a plurality of spaced-apart, laterally extending elastic elements 1722. In this embodiment, the distribution of elastic elements 1722 is alternately provided by a first elastic element 1722a and a second elastic element 1722b. The first and second elastic elements 1722a, 1722b differ in that one is fed from a source different from the source of the other. As will be further explained below, the sources are preferably a first continuous elastic strand and a second distinct, continuous, elastic strand. Typically, the two continuous elastic strands are of the same material type and have the same material properties, but may be varied, in further embodiments, to impart specifically targeted elastic properties to the elastic composite 1710. The two elastic strands may also differ in thickness (see e.g., FIG. 29B as described below), as well as or in lieu of varying elasticity. One of the elastic strands may even be a type of activated elastomer (e.g., heat activated). Further, the two elastic strands may have a different color to achieve a specific aesthetic design, for example. Thus, the method according to the present invention provides some flexibility in the functional and aesthetic design of the elastic composite.

The elasticized region 1714 includes an arrangement consisting of alternating first and second elements 1722a, 1722b that are spaced apart by a generally fixed distance or pitch n'. This pitch n' is reduced from the pitch n in the previous elastic composite 210 (see FIG. 17A), thereby providing for a greater elastic density across the elasticized region 1714. As will be further described below, the two elastic elements 1722a, 1722b are distributed onto the web or nonwoven substrate preferably from opposing sides of the spinhead. For every revolution of the spinhead, two strands of elastic elements 1722a, 1722b are delivered onto the web. Employing an MSDP method, the value of n' may be calculated one half of that obtained by the SSSP method (assuming that the speed of the nonwoven conveyor and spinhead are maintained at the same speed as before):

$$n'(mm) = \frac{(\text{speed of conveyor}(m/min))}{2 \times (\text{rotational speed of spinhead }(rpm))}$$

Figure 29A:
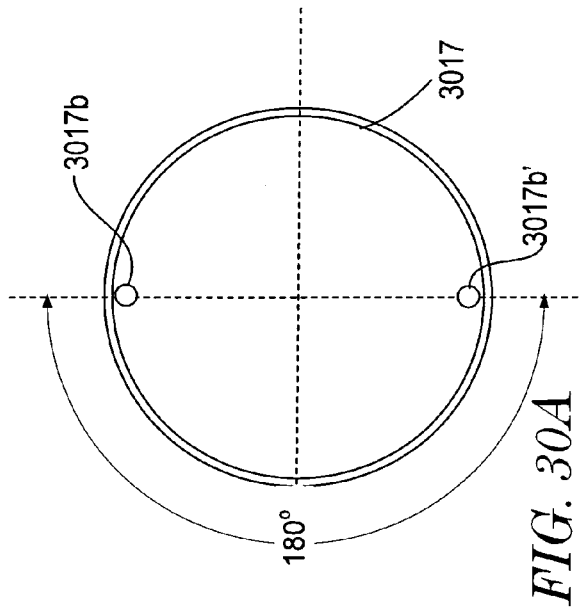
FIG. 29A is a simplified illustration and front view of an alternative elastic element applicator in the form of a spinhead, according to the present invention.
Figure 29B:
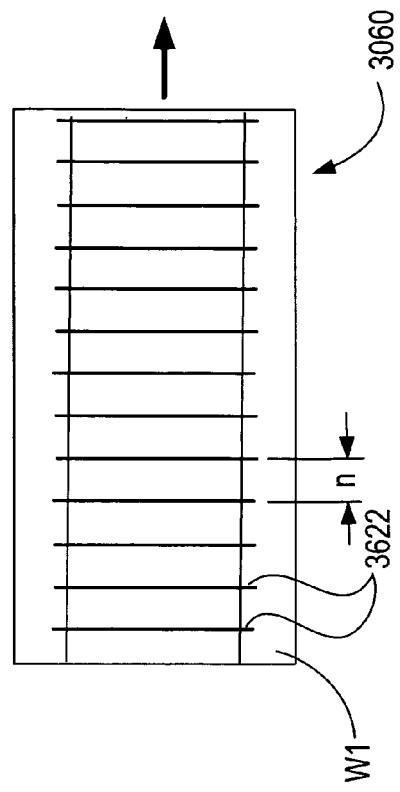
FIG. 29B is a simplified illustration and top view of a web substrate conveyed in a method of making an alternative elastic composite, according to the present invention.

In an alternative embodiment, two elastic strands are distributed from the spinhead at locations less than 180° apart (phase separation in one spin revolution), as shown in FIG. 29A, for example. In this way, the pitch between elastic elements may be varied. FIG. 29B depicts an exemplary web substrate 2960 whereon a plurality of first elastic elements 2922a and second elastic elements 2922b are applied on a moving first input web W1. The distribution of elastic elements provides an alternating sequence of first elastic element—second elastic element—first elastic element on the web substrate 2960. The first and second elastic elements 2922a, 2922b are provided by, and are discrete, severed portions of, different elastic strands. In this example, the first elastic element 2922a has a greater thickness than the second elastic element 2922b. Moreover, the distribution of elastic elements provides for different or alternating pitch between successive elastic elements in the sequence. The elastic elements 2922a, 2922b are alternately separated by a pitch of n1 and a pitch of n2. In this depicted example, the larger pitch n2 is three times greater than the pitch n1. As will be further explained below, this alternating pitch sequence may be achieved by providing a spinhead 2917 such as the spinhead 2917 illustrated in FIG. 29A. The spinhead 2917 has a pair of eyelets 2917b, 2917b' for distributing a first continuous strand W and a second continuous strand W' respectively. The eyelets 2917b, 2917b' are separated by a distance of 90° (followed by a separation of 270° in the opposite direction). In providing eyelets that are not generally diametrically opposed about the spinhead, design provisions are preferably made to provide balance to the spinning spinhead.

Figure 30A:
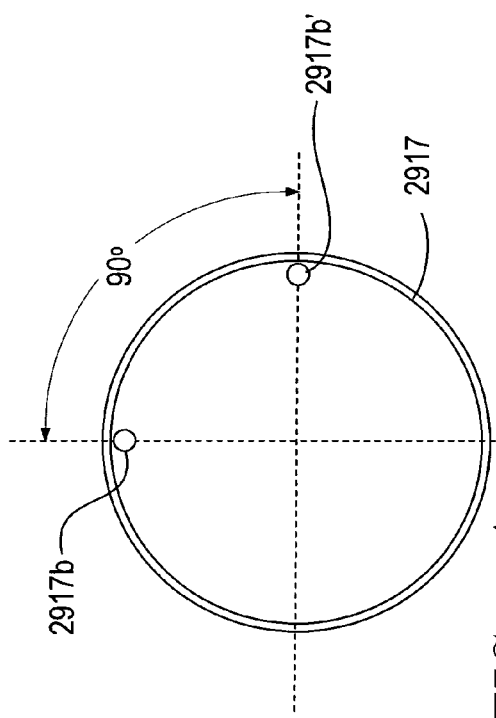
FIG. 30A is a simplified illustration and front view of an alternative elastic element applicator in the form of a spinhead, according to the present invention.
Figure 30B:
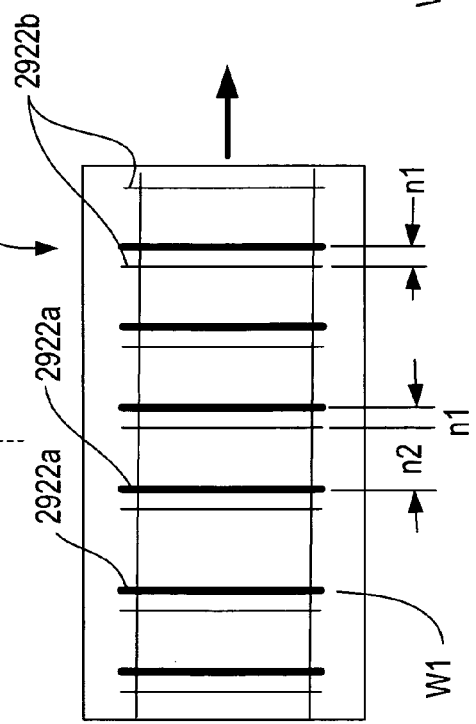
FIG. 30B is a simplified illustration and top view of a web substrate conveyed in a method of making an alternative elastic composite, according to the present invention.

As comparison, FIG. 30 provides a front view of a spinhead 3017 wherein a pair of strand dispenser eyelets 3017b, 3017b' are diametrically opposed and thus, separated by 180° (spin phase revolution). The eyelets 3017b, 3017b' are therefore equidistantly spaced from each other in either direction. Operation of this spinhead 3017 generates a web output 30360 whereon each successive pair of elastic elements 3022a, 3022b are ultimately separated by a pitch n, as discussed previously.

Figure 18A:
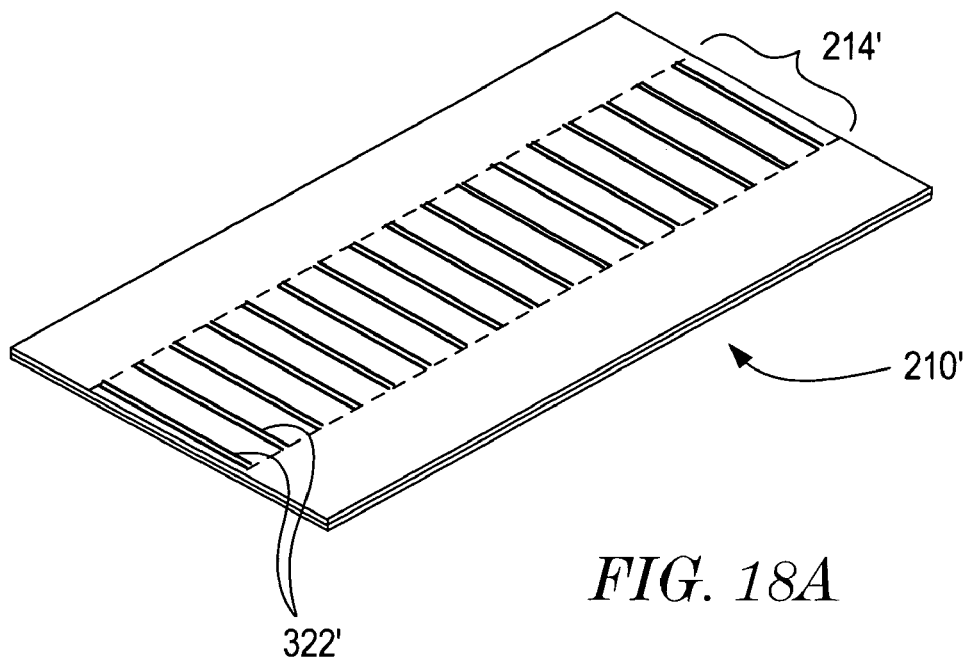
FIG. 18A is a perspective view of another elastic composite used for reference.

FIG. 18A depicts an elastic composite 210' manufactured in accordance with the method previously described in respect to the system of FIG. 15. Specifically, the elastic composite 210' is manufactured by an MSSP method. The elastic composite 210' includes sections and components that are generally identical to those of the elastic composite 210 in FIG. 17A, with the exception of the elasticized region 214'. The elasticized region 214' is composed of discrete groups 322' of multiple elastic elements that extend generally in the lateral direction. The center of the groups 322' of elastic elements are spaced apart from one another in generally parallel relation by the same fixed distance n (from FIG. 17) (a center-to-center distance). In accordance with the method previously described in respect to the system of FIG. 15, a group 322' of elastic strands is delivered to the web upon each revolution of the spin head. In the elastic composite 210' depicted in FIG. 18A, the groups 322' consist of two adjacent elastic elements.

Figure 18B:
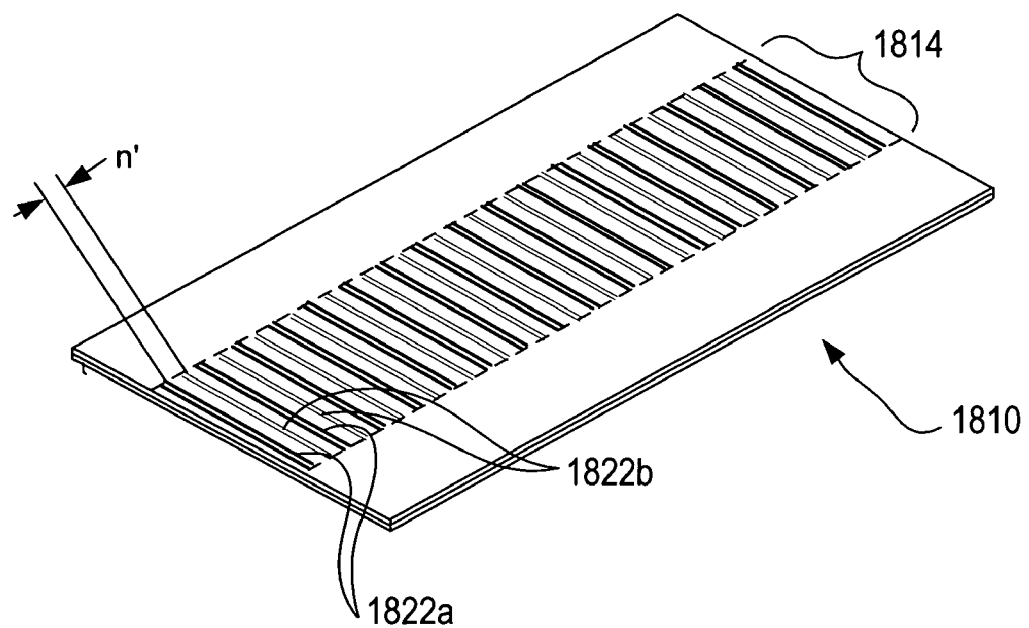
FIG. 18B is a perspective view of an alternative elastic composite, according to another embodiment of the present invention.

FIG. 18B depicts an exemplary elastic composite 1810 according to a further embodiment of the present invention. The elastic composite is manufactured by an MSDP method, in accordance with an alternative embodiment of the present invention. The elastic composite 1810 includes sections and components that are generally identical to those of the three previously described elastic composites 210, 1710 and 210', with the exception of the elasticized region 1814. In this exemplary elastic composite 1810, two different groups of elastic strands 1822a, 1822b are delivered onto the web upon each revolution of the spinhead. The lateral centerlines of the groups 1822a, 1822b are spaced apart by the smaller pitch n'—as with the elasticized region 1714 in FIG. 17B. Assuming that one type of elastic element is used for the elastic composites in each of FIGS. 17A, 17B, 18A, 18B, the resulting elasticized region 1814 in this embodiment imparts a greater degree of elasticity to the elastic composite 1810 than any of the other arrangements. A higher elastic density is achieved by both providing for a smaller fixed distance, n', between the individual elastic elements or groups and providing for more elastic elements at application by the spin head. Furthermore, the speed of the operation is increased from the operation associated with each of the elastic composites in FIGS. 17A and 18A.

It should be noted that the elastic elements within each of the two groups 1822a, 1822b may be varied or may be of one type. Further, the constituents of the other two groups may be different or identical.

The elastic elements are directed generally perpendicular to the longitudinal or machine direction. Further, the elastic elements are structurally independent of each other, although in some embodiments may be of (i.e., severed sections) one or more elastic strand. In FIG. 17A, for example, all of the elastic elements are elastic elements of a single, continuous strand, although, in the composite, the elastic elements are structurally independent. Furthermore, each elastic element generally does not have a vertical (or longitudinal) component. As a result, a certain uniformity in horizontal elasticity is achieved. In some embodiments, this characteristic provides an elongated elastic composite that does not tend to twist or kink when at rest, and at rest, is more uniform and aesthetically pleasing.

Table 2 below summarizes some of the benefits and advantages attained by the different manufacturing methods discussed above. To facilitate the comparisons, the number of elastic elements per unit of linear length provided by the four methods is the same. Thus, the tensile and elastic properties of the output elastic composites are similar.

TABLE 2

| Manufacturing method | SSSP | MSSP | SSDP | MSDP |
| --- | --- | --- | --- | --- |
| Number of elastic elements applied per revolution | 1 | 2 | 2 | 4 |
| Machine output Spinhead speed = 8000 rpm Elastic elements per linear meter = 400 | 40 m/min | 80 m/min | 80 m/min | 160 m/min |
| Pitch (separation of elastic strands) | 2.5 mm | 5 mm | 2.5 mm | 5 mm |
| Examples of Advantages | — | *Efficiency: Output Increased by 100% | Aesthetic: Pitch is ½ of that for MSSP Efficiency: Output Increased by 100% over SSSP | Efficiency: Output Increased by 300% over SSSP |

*Formula for machine efficiency: Output (m/min) = spinhead speed (rpm) × no. of elastic elements applied per revolution × pitch × 2.

Table 2 illustrates the design and operational flexibility attainable through employment of the various methods previously described. As will become apparent to one skilled in the art provided with the present disclosure, certain methods may prove more useful than others depending on the particular design and operational requirements. In this regard, attention is now directed to the systems available to implement these manufacturing methods.

With reference to FIGS. 19A and 19B, a method of making an elastic composite of the invention utilizing a dual path method is now described. The inventive method is described in conjunction with a description of an exemplary system 1901 of making the elastic composite.

FIGS. 19A and 19B depict a system 1901 and system components, and illustrate a method of making an elastic composite (e.g., elastic composite 1710 or 1810) according to the present embodiment. The system and its components are substantially similar to those previously described. The differences between the previously described systems and the system 1901 of FIGS. 19A, 19B represent improvements provided by the present invention. These differences will be the focus of the following description.

For purposes of the present description, references will be made to upper and lower relative positions, as well as right and left directions and positions. It will be understood by one skilled in the art that these positional and directional references are made for description only, and that the invention is not to be limited by their use. Further, it will become apparent that variations of the system and process may be made, utilizing different positions and directions for the various system components and feeds.

For the most part, the system 1909 includes the same components provided, for example, in the system depicted in FIGS. 11-16. The system 1901 includes a conveyor assembly 1909 for receiving, manipulating, and conveying each of the two nonwoven web inputs. The conveyor assembly 1909 is positioned next to, and operatively associated with, an elastic element applicator in the form of a spinning head assembly 1907. The spinning head assembly 1907 is operable to apply elastic fibers or strands upon, onto, and/or integrally with an input web of nonwoven conveyed by the conveyor assembly 1909. The spinning head assembly 1907 further includes a spinhead 1917, preferably in the form of a spinning bracket or cylinder 1917 (spinhead). The spinhead 1917 is configured to hold an "end section" of the continuous strand WW of elastic element and move it about a generally vertical plane XX in a reciprocal or repetitive manner (relative to the conveyor assembly 1909). As described previously, this plane XX is defined by the area within the spinning perimeter of the cylinder 1917 that is traced by the outer-most bracket or eye 1917b securing the continuous strand WW to the spin cylinder 1917. It is understood that the vertical plane XX need not be at 90° to the web platforms U, L (and thus, to the web plane moving direction), but it is generally preferred. The path of the spinning head 1917 and the section of elastic strand retained thereby are provided on the plane XX. In FIG. 19A, the section of strand WW between the eyelet 1917b and the platform U is indicative of a linear portion of the plane XX.

Referring also to FIG. 21A, the conveyor assembly 1909 includes an upper conveyor or web moving platform U (web platform U) provided by a movable, continuous belt U1 and a series of rollers supporting the belt U1. The conveyor assembly 1909 further includes a lower conveyor or web moving platform L (web platform L) also provided by a movable, continuous belt L1 and a series of rollers supporting the belt L1. In the side view of FIG. 19B, the lower belt L1 is positioned in generally parallel relation with the upper belt U1 and vertically spaced therefrom by a distance or gap HH. Although the belts U1, L1 are designed for reciprocal motion during system operation, the belts U1, L1 may be described as having a planar outside deck or surface S1, S3 and a planar inside deck or surface S2, S3 at any fixed point in time (for purposes of the present description). The use of "inside" and "outside" references are made in view of the relative locations of the surfaces (i.e., facing outside of the assembly 1909 or facing inside the assembly 1909). This use of such references is provided to facilitate the description only, and should not be construed as a limitation on the inventive system and method.

As represented in the plan view of FIG. 19B, each of first and second primary inputs webs W1, W2 provide a web of nonwoven utilizing a series of rollers and guides. The two webs W1, W2 are first directed through folding guides or plates, which serve to effectively reduce the overall width of the nonwoven web by folding the ends or side edges along a predetermined, longitudinally extending side fold line. As previously described, the input webs W1, W2 are directed centrally into the gap HH between the upper and lower web platforms U, L, along a first web plane moving direction, MM and toward the spinhead 1917. This first web plane moving direction MM also corresponds to a direction from right to left in the side view of FIG. 19B. This first web plane moving direction MM also directs the nonwoven inputs 1903a, 1903b toward the center of the spinhead 1907. Once inside the spinhead 1917, the conveyor assembly 1909 reverses the direction of travel of the input webs W1, W2 (a turn of 180 degrees), from the first web plane moving direction MM to the oppositely directed second web plane moving direction NN. The second web plane moving direction NN is identical (orientation) to the first web moving plane moving direction MM, except that the directions are reversed.

As the input webs W1, W2 exit the spinhead 1917, a first elastic strand WW is wrapped around the entire conveyor assembly 1909 and contacts the outside surfaces S1, S3 of the belts U1, L1, respectively. The first elastic strand WW also comes into contact with the moving webs W1, W2. The elastic strand WW is applied crosswise or laterally on the web, and transverse to the second web plane moving direction NN. As explained previously, this transverse direction is also the cross-machine direction. Friction between the elastic strand WW and the input webs W1, W2 on the belt surfaces S1, S3, helps to draw the "wrapped" elastic strand WW out of the spinhead 1917.

As already described, the system 1901 positions a first elastic input source E1 on the left side of the system 1901 (in the views of FIG. 19A, 19B). The input source may be in the form of a spool of elastic. The continuous first elastic strand WW is delivered through a hollow shaft in a motor that controls the spinhead 1917. The elastic strand WW then passes into the spinhead 1917 and is guided by rollers, eyes, or other suitable means, around the inside of the cylinder of the spinhead 1917.

In this particular embodiment of the present invention, the system 1909 further employs a second elastic input source E2 that is, in the views of FIGS. 19A, 19B, positioned on the right side of the system 1901. A second continuous elastic strand WW' may be delivered via any suitable system of rollers and eyes, centrally along the gap HH and into the open end of the spinhead 1917. Upon exiting the gap HH, the second continuous elastic strand WW' is directed across the center of the spinhead 1917 and to the back of the spinhead 1917. The second continuous elastic strand WW' is then guided by rollers, eyes, or other suitable means, around the inside face of the cylinder, to an eyelet 1917b' positioned diametrically opposite (180°) of the eyelet 1917b of the first continuous elastic strand WW. Thus, the first and second elastic strands WW, WW' are separated by 180°, within the spin cylinder. By taking opposite paths around the spinhead, the risk of entanglement between the two continuous elastic strands WW, WW' is substantially alleviated. Further, the elastic strands WW, WW' are preferably tensioned by passing the continuous strand through any suitable tensioning unit prior to being received by the spinhead 1917.

As the spinhead 1917 is spun around the upper and lower platforms U, L, sections of the first and second elastic strands WW, WW' are applied simultaneously about the two web moving platforms U, L. Referring to the exemplary spinhead 1917 of FIGS. 19A and 19B, the eyelet 1917*b*' for the second elastic strand WW' is shown at a position slightly forward of the eyelet 1917*b* of the first elastic strand WW. Preferably, the eyelets 1719*a*, 1719*b* are not separated as such, but aligned so as to provide a common vertical plane XX. The mis-alignment depicted in FIGS. 19A, 19B are provided primarily to best show the distribution of elastic strands WW, WW' about the conveyor assembly 1909.

It is contemplated, however, that certain other applications may be best implemented by positioning one eyelet forward of the other, as shown. In such an application, the generally vertical plane XX, about which the first elastic strand WW is spun, is slightly left of a second generally vertical plane XX' (not shown), about which the second elastic strand WW' is spun. The two vertical planes XX, XX" are disposed in mutual parallel relation and both intersect the upper and lower platforms U, L. The elastic elements WW, WW' are applied onto the moving webs at these linear intersections of the vertical planes XX, XX' with the belt surfaces S1, S3 (i.e., along the web path of the nonwoven webs). The positions of the eyelets 1917*b*, 1917*b*' may be adjusted to achieve the desired pitch n' discussed above.

In a further embodiment initially described in respect to FIGS. 29A, 29B, the position of the eyelets 1917*b*, 197*b*' are not diametrically disposed but positioned less than 180 degrees apart. In this way, the pitch between elastic elements may be adjusted to satisfy design requirements. The eyelets 2917*b*, 2917*b*' in FIG. 29A are positioned about 90 degrees apart in one direction and about 270 degrees in the opposite direction. Operation of the spinhead 2917 provides for a web substrate 2960 whereon the elastic elements 2922*a*, 2922*b* (from elastic strands W and W', respectively) are separated by alternating pitch distances of n (n1) and 3n (n2).

FIGS. 20A and 20B depict an alternative system 2001 (to the system 1901 of FIGS. 19A and 19B) for making the elastic composite according to the invention (wherein like reference numerals are used to indicate like elements). In this embodiment, a bracket system 2090 of tensioning rollers is provided proximate the end of the web platforms U, L and the end of the gap HH. The bracket system 2090 directs the second continuous elastic strand WW away from the centerline AA of the spinhead momentarily to avoid front rollers 2084. The bracket system 2090 may be supported or suspended between the upper and lower web platforms U, L, and in between the input webs W1, W2, by any suitable means.

[[Expand]]

Returning to FIGS. 19A and 19B, further description of the invention system and method will now be provided, particularly that of the intersection between the primary input webs W1, W2, continuous strands WW, WW', and secondary input webs W3, W4. FIGS. 21A-21D provide cross-sectional views through the system 1901 depicted in FIG. 19. These simplified views are provided to illustrate certain points in the process of applying elastic elements onto the nonwoven webs. Referring to FIG. 21A, a first cross-sectional view also is presented proximate the ends of the two web platforms U, L. The view reveals cross-sections of the two continuous belts U1, L1. This view includes cross sections showing outside belt surfaces S1, S3, and inside belt surfaces S2, S4. As viewed in FIG. 21A, the two inside belt surfaces S2, S4 move out from the page along the first web plane moving direction MM and convey the input webs W1, W2 into the spinhead 1917. The two outside surfaces S1, S3 move into the page along the second web plane moving direction NN and convey the webs W1, W2 away from the spinhead 1917. The input webs W1, W2 of nonwoven are shown on the belts U1, L1 with their ends already folded.

As used herein, the term "web plane path" shall mean the path (including direction) taken by the input webs W1, W2 as conveyed by the conveyor assembly 1909. For one input web, the "web plane path" includes the path along the inside surface S2 of the continuous belt U1 directed along the first web plane moving direction MM and the path along the outside surface S1 of the same belt U1 directed along the second web plane moving direction NN. The web plane path of the other input web is different from the first web plane path, although it is also directed, in certain segments of the path, in the same web plane moving directions MM or NN. As described herein, the vertical plane XX, XX' intersects the web plane path on the outside belt surface S1 and along a transverse line common with the web plane path.

Referring to FIG. 21B, a cross-sectional view is provided across a section further away from the spinhead. At this point in the process, the spinhead 1917 has applied several sections of the first and second continuous elastic strands WW, WW' about the conveyor assembly 1909, and more specifically, over the input webs W1, W2. In doing so, the spinhead 1917 has applied the continuous elastic strands WW, WW' transversely in respect to the second web plane moving direction NN.

Referring to FIG. 21C, a cross-sectional view is provided across a section downstream of the rollers for the third and fourth input webs W3, W4 of nonwoven. The rollers facilitate the application of a second web layer upon each substrate that now includes the elastic elements and a first nonwoven web. In this manner, a moving web of elastic composite is produced consisting of a top layer of nonwoven sheet, a base layer of nonwoven sheet, and elastic elements sandwiched therebetween. At this point, the ends of the input webs W1, W2 are still folded around the ends of the belt surfaces S1, S3. The view of FIG. 21C also indicates the locations of knife mechanisms KK where the elastic strands WW, WW' are cut immediately downstream of the cross-sectional view. As discussed previously, the cuts may be provided by knife structures located adjacent the web platforms U1, L1.

The cross-sectional view of FIG. 21D represents a point further downstream in the process. In this view, the continuous elastic strand WW, WW' has been cut to provide a distribution of segmented elastic elements 1722 within the web substrate. Every other segmented elastic element 1722 in the distribution is characterized as having originated from the same first or second continuous elastic strand. Further, each pair of adjacent or sequential elastic element 1722 are characterized as having originated from a different continuous elastic strand. This view also reveals that the first and second input webs 1903 have been unfolded, in a manner described previously. FIG. 21D depicts, therefore, a cross-section of web outputs O1, O2 of the system and method of manufacture, according to the invention.

Figure 22:
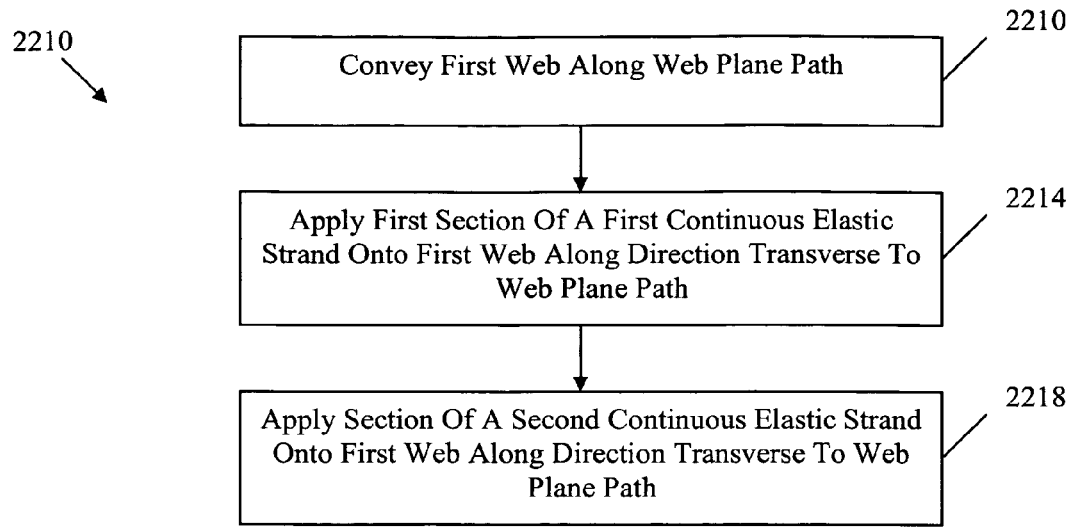
FIG. 22 is a simplified flow chart illustrating basics steps of a method of making an elastic composite, according to the present invention.

FIG. 22 provides a simplified flow chart of the basic steps of a method of making an elastic composite, in accordance with the present invention. The flow chart 2210 also provides a summary of the process described in respect to FIGS. 19-21. The basic steps of the method are preferably performed through operation of a system such as the exemplary systems 1901, 2101 of FIGS. 19 and 20. In an initial step 2210, a first web of material (e.g., a nonwoven layer) is conveyed along a web plane path. The web plane path is simply a path along which a web having an expanse (i.e., width and substantial length) may be conveyed. The web plane path is preferably controlled by a fixed system to provide a consistent path for a moving, continuous web, directed along a predetermined web direction (which is planar). As illustrated previously, the web plane path is generally predetermined, in the preferred embodiment, by the web platforms of a conveyor assembly and the conveying step 2210 is implemented through operation of the web platforms. A section of a first continuous elastic strand is then applied onto the first web and generally transversely to the web plane path (Step 2214). Further, a section of a second elastic strand is applied onto the second web and generally transversely to the web plane path (Step 2218). These steps 2214, 2218 are preferably performed through operation of a single spinhead that spins the two strands about the first web being conveyed and about a plane(s) that intersects the moving web. By repeating the applying steps while performing the conveying step, a plurality of sections of the first and second elastic elements is arranged on the first web in generally parallel relation (Step 2222). As previously explained, this plurality of elastic elements distributed longitudinally along the web and in mutual parallel relation provides an elasticized region in the web output and in each individual, finished elastic composite product, according to the present invention.

FIGS. 23-27 depict a system and system components, and illustrate a method of making an elastic composite according to another embodiment of the invention. Again, the depicted system and its components are substantially similar in structure and operation to those previously described. Applicable detail descriptions of the system components and operation may be borrowed from earlier portions of this disclosure. Differences between the previously described systems and the systems to be described represent or arise from improvements provided by the present embodiment. Such differences are discussed herein in more detail.

Figure 23:
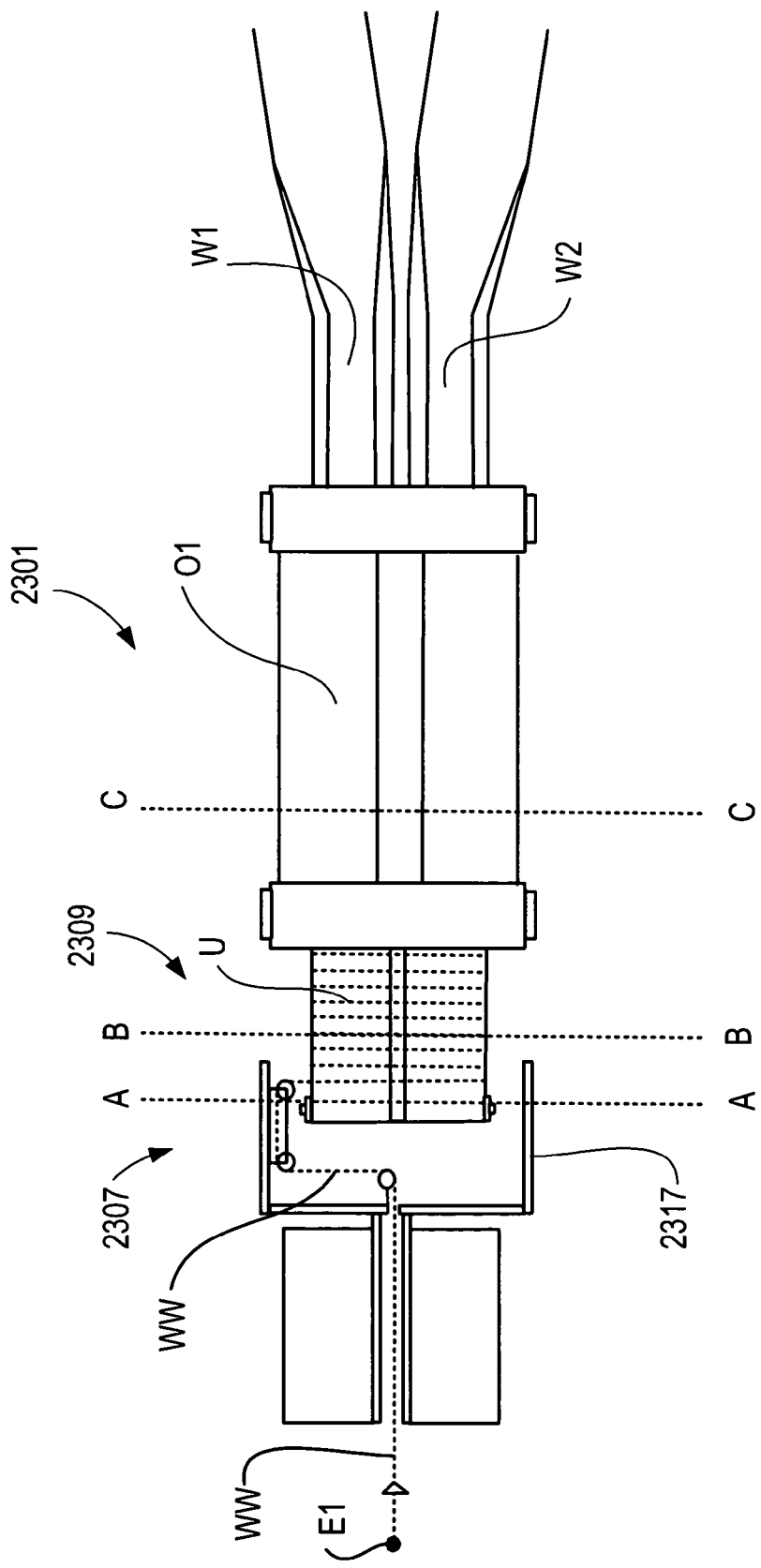
FIG. 23 is a top view of a system for making an elastic composite, according to an embodiment of the present invention.
Figure 24:
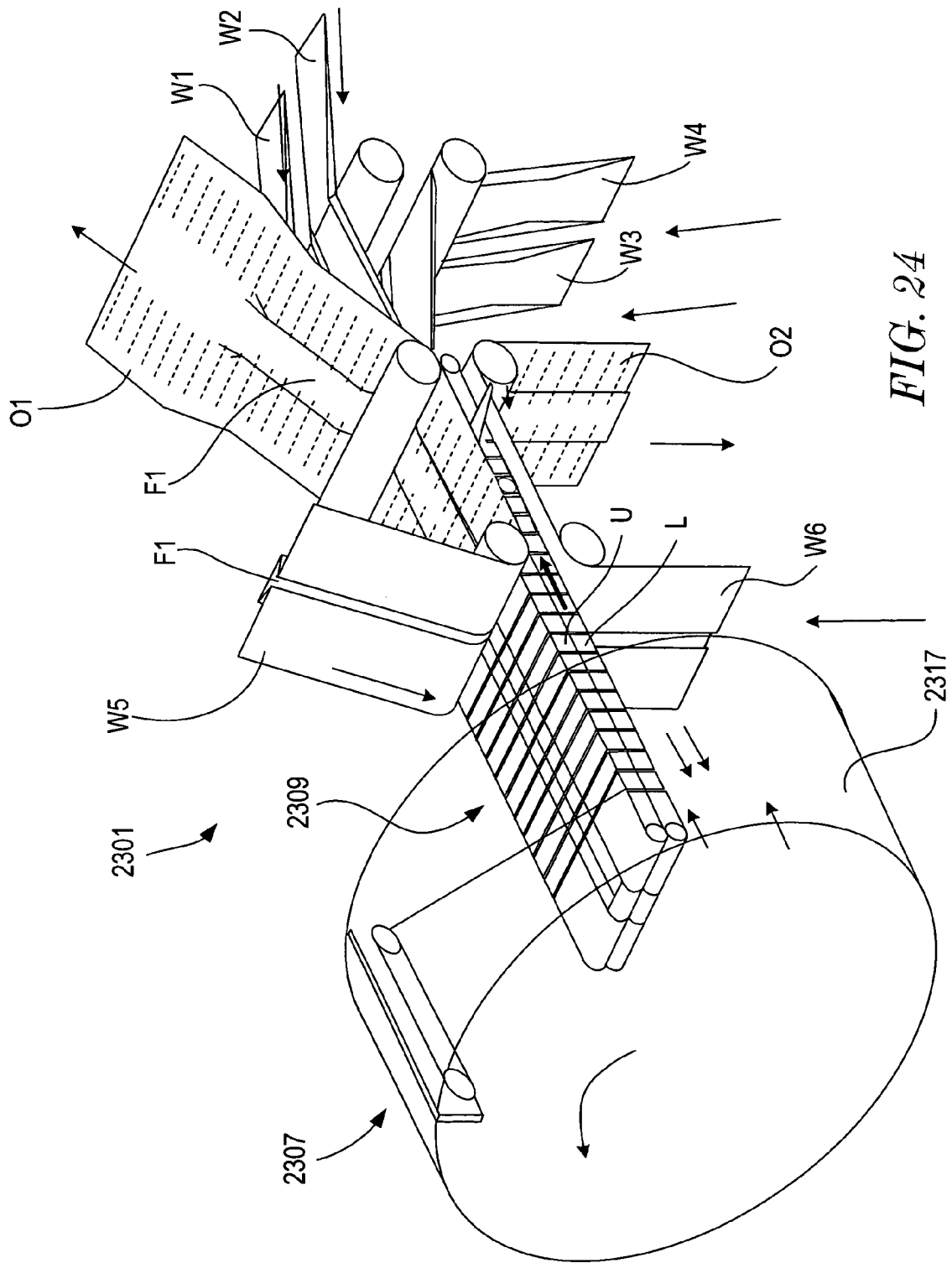
FIG. 24 is a perspective view of the system in FIG. 23.

FIG. 23 provides a plan view of the inventive system 2301. FIG. 24 provides a perspective, isometric view that reveals several of the components of the inventive system. Directional arrows are provided throughout FIG. 24 to indicate the movement of conveyors, web of materials or elastic composites, the spinhead assembly, and the like.

In this particular set of embodiments, a system provides and a method is implemented for making an elastic composite, whereby a continuous strand of elastic is applied onto a first and a second web along a direction generally transverse to a web plane moving direction. In these embodiments, the first and second input webs are conveyed along the web plane moving direction. This means that a plane may be extended from (and including) one web into (and including) the other web, and the two webs move along that plane in the same direction (i.e., parallel directional vectors, such as 90 degrees horizontally and vertically of the vertical plane XX). The two moving webs are, therefore, generally coplanar about the locations or sections whereupon a section of the elastic strand is applied to both webs. Moreover, the section of elastic strands is applied generally "linearly" onto both the first and second webs. As used heretofore, this reference to the section of strand being applied "generally linearly" means that the applied section generally provides a linear segment that extends across the planes of both the first and second webs and includes a shorter linear segment on each of the first and second webs.

Figure 25A:
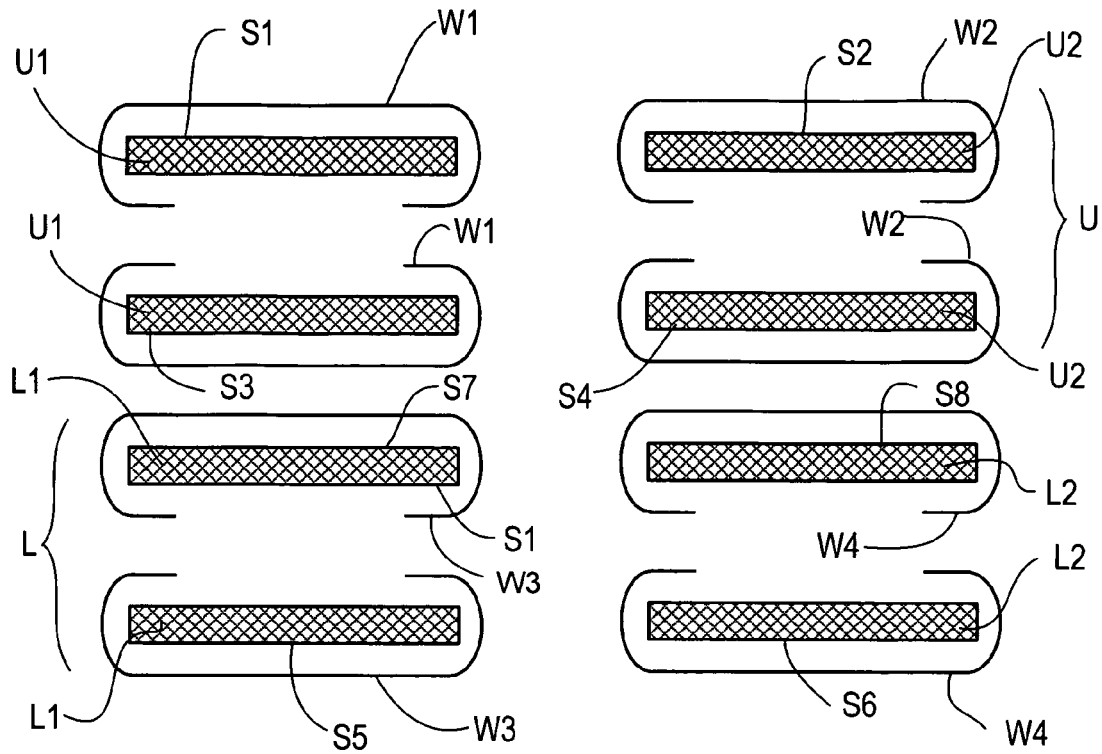
FIG. 25A is a cross-sectional view through line AA in FIG. 23.

Referring to FIGS. 23 and 24, as well as the cross-sectional view of FIG. 25A, a system 2301 is provided to implement the inventive method and produce a web output O1 of inventive elastic composite and preferably a second web output O2. A conveyor assembly 2309 is provided having a web platform U and preferably a second web platform L (for outputting second web output O2). In this embodiment, an upper web platform U is positioned above, and generally aligned with, a lower web platform L. Each web platform U, L is referred to as having a pair of conveyors in the form of movable continuous belts. Referring specifically to the cross-sectional view of FIG. 25A, a left continuous belt U1 of the upper platform U is spaced laterally from a second continuous belt U2. Lower web platform L also has similarly positioned left continuous belt L1 and right continuous belt L2.

The continuous belts U1 and U2 are referred to as having, at any given point in time, an inside deck or surface S3, S4 that is moving toward the spinhead 2317 (in the web plane moving direction MM) and an outside deck or surface S1, S2 that is moving away from the spinhead 2317 (in the web plane moving direction NN). As will be further described below, the outside surfaces S3, S4 are generally co-planar or at least corresponding sections of the surfaces S3, S4 are, such that sections of input webs supported on the corresponding sections are co-planar and positioned to receive a section of elastic strand that extends linearly across the two webs. Similarly, continuous belts L1, L2 have inside surfaces S7, S8, which are moving toward the spinhead 2317, and outside surfaces S5, S6, which are moving away from the spinhead. Accordingly, the pair of inside surfaces for each web platform may be referred to as being generally disposed on the same imaginary, extended plane and the pair of outside surfaces may be referred to as being generally disposed on another imaginary, extended plane. In these preferred embodiments, the two imaginary, extended planes are spaced vertically apart and generally disposed in parallel relation. Thus, S1 and S2 are generally on the plane, as are S3 and S4, S7, and S8, and S5 and S6. The pairs of continuous belts are, therefore, operable to convey a pair of input webs along a predetermined web plane path, first along a first web plane moving direction toward the spinhead and a second, reversed, web plane moving direction away from the spinhead. It is preferred, of course, to convey the pair of input webs at the same time.

An elastic applicator assembly 2307, including a spinhead 2317, in this embodiment, has a construction that is consistent with that previously described in respect to FIGS. 10-13. It will be apparent, however, that sizes and dimensions may be different to accommodate the dual web platform assembly. In any event, a single input source E1 of a continuous elastic strand WW is provided and received by a motor operatively associated with the spinhead described before. The spinhead 2317 includes arms as described previously, and a series of rollers and eyelets for routing and applying the continuous elastic strand WW about the conveyor assembly 2309 and about the generally vertical plane XX.

Referring now to FIG. 24, this exemplary system is provided with four independent sources of a primary input web of nonwoven: a first input web W1 arriving from an upper part of the system; a second input web W2 lower web arriving also from an upper part of the system; a third input web W3 generally below the first input web W1; and a fourth input web W4 generally below the second input web W2. Each of the four primary input webs W1-W4 is preferably processed through a folding mechanism, as described previously. The four input webs are then moved along a first web plane moving direction MM and in between the upper and lower web platforms U1, L1. Movement of the input webs is, of course, driven by the four continuous belts U1, U2, L1, L2.

The exemplary system is further provided with an upper secondary input web W5 of nonwoven positioned above the conveyor assembly 2309 for applying a base layer simultaneously to a pair of elasticated substrates as will be described below. Similarly, a lower secondary input web W6 is provided for applying a base layer, as will also be discussed below. Finally, a pair of large rollers 2342, 2344 is positioned downstream of the conveyor assembly 2309. Each roller serves to output a web O1 or O2 of elastic composite from the system. For this exemplary system and process, that web output O1, O2 will provide a dual-elasticized elastic composite 2322 according to the invention.

Figure 25B:
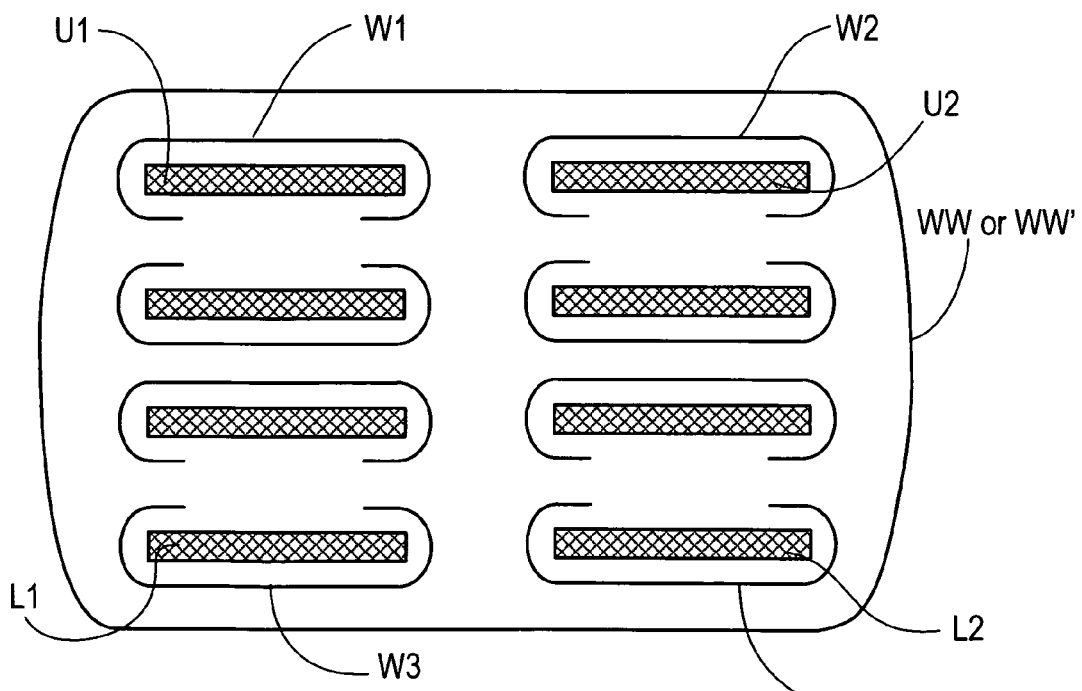
FIG. 25B is a cross-sectional view through line BB in FIG. 23.
Figure 25C:
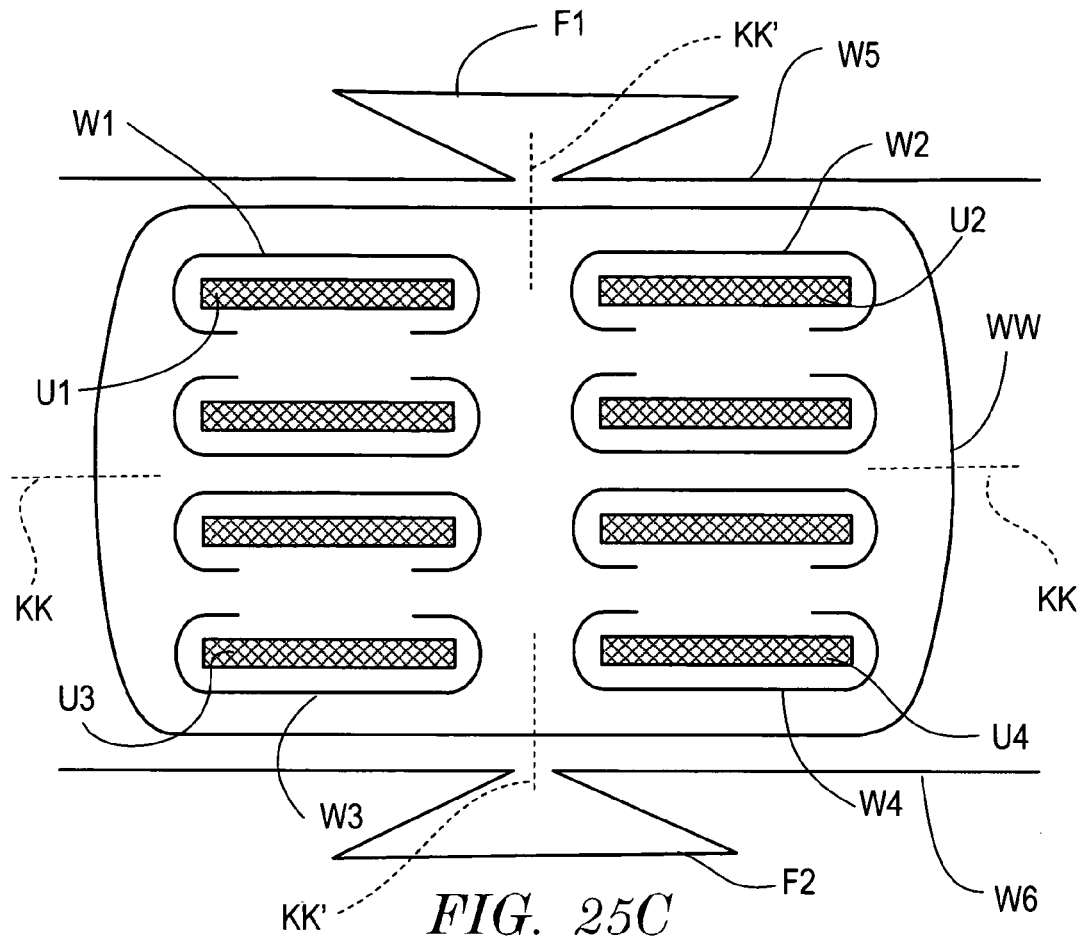
FIG. 25C is a cross-sectional view through line CC in FIG. 23.

Each of FIGS. 25A-25C provides a cross-sectional view through various points in the process and through sections of the system depicted in FIG. 23. The cross-sectional view of FIG. 25A is placed to highlight the two web platforms U, L, the four continuous belts U1, U2, L1, L2, and the four input webs W1-W4 conveyed thereon. The four webs W1-W4 are conveyed in a direction coming out of the page and toward the spinhead (i.e., first web plane moving direction MM). As also shown in FIG. 25A, the ends of the input webs W1-W4 enter the spinhead 2317 in a folded configuration.

The cross-sectional view of FIG. 25B is provided downstream of the spinhead 2317 and of the vertical plane XX. Thus, an elastic strand WW is applied continuously about the conveyor assembly 2309 and upon each of the four primary webs W1-W4 of nonwoven. Friction between the input webs W1-W4 and the applied elastic strand WW helps draw the continuous strand WW from the spinhead 2317.

Turning to FIG. 25C, the cross-sectional view is moved further downstream in the process. Specifically, the cross-section is provided at a point in the process after application of the secondary web inputs W5, W6. In one aspect of the present invention, one secondary input web is used in conjunction with the two primary input webs to create the elastic composite. A secondary nonwoven is shown applied upon the substrate combination of elastic elements and adjacent pair of input webs (W1 and W2; W3 and W4). The application of the secondary input web W5, W6 of nonwoven provides, therefore, an elastic composite. FIG. 25C also illustrates the use of central folded section F1, F2 in each secondary input webs W5, W6. The secondary input web W5, W6 is folded so as to later reveal a central dead zone between two elasticized regions of the elastic composite. This feature of the inventive elastic composite is discussed in further detail below.

FIG. 25C also indicates the location of a knife mechanism KK downstream of the cross-section as discussed previously. At these horizontal locations, the knife mechanisms cut elastic strand WW, thereby severing elastic elements from the continuous strands. The cuts also separates the process into an upper process and a lower process. More specifically, the cuts separates the upper, moving substrate consisting of input webs W1, W2, secondary input web W5 and elastic elements therebetween, from a similarly constituted lower, moving substrate. Additionally, another pair of knife mechanisms KK' is positioned at locations downstream of the cross-sectional view and, above, and below, the centers of the web platforms U, L. The knife mechanisms KK' are located to purposefully coincide with the middle of the central folded sections F1, F2. At these locations, the continuous elastic strand WW (or elastic element, if knife mechanisms KK' are downstream of knife mechanisms KK) is severed to provide a left and right elastic segment or element in the finished elastic composite. As already discussed, this also provides right and left elasticized regions and leaves the central part of the web absent of elastic elements. Thus, when the folded sections F1, F2 is unfolded, the central dead zone is needed.

Figure 26:
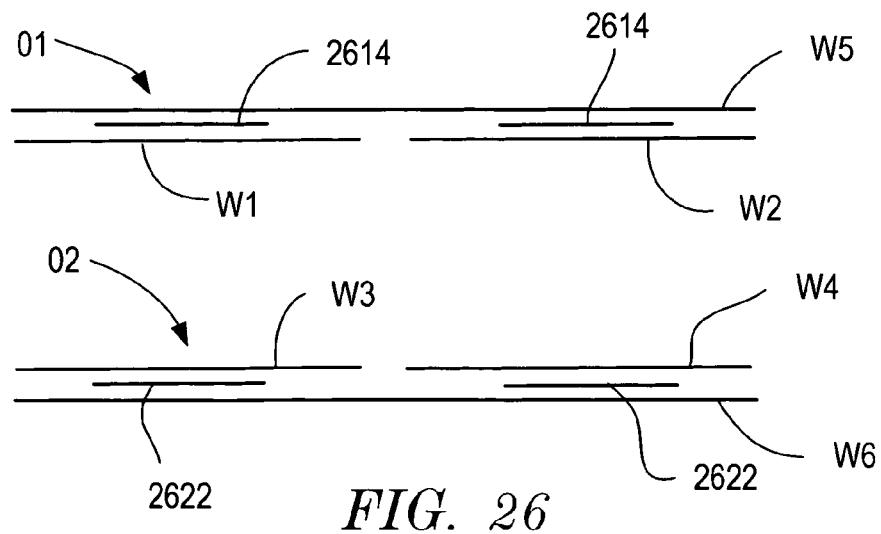
FIG. 26 is a cross-sectional view of a web output of elastic composite, according to the present invention.

FIG. 26 provides a cross-sectional view of a finished web output of the system and process. Two identical web outputs O1, O2 of elastic composites are provided. Referring to the web O1, a first nonwoven layer is provided by the pair of primary input webs W1, W2, a second nonwoven layer is provided by the single secondary input web W5, and a pair of elasticized regions 2614 therebetween make up the finished elastic composite web. The elasticized regions 2614 are provided by a distribution of elastic elements 2622 that are in generally parallel relation and extend laterally. The elastic elements also provide, as a result, elasticity in the lateral direction and without a vertical component. The two elasticized regions 2614 are laterally spaced from one another to provide a dead zone 2650 therebetween. As discussed above, the dead zone results from cutting the elastic strand WW or elastic element using the knife mechanisms KK' and the unfolding of the folded sections F1, F2. Dead zones are also provided between the side edges of the nonwovens and each of the elasticized regions. The side dead zones result partly from the unfolding of the folded ends of the primary input webs W1-W4. These unfolding steps may be performed immediately downstream of the two knife mechanisms in a manner previously described in this disclosure.

The width of the central non-elasticized region or dead zone 2650 may be controlled by controlling the lateral separation between the pairs of belts in each web platform (e.g., the space between U1 and U2 and the space between L1 and L2). It may also be controlled by specifying the width of the excess fold in the center of the secondary web. This fold is configured to retain some of the material away from the composite during the process and is typically opened up downstream to reveal the central non-elasticized region or dead zone.

In an alternative embodiment, the system 2301 and method are modified to produce four web outputs and four separate elastic composites, according to the present invention. In one variation, the knife mechanisms KK' may be modified to also sever the secondary input webs W5,W6 (in addition to the elastic strand WW). In this way, each of the two web substrates is divided to produce an independent elastic composite to the left and also to the right of the knife mechanisms KK'. Each elastic composite has a single central elasticized region and two side dead zones. In the method to create the pairs of elastic composites, the width of the folded sections F1, F2 may be provided to correspond with the folded ends of the primary input webs.

In yet another alternative embodiment, four independent secondary input webs are used instead of two. Each secondary input web joins with a primary input web, with elastic elements, thereon, to produce an elastic composite having a centralized region. The elastic composite also has a pair of dead zones on either side of the central elasticized region.

Figure 27:
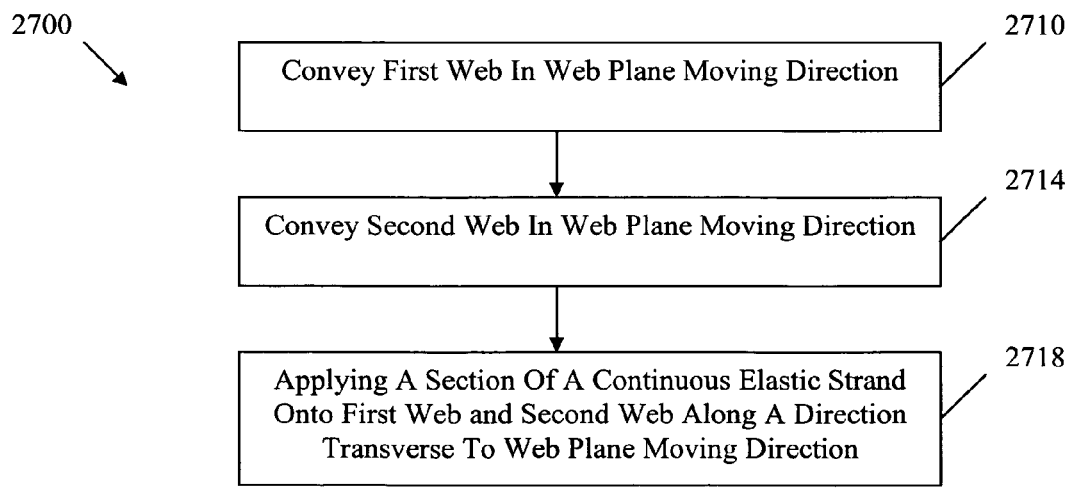
FIG. 27 is a simplified flow chart illustrating basic steps of a method of making an elastic composite, according to the present invention.

FIG. 27 provides a simplified flow chart of the basic steps of a method of making an elastic composite, in accordance with this embodiment of the present invention. The flow chart 2700 also summarizes the process described above in respect to FIGS. 23-25. The basic steps of the method are preferably performed through operation of a system such as the exemplary system 2301 in FIGS. 23 and 24.

In initial steps 2710, 2714, a first web of material is conveyed along a web plane moving direction and a second web of material is conveyed along the web plane moving direction. Preferably, the web plane moving direction is predetermined by the web platforms of a conveyor assembly and the conveying steps 2710, 2714 are implemented through operation of the web platforms. A section of a first continuous elastic strand is then applied generally linearly onto both the first and second webs along a direction generally transverse to the web plane moving direction (Step 2718). The applying step 2718 is preferably performed through operation of a spinhead that spins the elastic strand about the first and second webs as these webs are conveyed along the web plane moving direction. Preferably, the applying step 2718 is performed while performing the conveying steps 2710, 2714 such that a plurality of sections of the first and second elastic elements are arranged on each of the first web and the second web in generally parallel relation. The elastic elements are distributed longitudinally along the web and in mutual parallel relation, so as to provide, in the finished elastic composite, an elasticized region. In one embodiment, the first and second webs provide a top or base layer and the first and second arrangements of elastic elements provide the pair of elasticized regions.

Figure 28A:
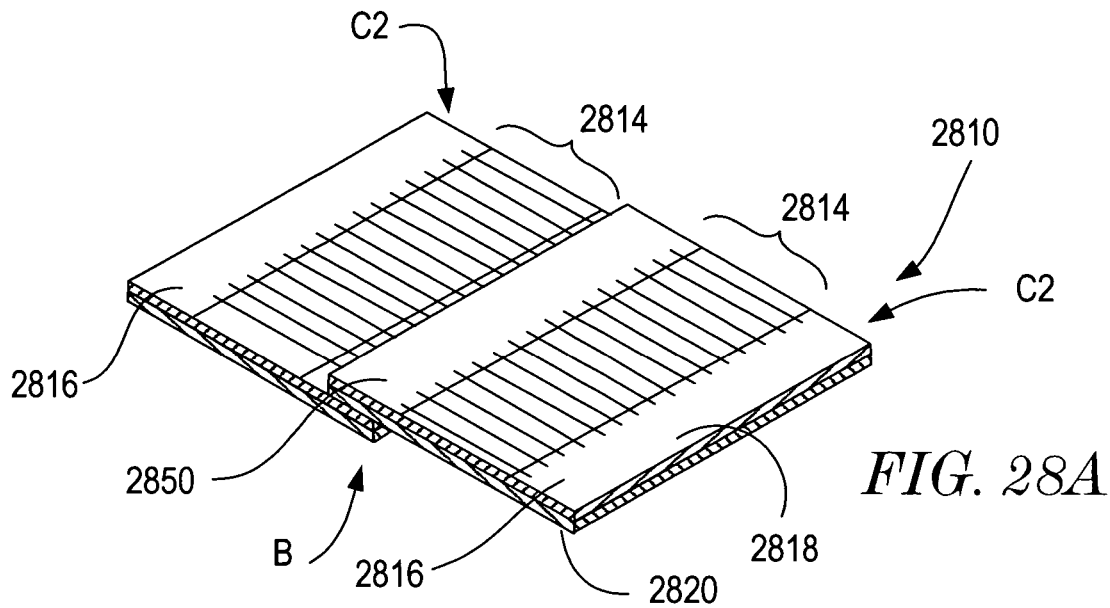
FIG. 28A is a perspective view of an elastic composite having dual elasticized regions.
Figure 28B:
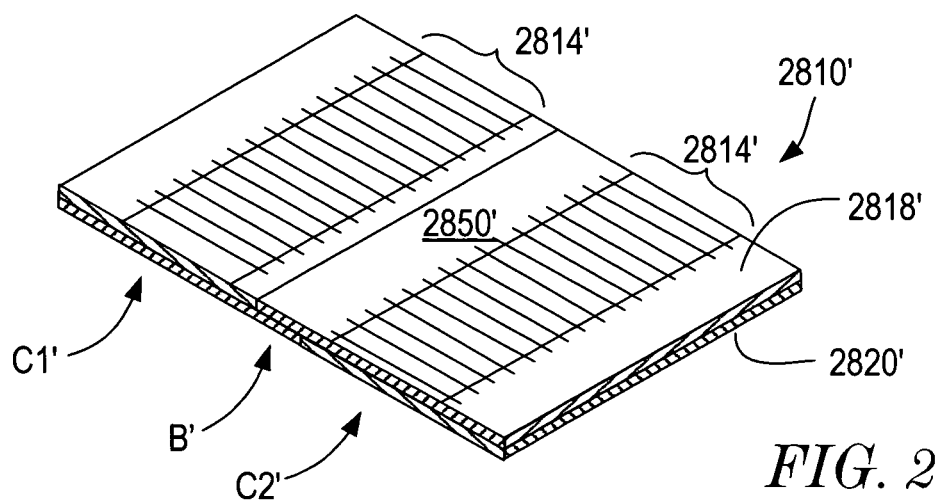
FIG. 28B is a perspective view of another elastic composite having dual elasticized regions.
Figure 28C:
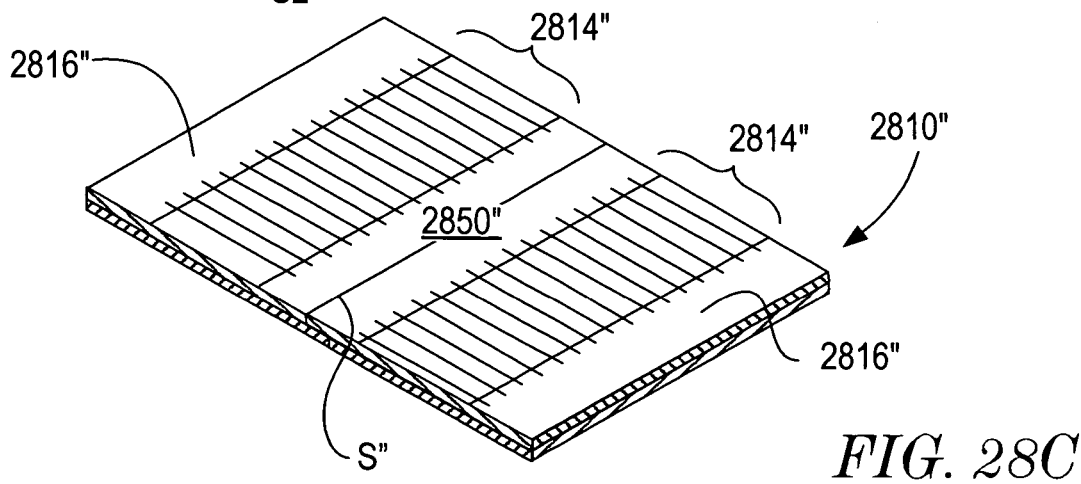
FIG. 28C is a perspective view of an elastic composite having dual elasticized regions, according to another embodiment of the present invention.

Each of FIGS. 28A-28C illustrates an elastic composite 2810 containing a pair of elasticized regions 2814 and three non-elasticized zones or dead zones, including a central dead zone 2850 extending longitudinally between the two elasticized regions 2814 and side dead zones 2816, 2818 on the other side of each elasticized region 2850. The elastic composite 2810 may be referred to herein as a dual-elasticized elastic composite. In FIG. 28A, the elastic composite 2810 shown is formed from two discrete composite sections C1, C2. Each composite section C1, C2 is manufactured independently as a discrete elastic composite having a single elasticized region. Any one of the three methods described herein may be employed to make the singly elasticized composite section. To form the dual-elasticized elastic composite, two of the singly elasticized composite sections are joined together by overlapping one side edge of one composite section over a side edge of the other composite section. A suitable adhesive or adhesive means may be used to maintain bonding at the overlap. The overlap creates a multi-layer bonding portion B as shown in FIG. 28A, which also serves as a portion of the central dead zone.

The bonding portion B consists of a top nonwoven layer 2818 and a base layer 2820 of each composite section. Accordingly, the thickness of the bonding portion B and the central dead zone 2850 may be significantly, or at least observably, greater than the thickness of the rest of dual-elasticized elastic composite. For each composite section C1, C2, the top nonwoven layer 2818 and the base nonwoven layer 2820 have the same width and the side edges are aligned.

Turning to FIG. 28B, a second dual-elasticized elastic composite 2810' is shown again consisting of two adjoined singly elasticized, composite sections C1', C2'. For each composite section C1', C2', one of a top layer 2818' and a bottom layer 2820' is wider than the other. Referring to the view of FIG. 28B, the right composite section C2 has a bottom layer 2820' that extends laterally farther than the top layer 2818', thereby forming a step. For the left composite section, the top layer 2818' extends laterally farther than the bottom layer 2820', thereby forming a ledge. By abutting the ledged side edge to the stepped side edge, a suitable construction joint is provided between the two composite sections C11', C2'. An overlapping bonding portion B' (and central dead zone 2850') is also provided that consists of a single top layer 2818' and a single base layer 2820' and is characterized by a thickness generally consistent with the other portions of the dual elasticized elastic composite 2810'. A suitable adhesive or adhesive means may be employed to facilitate and maintain bonding between the layers of the bonding portion.

FIG. 28C illustrates an improved dual elasticized elastic composite 2810" that may be manufactured in accordance with the method described in respect to FIGS. 23-26, in accordance with the present invention. In addition to a pair of elasticized regions 2814", the elastic composite also has two side dead zones 2816" and a central dead zone 2850" situated between the elasticized regions 2814". The thickness of the dead zone 2850" is provided by a single top layer 2818" and a single base layer 2820" and is, therefore, consistent with the thickness of other portions of the dual elasticized elastic composite 2810". In one aspect of the present invention, the dual elasticized elastic composite 2810" provides a single composite structure. The base layer 2820" of the elastic composite 2810" is provided by a seamless sheet of nonwoven (or other material). The elastic composite 2810" does not require joining of two discrete elastic composite sections. Rather, a web of the dual elasticized elastic composite 2810" is generated linearly as output of the method described in respect to FIGS. 23-27. A seamless composite structure, the dual elasticized composite 2810 eliminates the bonding region required of the elastic composites in FIGS. 28A and 28B and thus, avoids the potential for leakage generally associated with these bonding regions B, B'. The seamless composite structure is also more structurally sound than the other composites and has a higher tensile strength (laterally and longitudinally).

As used herein, the term "seamless composite structure" shall refer to a structure that does not have a seam at which two or more originally independent sections are joined as one to form the present structure. It should be noted that the top layer 2818" of the elastic composite 2810 in FIG. 28C may provide a single seam S" along the central dead zone 2850" and thus, may not be referred to as "seamless." This seam S" of the top layers 2818" is not, however, a seam of the elastic composite 2810" as that seam S" does not extend through the thickness of the dead zone 2850" and the multi-layer composite 2810", and is not required to join two independent sections of the elastic composite 2810".

As expected, the dual elasticized elastic composite 2810" is generally easier to manufacture than the other composites in that it does not require the joining and bonding steps required described previously. It also does not require the machines or manpower to implement these steps. Furthermore, the seamlessness of the elastic composite 2810" is generally more aesthetically pleasing than the bonding regions B, B'. By eliminating or reducing the use of adhesives, the central dead zone of the present elastic composite is also generally cleaner. Further advantages and benefits of the dual elasticized composite according to the invention, or of the method of making same, will be apparent to one generally skilled in the art.

The foregoing description of the present invention has been presented for purposes of illustration and description. It is to be noted that the description is not intended to limit the invention to the various systems, apparatus, and processes disclosed herein. Various aspects of the invention, as described above, may be applicable to other types of disposable absorbent articles, garments, and the like, and processes for making the same. For example, the elastic composite described above, may be incorporated in other disposable absorbent garments such as training pants, etc. or in other areas or as other components of the garment. The elastic composite may also be incorporated into or with other garments, textiles, fabrics, and the like, or combinations thereof. Moreover, the various aspects of the process described in respect to FIGS. 17-28 may be utilized to produce compositions, garments and articles other than those described herein. Such variations of the invention will become apparent to one skilled in the relevant consumer products art provided with the present disclosure. Consequently, variations and modifications commensurate with the above teachings, and the skill and knowledge of the relevant art, are within the scope of the present invention. The embodiments described and illustrated herein are further intended to explain the best modes for practicing the invention, and to enable others skilled in the art to utilize the invention and other embodiments and with various modifications required by the particular applications or uses of the present invention.

What is claimed is:

1. A method of making an elastic composite, said method comprising the steps of:
   conveying a first web of nonwoven sheet on a moving platform, whereby the first web moves along a predefined web plane path;
   applying a first section of a first elastic strand onto the first web on the moving platform and generally transversely to the moving web;
   applying a second section of a second elastic strand onto the first web on the moving platform and generally transversely to the moving web; and
   repeating said applying steps while performing said conveying step, thereby arranging a plurality of first and second elastic elements on the first web, in generally parallel relation to one another.

2. The method of claim 1, wherein each of the first and second sections of elastic strand is applied to the first web by moving the section about an elastic applying plane that intersects the moving web, the method further comprising:
   applying a second web of material onto the first web on the moving platform having a plurality of elastics thereon, thereby securing the elastic strands between two layers of material.

3. The method of claim 2, further comprising feeding a first continuous strand of a first elastic strand having said first section, from a first side of the elastic applying plane and along a first direction toward said elastic applying plane and feeding a second continuous strand of a second elastic having said second section, from a second side of the elastic applying plane and along a second direction toward said elastic applying plane.

4. The method of claim 1, wherein each said applying steps include spinning the first and second elastic strands about a plane simultaneously with said conveying step, whereby the plane intersects the moving web and whereby said first and second sections are applied simultaneously onto the first web in side by side generally parallel relation.

5. The method of claim 1, wherein said applying steps include alternately applying sections of first and second elastic strands on the web; and
   wherein the step of conveying the first web along the web plane path includes moving the first web along a first direction toward and past the elastic applying plane and then moving the first web in a reverse direction toward and past the elastic applying plane, whereby the elastics are applied on the first web moving in the reverse direction.

6. The method of claim 1, further comprising the step of securing the elastic elements on the first web, after said applying steps,
   wherein said applying steps includes spacing the sections of elastic strands on the first web such that, said subsequent step of securing the elastic elements provides an elasticized region on the first web that extends centrally along the first web.

7. The method of claim 1, further comprising spinning sections of two separate continuous strands to effect said applying steps, such that a pair of spaced apart sections of elastic element is applied onto the first web within each spin revolution, and wherein said spinning and applying steps are repeated to apply a plurality of pairs of elastic elements on the first web in spaced apart, generally parallel relation.

8. The method of claim 1, wherein the first section is fed by a first continuous elastic strand and the second section is fed by a second continuous elastic strand independent and distinct from said first continuous strand.

9. The method of claim 1, wherein said applying steps are performed to provide a distribution of alternating first and second elastic elements on the first web, whereby the pitch between successive pairs of first and second elastic elements is alternated between a first pitch and a second pitch.

10. The method of claim 1, wherein the sections of elastic element are moved about a plane intersecting a web plane path of the first web in a reciprocal pattern to periodically apply the sections of elastic element onto the first web, thereby applying a plurality of elastic strands onto the first web, wherein the elastic strands are applied in generally parallel relation on the first web.

11. The method of claim 10, further comprising the steps of:
    cutting each applied section of elastic element at opposing ends applied proximate the lateral side edges of the first web, thereby providing a plurality of distinct elastic elements on the first web; and
    applying a second web of material onto the first web having a plurality of elastic elements applied thereon, thereby providing a web of elastic composite comprising of at least two layers of material and a plurality of elastic strands sandwiched therebetween.

12. The method of claim 1, further comprising the step of conveying a second web spaced apart from the first web and along a second web plane path that is generally parallel with a web plane path of the first moving web, whereby the applying steps applies elastic elements on outward faces of the first and second webs of material.

13. The method of claim 12, wherein said applying steps are performed simultaneously such that the elastic elements are applied generally simultaneously on the first web and the second web.

14. The method of claim 1, further comprising the steps of folding each of the side edges of the first web along a side fold line and inwardly toward an inward surface of the first web to create a pair of folded flaps adjacent the inward surface, such that, in said applying steps the elastic elements are applied across the width of an exposed outward surface of the first web, the exposed outward surface having a width defined between the fold lines.

15. The method of claim 14, further comprising the steps of:
    cutting each section of elastic element proximate each of the fold lines of the first web, thereby separating each section from the continuous strand and creating a plurality of separate elastic elements on the outward surface of the first web, whereby the lengths of the elastic elements are generally equal to the width of the outward surface; and
    unfolding the folded flaps of the first web such that the resulting first web has applied thereon a plurality of centrally located elastic strands and non-elasticized side regions defined generally outward of the fold lines.

16. The method of claim 1, further comprising positioning a spinning assembly relative to the platform for receiving the first and second sections of strands and spinning the first and second sections of the strands about a plane that intersects the platform, wherein the spinning step includes operating the spinning assembly to spin the sections of strands about the plane.

17. The method of claim 16, wherein the spinning assembly includes a spin head positioned for spinning about the platform, said method further comprising the steps of:
positioning a feed source of the first elastic strand in spaced apart relation to the spin head;
positioning a feed source of the second elastic in spaced apart relation to the spin head; and
feeding a continuous strand from each of the feed sources to the spin head, whereby the spinning step draws the sections of continuous elastic strand from the feed sources.

18. The method of claim 17, wherein the feeding steps includes directing each of the continuous elastic strands generally toward a center axis of the elastic applying plane.

19. The method of claim 1, wherein the applying steps include spinning the first and second sections of elastic strand generally about a plane; and
wherein the conveying steps include moving the first web along a first web moving direction into and generally past the plane and redirecting the first web in a second web moving direction that is a reverse of the first web moving direction such that the first web returns to intersect the plane, whereby the section of elastic strand is applied onto the returning first web along a direction generally transverse to the web moving direction.

20. A method of making an elastic composite, said method comprising the steps of:
conveying a first web of sheet material on a moving platform along a web plane moving direction;
feeding a first continuous strand of a first elastic strand, from a first direction;
feeding a second continuous strand of a second elastic from a second direction;
spinning a first section of the first elastic strand onto a moving first web and generally transversely to the moving first web on the moving platform;
spinning a second section of the second elastic strand onto the moving first web and generally transversely to the moving first web on the moving platform; and
repeating said spinning steps while performing said conveying step, thereby arranging a plurality of first and second elastic elements on the first web on the moving platform, in generally parallel relation to one another.

21. The method of claim 20, wherein each of the first and second sections of elastic strand is applied to the first web by spinning the section about an elastic applying plane that intersects the moving first web, wherein each of the first and second sections of elastic strand is applied onto the first web at an intersection of the elastic applying plane and the moving first web.

22. The method of claim 20, wherein said spinning steps include alternately applying sections of first and second elastic strands on the web.

23. The method of claim 20, wherein the spinning and conveying steps are performed such that a pair of spaced apart sections of elastic element is applied onto the first web within each spin revolution, and wherein said spinning steps are repeated to apply a plurality of pairs of elastic elements on the first web in spaced apart, generally parallel relation.

24. The method of claim 20, further comprising the step of securing the elastic elements on the first web, after said spinning steps,
wherein said spinning steps include spacing the sections of elastic strands on the first web such that, said subsequent step of securing the elastic elements provides an elasticized region on the first web that extends centrally along the first web.

25. The method of claim 20, wherein said spinning steps are performed to provide a distribution of alternating first and second elastic elements on the first web, whereby the pitch between successive pairs of first and second elastic elements is alternated between a first pitch and a second pitch.

26. A method of making an elastic composite, said method comprising the steps of:
conveying a first web of nonwoven sheet on a moving platform, whereby the first web moves along a predefined web plane path;
applying a first section of a first elastic strand onto the first web on the moving platform and generally transversely to the moving web and applying a second section of a second elastic strand onto the first web on the moving platform and generally transversely to the moving web;
repeating said elastic strand applying steps while performing said conveying step, thereby arranging a plurality of first and second elastic elements on the first web, in generally parallel relation to one another; and
applying a second web of material onto the first web on the moving platform having a plurality of elastics thereon, thereby securing the elastic strands between two layers of material; and
wherein the elastic strand applying steps include feeding a first continuous strand of a first elastic strand having said first section, from a first side of the elastic applying plane and along a first direction toward said elastic applying plane and feeding a second continuous strand of a second elastic having said second section, from a second side of the elastic applying plane and along a second direction toward said elastic applying plane.

27. The method of claim 26, further comprising the steps of:
positioning a feed source of the first elastic strand in spaced apart relation to the spin head; and
positioning a feed source of the second elastic in spaced apart relation to the spin head; wherein the feeding steps include feeding a continuous strand from each of the feed sources to the spin head, whereby the spinning step draws the sections of continuous elastic strand from the feed sources.

* * * * *